(12) United States Patent
Bachmann

(10) Patent No.: US 7,115,266 B2
(45) Date of Patent: *Oct. 3, 2006

(54) ANGIOTENSIN PEPTIDE-CARRIER CONJUGATES AND USES THEREOF

(75) Inventor: Martin Bachmann, Seuzach (CH)

(73) Assignee: Cytos Biotechnology AG, Zurich-Schlieren (CH)

( * ) Notice: Subject to any disclaimer, the term of this patent is extended or adjusted under 35 U.S.C. 154(b) by 559 days.

This patent is subject to a terminal disclaimer.

(21) Appl. No.: 10/264,267

(22) Filed: Oct. 4, 2002

(65) Prior Publication Data

US 2006/0078554 A1 Apr. 13, 2006

Related U.S. Application Data

(63) Continuation-in-part of application No. PCT/IB02/00166, filed on Jan. 21, 2002, and a continuation-in-part of application No. 10/050,902, filed on Jan. 18, 2001.

(60) Provisional application No. 60/396,637, filed on Jul. 19, 2002, provisional application No. 60/331,045, filed on Nov. 7, 2001, provisional application No. 60/326,998, filed on Oct. 5, 2001.

(51) Int. Cl.
*A61K 39/385* (2006.01)
*A61K 38/22* (2006.01)
*A61K 9/00* (2006.01)
*C07K 17/00* (2006.01)

(52) U.S. Cl. ............... 424/185.1; 424/193.1; 424/194.1; 424/195.11; 424/198.1; 424/400; 530/403; 530/404

(58) Field of Classification Search ............... 424/400, 424/185.1, 193.1, 194.1, 195.11, 198.1, 278.1, 424/288.1; 530/350, 403, 404
See application file for complete search history.

(56) References Cited

U.S. PATENT DOCUMENTS

| | | | |
|---|---|---|---|
| 4,722,840 A | 2/1988 | Valenzuela et al. | |
| 4,918,166 A | 4/1990 | Kingsman et al. | |
| 5,071,651 A | 12/1991 | Sabara et al. | |
| 5,334,394 A | 8/1994 | Kossovsky et al. | |
| 5,374,426 A | 12/1994 | Sabara et al. | |
| 5,580,589 A | 12/1996 | Stoves et al. | |
| 5,698,424 A * | 12/1997 | Mastico et al. ............. | 435/477 |
| 5,739,026 A | 4/1998 | Garoff et al. | |
| 5,766,602 A | 6/1998 | Xiong et al. | |
| 5,770,380 A | 6/1998 | Hamilton et al. | |
| 5,789,245 A | 8/1998 | Dubensky, Jr. et al. | |
| 5,792,462 A | 8/1998 | Johnston et al. | |
| 5,814,482 A | 9/1998 | Dubensky, Jr. et al. | |
| 5,876,727 A | 3/1999 | Swain et al. | |
| 5,935,821 A | 8/1999 | Chatterjee et al. | |
| 5,939,598 A | 8/1999 | Kucherlapati et al. | |
| 6,231,864 B1 | 5/2001 | Birkett | |
| 6,380,364 B1 | 4/2002 | Mueller et al. | |
| 2002/0064533 A1 | 5/2002 | Murray | |
| 2002/0081295 A1 | 6/2002 | Schiller et al. | |
| 2003/0175290 A1 | 9/2003 | Renner et al. | |
| 2003/0175711 A1 | 9/2003 | Renner et al. | |
| 2004/0059094 A1 | 3/2004 | Bachmann et al. | |
| 2004/0076611 A1 | 4/2004 | Bachmann et al. | |
| 2004/0076645 A1 | 4/2004 | Bachmann et al. | |
| 2004/0136962 A1 | 7/2004 | Renner et al. | |
| 2004/0141984 A1 | 7/2004 | Bachmann et al. | |

FOREIGN PATENT DOCUMENTS

| | | |
|---|---|---|
| EP | 0 201 416 A1 | 4/1986 |
| EP | 0 259 149 B1 | 12/1993 |
| EP | 0 578 293 A1 | 1/1994 |
| EP | 0 385 610 B1 | 3/1994 |
| EP | 0 465 081 B1 | 4/1994 |
| EP | 0 283 505 B1 | 7/1994 |
| EP | 0 425 082 A1 | 4/1995 |
| EP | 0 421 635 B1 | 7/1995 |
| EP | 0 677 111 B1 | 5/1997 |
| WO | WO 92/11291 A1 | 7/1992 |
| WO | WO 92/13081 | 8/1992 |
| WO | WO 94/06472 A1 | 3/1994 |
| WO | WO 94/15585 A1 | 7/1994 |
| WO | WO 96/05293 A1 | 2/1996 |
| WO | WO 96/30523 A2 | 10/1996 |
| WO | WO 97/31948 A1 | 9/1997 |
| WO | WO 98/15631 A1 | 4/1998 |
| WO | WO 98/58952 * | 12/1998 |
| WO | WO 99/07839 A2 | 2/1999 |
| WO | WO 99/28478 | 6/1999 |
| WO | WO 99/40934 A1 | 8/1999 |
| WO | WO 99/57289 | 11/1999 |
| WO | WO 99/61054 | 12/1999 |
| WO | WO 99/67293 A1 | 12/1999 |
| WO | WO 00/23955 * | 4/2000 |
| WO | WO 00/23955 A1 | 4/2000 |

(Continued)

OTHER PUBLICATIONS

Brown et al (Clinical Science 107:167-173, not prior art).*

(Continued)

*Primary Examiner*—Mary E. Mosher
(74) *Attorney, Agent, or Firm*—Sterne, Kessler, Goldstein & Fox PLLC

(57) ABSTRACT

The present invention provides conjugates of peptide derivatives of the mammalian peptide hormones angiotensinogen, angiotensin I and angiotensin II, presented in a repetitive scaffold by coupling the peptide derivatives to a carrier, particularly a virus-like particle (VLP). The invention also provides methods of producing such conjugates, and immunotherapeutic uses of the resulting immunogen conjugates for the therapy and prophylaxis of conditions associated with the renin-activated angiotensin system.

40 Claims, 4 Drawing Sheets

FOREIGN PATENT DOCUMENTS

| | | |
|---|---|---|
| WO | WO 00/32227 A2 | 6/2000 |
| WO | WO 01/62284 A2 | 8/2001 |
| WO | WO 01/77158 A1 | 10/2001 |
| WO | WO 01/85208 A2 | 11/2001 |
| WO | WO 01/98333 A2 | 12/2001 |
| WO | WO 02/14478 A2 | 2/2002 |

OTHER PUBLICATIONS

Michel (Clinical Science 107:145-147, 2004, not prior art).*
Kozlovska et al (Intervirology 39:9-15, 1996).*
Doggrell et al (Cardiovascular Research 39:89-105, 1998).*
Chackerian et al, Proceedings of the National Academy of Sciences US 96:2373-2378, 1999.*
Adhin, M.R., et al., "Nucleotide Sequence from the ssRNA Bacteriophage JP34 Resolves the Discrepancy between Serological and Biophysical Classification," *Virology* 170:238-242, Academic Press, Inc. (1989).
Bachmann, M.F., and Zinkernagel, R.M., "The influence of virus structure on antibody responses and virus serotype formation," *Immunol. Today* 17:553-558, Elsevier Science, Ltd. (1996).
Bachmann, M.F., and Zinkernagel, R.M., "Neutralizing Antiviral B Cell Responses," *Annu. Rev. Immunol.* 15:235-270, Annual Reviews, Inc. (1997).
Biaselle, C.J., and Millar, D.B., "Studies on Triton X-100 detergent micelles," *Biophys. Chem.* 3:355-361, North-Holland Publishing Company (1975).
Bullitt, E., et al., "Development of pilus organelle subassemblies in vitro depends on chaperone uncapping of a beta zipper," *Proc. Natl. Acad. Sci. USA* 93:12890-12895, National Academy Press (1996).
Bullitt, E., and Makowski, L., "Bacterial Adhesion Pili Are Heterologous Assemblies of Similar Subunits," *Biophys. J.* 74:623-632, Biophysical Society (1998).
Corti, M., et al., "GM1-ganglioside-Triton X-100 mixed micelles: changes of micellar properties studied by laser-light scattering and enzymatic methods," *Chem. Phys. Lipids* 28:197-214, Elsevier/North-Holland Scientific Publishers, Ltd. (1981).
Coutelier, J.-P., et al., "IgG2a Restriction of murine antibodies elicited by viral infections," *J. Exp. Med.* 165:64-69, The Rockefeller University Press (1987).
Davis, N.L., et al., "In Vitro Synthesis of Infectious Venezuelan Equine Encephalitis Virus RNA from a cDNA Clone: Analysis of a Viable Deletion Mutant," *Virology* 171:189-204, Academic Press (1989).
Eckhardt, S.G., et al., "Heptatitis B Virus Core Antigen Has Two Nuclear Localization Sequences in the Arginine-Rich Carboxyl Terminus," *J. Virol.* 65:575-582, American Society for Microbiology (1991).
Eshdat, Y., et al., "Dissociation and Reassembly of *Escherichia coli* Type 1 Pili," *J. Bacteriol.* 148:308-314, American Society for Microbiology (1981).
Fujiwara, K., et al., "Novel preparation method of immunogen for hydrophobic hapten, enzyme immunoassay for daunomycin and adriamycin," *J. Immunol. Methods* 45:195-203, Elsevier/North-Holland Biomedical Press (1981).
Golomohammadi, R., et al., "The crystal structure of bacteriophage Qβ at 3.5Å resolution," *Structure* 4:543-554, Current Biology, Ltd. (1996).
Kastelein, R.A., et al., "Effect of the sequence upstream from the ribosome-binding site on the yield of protein from the cloned gene for phage MS2 coat protein," *Gene* 23:245-254, Elsevier (1983).
Koschel, M., et al., "Extensive Mutagenesis of the Hepatitis B Virus Core Gene and Mapping of Mutations That Allow Capsid Formation," *J. Virol* 73:2153-2160, American Society for Microbiology (1999).
Kozlovska, T.M., et al., "Recombinant RNA Qβ capsid particles synthesized and self-assembled in *Escherichia coli* ," *Gene* 137:133-137, Elsevier Science Publishers B.V. (1993).
Kozlovskaya, T.M., et al., "Formation of capsid-like structures as a result of the expression of a cloned envelope protein gene from RNA-containing bacteriophage fr," *Dokl. Akad. Nauk. SSSR* 287: 452-455, Erivan Akademiia Nauk Armianskoi Ssr (1986).
Kozlovskaya, T.M., et al., "Formation of capsid-like structures as a result of the expression of a cloned envelope protein gene from RNA-containing bacteriophage fr," STNEasy, Accession No. 1986:219892, CAplus English abstract (1986) (Document AS6).
Liljeström, P., and Garoff, H., "A new generation of animal cell expression vectors based on the semliki forest virus replicon," *Bio/technology* 9:1356-1361, Nature Publishing Company (1991).
Liljeström, P., "Alphavirus expression systems," *Curr. Opin. Biotechnol.* 5:495-500, Current Biology, Ltd. (1994).
Lim, F., et al., "The RNA-binding Site of Bacteriophage Qβ Coat Protein," *J. Biol. Chem.* 271:31839-31845, The American Society for Biochemistry and Molecular Biology, Inc. (1996).
Bachmann, M.F., and Zinkernagel, R.M., "Neutralizing Antiviral B Cell Responses," *Annu. Rev. Immunol.* 15:235-270, Annual Reviews, Inc. (1997).
Bachmann, M.F., et al., "Dendritic cells process exogenous viral proteins and virus-like particles for class I presentation to CD8+cytotoxic T lymphocytes," *Eur. J. Immunol.* 26:2595-2600, VCH Verlagsgesellschaft mbH (1996).
Borisova, G., et al., "Hybrid Hepatitis B Virus Nucleocapsid Bearing an Immunodominant Region from Hepatitis B Virus Surface Antigen," *J. Virol.* 67:3696-3701, American Society for Microbiology (1993).
Borisova, G., et al., "Spatial Structure and Insertion Capacity of Immunodominant Region of Hepatitis B Core Antigen," *Intervirology* 39:16-22, S. Karger AG (1996).
Caldwell, P.R.B., and Wigger, H.J., "Angiotensin-Converting Enzyme: Effect of Antienzyme Antibody In Vivo," *FEBS Lett.* 63:82-84, North-Holland Publishing Company (1976).
Chackerian, B., et al., "Determinants of autoantibody induction by conjugated papillomavirus virus-like particles," *J. Immunol.* 169 (11) :6120-6, The American Association of Immunologist (Dec. 2002).
Chackerian, B., et al., "Induction of autoantibodies to mouse CCR5 with recombinant papillomavirus particles," *Proc. Natl. Acad. Sci. USA* 96:2373-2378, National Academy of Sciences (1999).
Christlieb, A.R., et al., "Studies on the Role of Angiotensin in Experimental Renovascular Hypertension: an Immunologic Approach," *J. Clin. Invest.* 48:1506-1518, American Society for Clinical Investigation (1969).
Christlieb, A.R., et al., "Blood pressure response and antibody formation in spontaneously hypertensive rats and normal albino rats after immunization against angiotensin II," *Endocrinology* 91(4) :1064-70, The Endocrine Society (1972).
Copy of Office Action for U.S. Appl. No. 10/050,902, Renner, W.A., filed Jan. 18, 2002, Office Action mailed Mar. 1, 2004.
Copy of Office Action for U.S. Appl. No. 10/050,902, Renner, W.A., filed Jan. 18, 2002, Office Action mailed Oct. 15, 2004.
Copy of Office Action for U.S. Appl. No. 10/050,902, Renner, W.A., filed Jan. 18, 2002, Office Action mailed Apr. 29, 2005.
Copy of Office Action for U.S. Appl. No. 10/050,902, Renner, W.A., filed Jan. 18, 2002, Office Action mailed Nov. 17, 2005.
Crook, E.D., "The genetics of human hypertension," *Semin Nephrol* 22(1) :27-34, W.B. Saunders (Jan. 2002).
Downham, M.R., et al., "Evaluation of two carrier protein-angiotensin I conjugate vaccines to assess their future potential to control high blood pressure (hypertension) in man," *Br. J. Clin. Pharmacol.* 56(5) :505-12, Blackwell Publishing Ltd. (Nov. 2003).
Fehr, T., et al., "Role of Repetitive Antigen Patterns for Induction of Antibodies Against Antibodies," *J Exp. Med.* 185:1785-1792, The Rockefeller University Press (1997).
Fehr, T., et al., "T cell-independent type I antibody response against B cell epitopes expressed repetitively on recombinant virus particles," *Proc. Natl. Acad. Sci. USA* 95:9477-9481, National Academy Press (1998).
Folkman, J., "Angiogenesis in cancer, vascular, rheumatoid and other disease," *Nat. Med.* 1:27-31, Nature Publishing Company (1995).
Folkman, J., and Klagsbrun, M., "Angiogenic Factors," *Science* 235:442-447, American Association for the Advancement of Science (1987).

Gardiner, S.M., et al., "Active immunization with angiotensin I peptide analogue vaccines selectively reduces the pressor effects of exogenous angiotensin I in conscious rats," *Br. J. Pharmacol.* 129:1178-1182, Macmillan Publishers Ltd. (Mar. 2000).

Harding, C.V., and Song, R., "Phagocytic Processing of Exogenous Particulate Antigens by Macrophages for Presentation by Class I MHC Molecules," *J. Immunol.* 153:4925-4933, The American Association of Immunologists (1994).

Hui, E. K-W, et al., "Hepatitis B viral core proteins with an N-terminal extension can assemble into core-like particles but cannot be enveloped," *J. Gen. Virol.* 80:2647-2659, Society for General Microbiology (1999).

Ikram, H., and Prince, A.M., "A method for coupling the Hepatitis B surface antigen to aldehyde-fixed erythrocytes for use in passive hemagglutination," *J. Virol. Methods* 2:269-275, Elsevier/North-Holland Biomedical Press (1981).

International Preliminary Examination Report for International Application No. PCT/IB99/01925, European Patent Office, Munich (Aug., 2000).

International Search Report for International Application No. PCT/EP02/11219 mailed on Aug. 14, 2003, European Patent Office, Netherlands.

International Search Report for International Application No. PCT/IB02/00166, mailed Jan. 31, 2003.

International Search Report for International Application No. PCT/IB02/00168 mailed on Nov. 4, 2002.

International Search Report for International Application No. PCT/IB99/01925, European Patent Office, Netherlands (Jun. 2000).

Jagadish, M.N., et al., "Chimeric Potyvirus-Like Particles as Vaccine Carriers," *Intervirology* 39:85-92, S. Karger AG (1996).

Jegerlehner, A., et al., "A molecular assembly system that renders antigens of choice highly repetitive for induction of protective B cell responses," *Vaccine* 20:3104-3112, Elsevier Science, Ltd. (Aug. 2002).

Johnston, C.I., et al., "Biological significance of renin angiotensin immunization," *Circ. Res.* 27:Suppl 2:215-222, Lippincott, Williams & Wilkins (1970).

Kirnbauer, R., "Papillomavirus-Like Particles for Serology and Vaccine Development," *Intervirology* 39:54-61, S. Karger AG (1996).

Klovins, J., et al., "Nucleotide sequence of a ssRNA phage from Acinetobacter: kinship to coliphages," *J. Gen. Virol.* 83:1523-1533, Society for General Microbiology (Jun. 2002).

Koletzki, D., et al., "Mosaic hepatitis B virus core particles allow insertion of extended foreign protein segments," J. Gen. Virol. 78 (Pt 8):2049-53, Society for General Microbiology (1997).

Kovacsovics-Bankowski, M., et al., "Efficient major histocompatibility complex class I presentation of exogenous antigen upon phagocytosis by macrophages," *Proc. Natl. Acad. Sci. USA* 90:4942-4946, National Academy Press (1993).

Kratz, P.A., et al., "Native display of complete foreign protein domains on the surface of hepatitis B virus capsids," *Proc. Natl. Acad. Sci. USA* 96:1915-1920, National Academy of Sciences (1999).

Lechner, F., et al., "Virus-like particles as a modular system for novel vaccines," *Intervirology* 45(4-6):212-7, S. Karger AG Basel (Jul-Dec.2002).

Lo, M., et al., "Antirenin Immunization Versus Angiotensin Converting Enzyme Inhibition in Rats," *Hypertension* 16:80-88, American Heart Association (1990).

Lo-Man, R., et al., "A recombinant virus-like particle system derived from parvovirus as an efficient antigen carrier to elicit a polarized Th1 immune response without adjuvant," *Eur. J. Immunol.* 28:1401-1407, Wiley-VCH Verlag GmbH (1998).

Mancini, G.B., "Emerging concepts: angiotensin-converting enzyme inhibition in coronary artery disease," *Cardiovasc. Drugs. Ther.* 10 Suppl 2:609-12, S. Karger AG Basel (1996).

Michel, J. -B., et al., "Immunologic approaches to blockade of the renin-angiotensin system: A review," *Am. Heart J.* 117:756-767, Mosby (1989).

Michel, J. -B., et al., "Physiological and Immunopathological Consequences of Active Immunization of Spontaneously Hypertensive and Normotensive Rats Against Murine Renin," *Circulation* 81:1899-1910, American Heart Association (1990).

Michel, J.B., et al., "Active immunization against renin in normotensive marmoset," *Proc Natl Acad Sci U S A.* 84(12):4346-50, National Academy Press (1987).

Michel, J.B., et al., "Physiological and immunopathological consequences of active immunization of spontaneously hypertensive and normotensive rats against murine renin," *Circulation* 81 (6):1899-910, Lippincott Williams & Wilkins (1990).

Ni, C. -Z., et al., "Crystal structure of the coat protein from the GA bacteriophage: Model of the unassembled dimer," *Protein Sci.* 5:2485-2493, Cambridge University Press (1996).

Nieland, J.D., et al., "Chimeric Papillomavirus Virus-like Particles Induced a Murine Self-Antigen-Specific Protective and Therapeutic Antitumor Immune Response," *J. Cell. Biochem.* 73:145-152, Wiley-Liss, Inc. (1999).

Oates, H.F., et al., "Plasma renin response to acute blockade of angiotensin II in the anaesthetized rat," *Clin Exp Pharmacol Physiol.* 1 (2):155-60, Blackwell Science Asia (1974).

Oates, H.F., et al., "Renal hypertension in rats immunizied against angiotensin I and angiotensin II," *J. Exp. Med.* 139 (2):239-48, The Rockefeller University Press (1974).

Peeters, J.M., et al., Comparison of four bifunctional reagents for coupling peptides to proteins, *J. Immunol. Methods* 120:133-143, Elsevier Science Publishers B.V. (1989).

Priano, C., et al., "A Complete Plasmid-based Complementation System for RNA Coliphage Qβ: Three Proteins of Bacteriophages Qβ (Group III) and SP (Group IV) can be Interchanged," *J. Mol. Biol.* 249:283-297, Academic Press, Ltd. (1995).

Pumpens, P. and Grens, E., "Hepatitis B core particles as a universal display model: a structure-function basis for development," *FEBS Lett.* 442:1-6, Elsevier Science B.V. on behalf of the Federation of European Biochemical Societies (1999).

Pumpens, P., and Grens, E., "HBV Core Particles as a Carrier for B Cell/T Cell Epitopes," *Intervirology* 44:98-114, S. Karger AG (Aug. 2001).

Pushko, P., et al., "Analysis of RNA phage fr coat protein assembly by insertion, deletion and substitution mutagenesis," *Prot. Eng.* 6:883-891, Oxford University Press (1993).

Quash, G., et al., "The preparation of latex particles with covalently bound polyamines IgG and measles agglutinins and their use in visual agglutination tests," *J. Immunol. Methods* 22:165-174, Elsevier/North-Holland Biomedical Press (1978).

Reade, R., et al., "Immunisation du rat spontanément hypertendu contre l'angiotensine I," *Arch. Mal. Coeur.* 82 (7):1323-8, Bailliere (1989).

Risau, W., "Mechanisms of angiogenesis," *Nature* 386:671-674, Nature Publishing Group (1997).

Rizzoni, D., et al., "Effects of losartan and enalapril on small artery structure in hypertensive rats," *Hypertension* 32 (2):305-10, Lippincott Williams & Wilkins (1998).

Romagnani, S., "The Th1/Th2 paradigm," *Immunol. Today* 18:263-266, Elsevier Science, Ltd. (1997).

Roth, J. -F., "The yeast Ty virus-like particles," *Yeast* 16:785-795, John Wiley & Sons, Ltd. (Jun. 2000).

Roy, P., "Genetically Engineered Particulate Virus-Like Structures and Their Use as Vaccine Delivery Systems," *Intervirology* 39:62-71, S. Karger AG (1996).

Rueda, P., et al., "Minor Displacements in the Insertion Site Provoke Major Differences in the Induction of Antibody Responses by Chimeric Parvovirus-like Particles," *Virology* 263:89-99, Academic Press (1999).

Sapp, M., et al., "Synthesis, Properties and Applications of Papillomavirus-Like Particles," *Intervirology* 39:49-53, S. Karger AG (1996).

Schödel, F., et al., "Hepatitis B Virus Core and e Antigen: Immune Recognition and Use as a Vaccine Carrier Moiety," *Intervirology* 39:104-110, S. Karger AG (1996).

Soffer, R.L., and El-Dorry, H.A., "Angiotensin-converting enzyme: immunologic structural, and developmental aspects," *Federation Proc. 42*:2735-2739, Federation of American Societies for Experimental Biology (1983).

Smits, J., et al., "Anti-hypertensive properties of angiotensin immunotherapeutic in spontaneous hypertension in rats," *FASEB 13*:A483, Federation for American Societies for Experimental Biology (1999).

Stoll, E., et al., "Revised Amino Acid Sequence of Qα Coat Protein between Positions 1 and 60," *J. Biol. Chem. 252*:990-993, American Society for Biochemistry and Molecular Biology (1977).

Ulrich, R., et al., "Chimaera and Its Modern Virus-Like Descendants," *Intervirology 39*:126-132, S. Karger AG (1996).

Ulrich, R., et al., "Core particles of hepatitis B virus as carrier for foreign epitopes," *Adv. Virus Res. 50*:141-182, Academic Press (1998).

Vasiljeva, I., et al., "Mosaic Qβ coats as a new presentation model," *FEBS Lett. 431*:7-11, Federation of European Biochemical Societies (1998).

Warnes, A., et al., "Expression of the measles virus nucleoprotein gene in *Escherichia coli* and assembly of nucleocapsid-like structures," *Gene 160*:173-178, Elsevier Science B.V. (1995).

Witherell, G.W., and Uhlenbeck, O.C., "Specific RNA Binding by Qβ Coat Protein," *Biochemistry 28*:71-76, American Chemical Society (1989).

Wynne, S.A., et al., "The Crystal Structure of the Human Hepatitis B Virus Capsid," *Mol. Cell 3*:771-780, Cell Press (1999).

Yuan, T-T., et al., "Subtype-Independent Immature Secretion and Subtype-Dependent Replication Deficiency of a Highly Frequent, Naturally Occurring Mutation of Human Hepatitis B Virus Core Antigen," *J. Virol. 73*:10122-10128, American Society for Microbiology (1999).

Zhou, S., and Standring, D.N., "Cys Residues of the Hepatitis B Virus Capsid Protein Are Not Essential for the Assembly of Viral Core Particles but Can Influence Their Stability," *J. Virol. 66*:5393-5398, American Society for Microbiology (1992).

Zuercher, A.W., et al., "Oral anti-IgE immunization with epitope-displaying phage," *Eur. J. Immunol. 30*:128-135, Wiley-Vch Verlag GmbH (Jan. 2000).

* cited by examiner

FIGURE 4
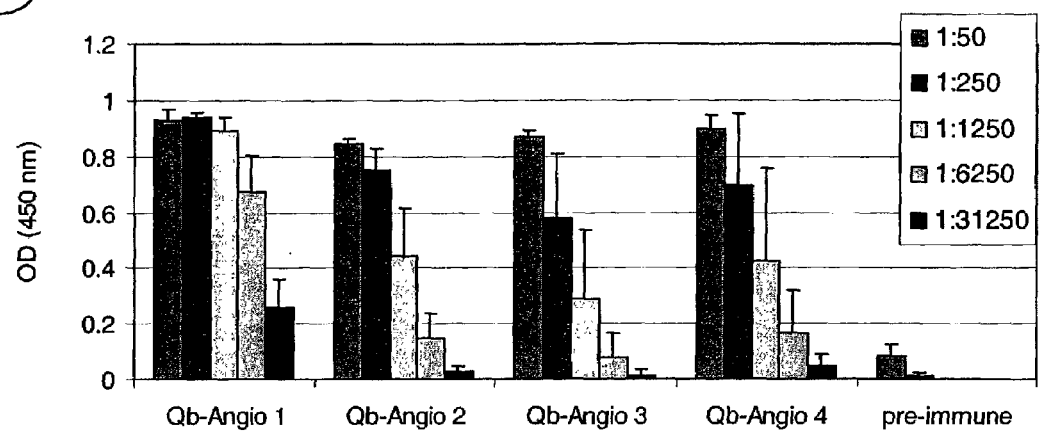
A) IgG antibodies specific for CGGDRVYIHPF ("Angio 1")
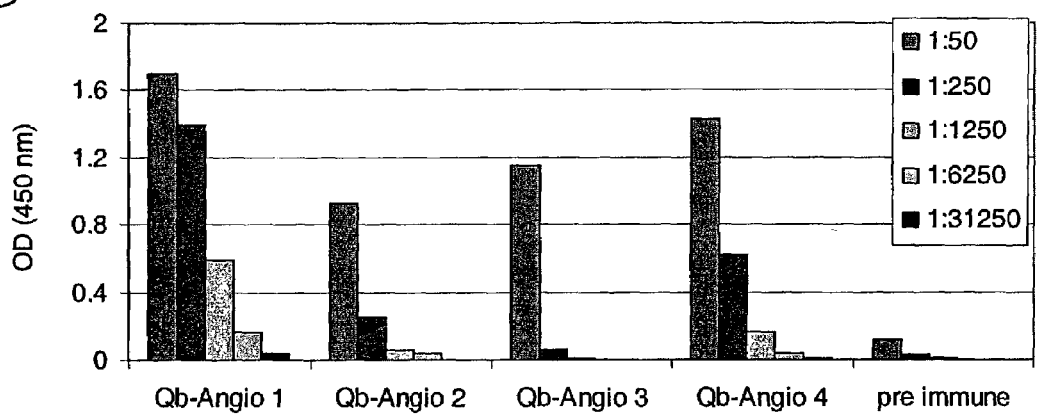
B) IgG antibodies specific for angiotensin II FIGURE 2
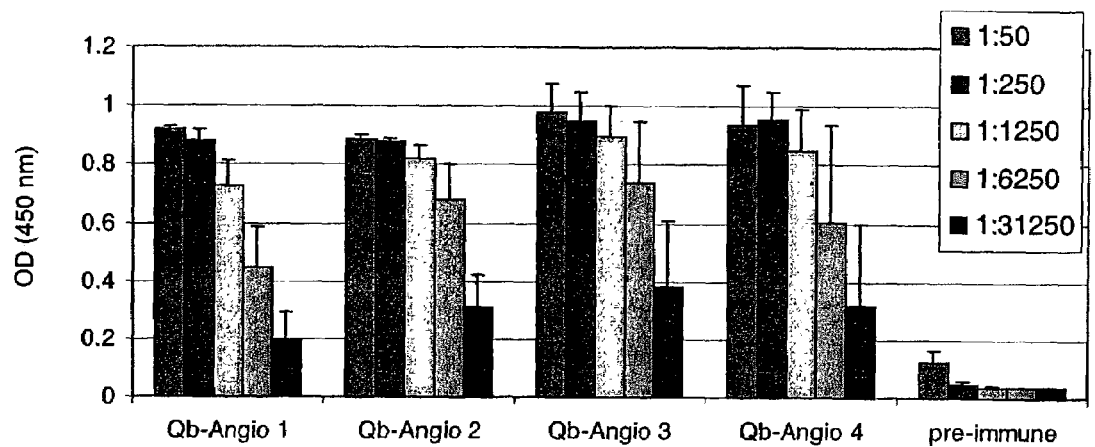
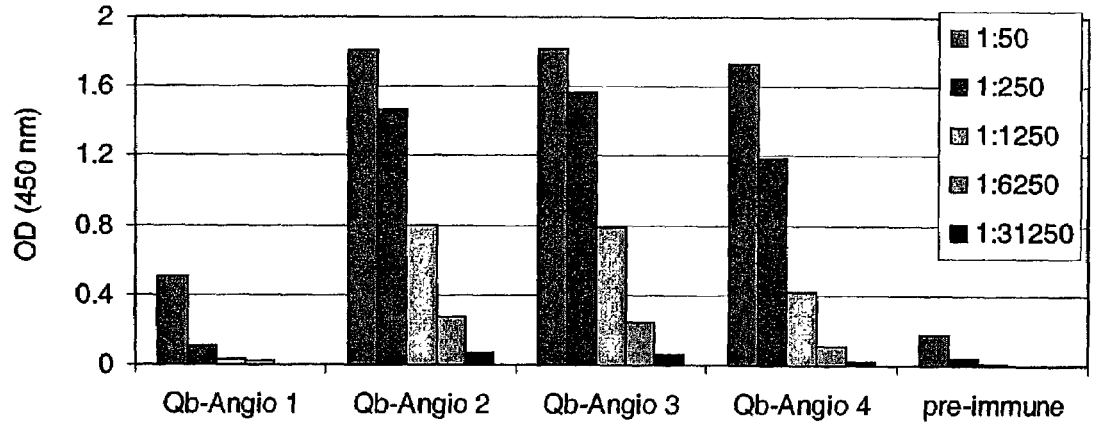

FIGURE 3
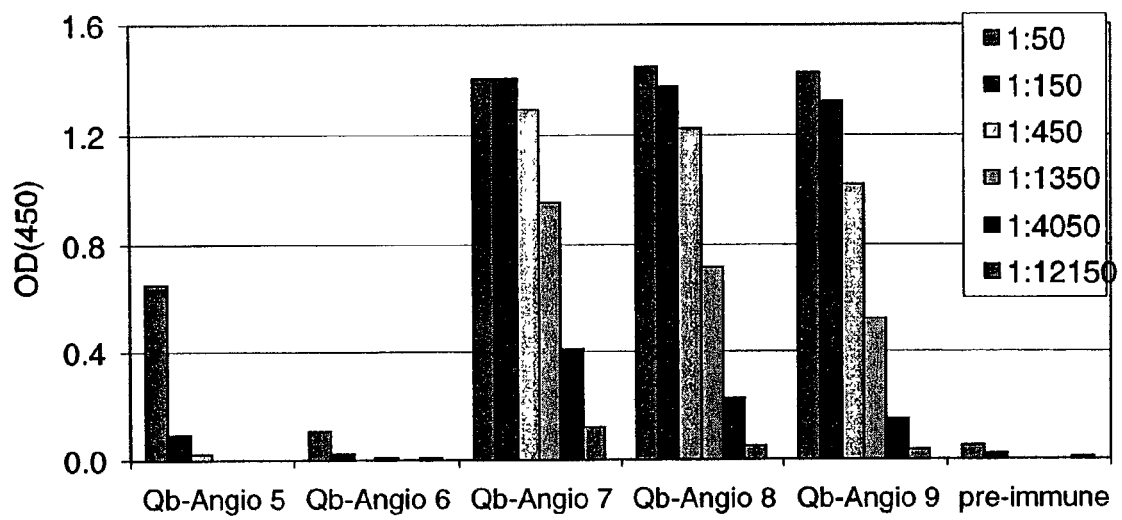
A) IgG antibodies specific for CGGDRVYIHPF ("Angio 1")
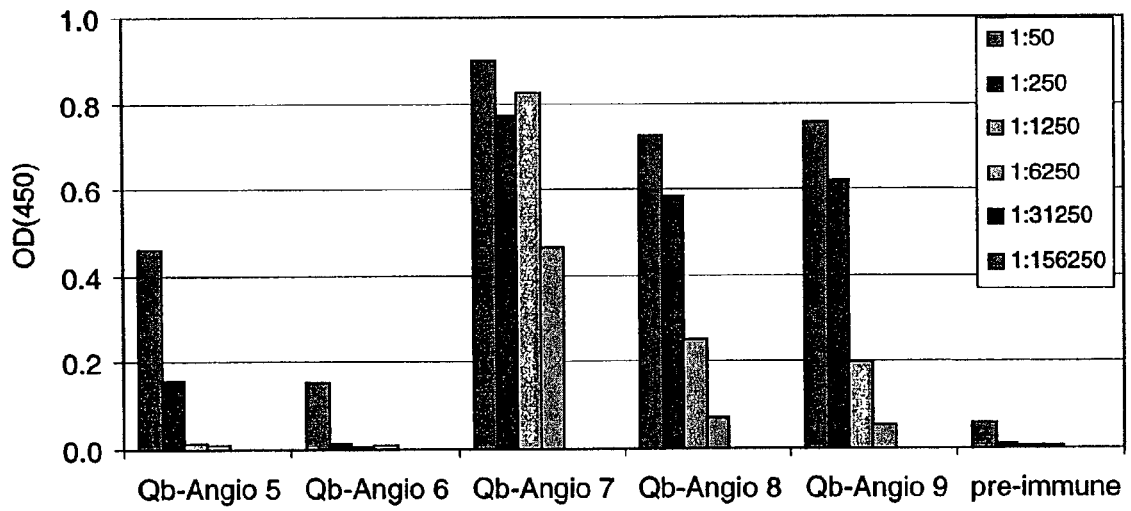
B) IgG antibodies specific for angiotensin II FIGURE 4
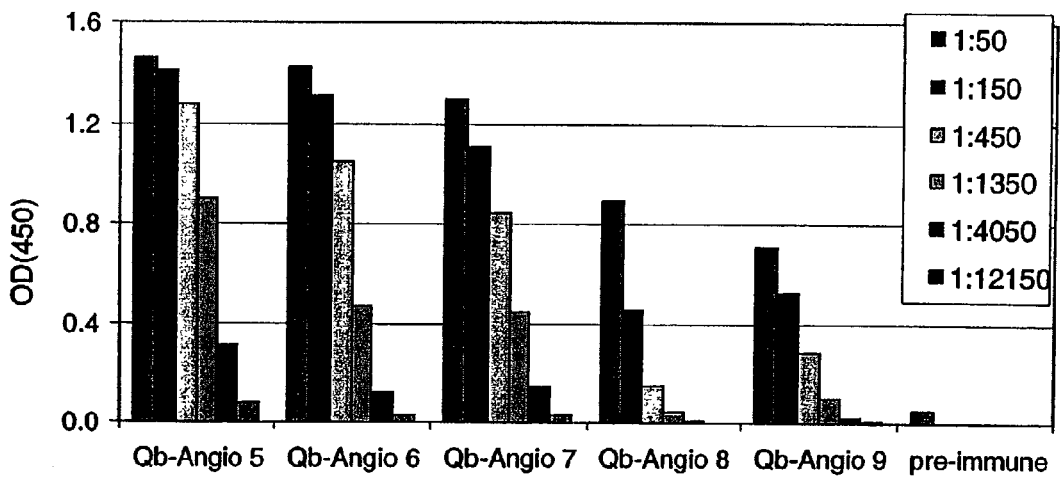
A) IgG antibodies specific for CGGDRVYIHPFHL ("Angio 2")
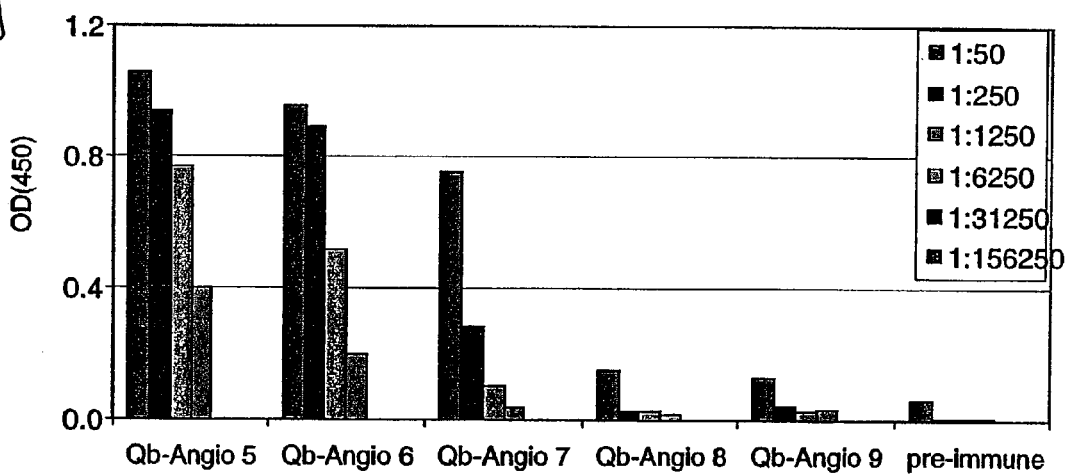
B) IgG antibodies specific for angiotensin I sional Application Nos. 60/326,998, filed Oct. 5, 2001; 60/331,045, filed Nov. 7, 2001; and 60/396,637, filed Jul. 19, 2002. The present application is also a continuation-in-part of U.S. Application Ser. No. 10/050,902, filed Jan. 18, 2002; and International Application No. PCT/IB02/00166, filed Jan. 21, 2002, which designates the United States of America and which was published in English under PCT Article 21(2) as WO 02/056905 on Jul. 25, 2002. The disclosures of all of the above-referenced applications are incorporated by reference herein in their entireties.

ANGIOTENSIN PEPTIDE-CARRIER CONJUGATES AND USES THEREOF

CROSS-REFERENCE TO RELATED APPLICATIONS

The present application claims the benefit of U.S. Provisional Application Nos. 60/326,998, filed Oct. 5, 2001; 60/331,045, filed Nov. 7, 2001; and 60/396,637, filed Jul. 19, 2002. The present application is also a continuation-in-part of U.S. Application Ser. No. 10/050,902, filed Jan. 18, 2002; and International Application No. PCT/IB02/00166, filed Jan. 21, 2002, which designates the United States of America and which was published in English under PCT Article 21(2) as WO 02/056905 on Jul. 25, 2002. The disclosures of all of the above-referenced applications are incorporated by reference herein in their entireties.

BACKGROUND OF THE INVENTION

1. Field of the Invention

The present invention is in the fields of medicine, public health, immunology, molecular biology and virology.

2. Related Art

The arterial blood pressure of mammals is mostly controlled by a biochemical cascade known as the renin-angiotensin-System (RAS). It is initiated by the release of renin from the epitheloid cells of the juxtaglomerular apparatus of the kidney following a fall in arterial blood pressure. Renin enzymatically cleaves the peptide angiotensinogen (amino acid sequence: Asp-Arg-Val-Tyr-Ile-His-Pro-Phe-His-Leu-Val-Ile-His-Asn, SEQ ID NO: 15) which is secreted into the serum by the liver. This cleavage leads to the formation of the decapeptide angiotensin I (amino acid sequence: Asp-Arg-Val-Tyr-Ile-His-Pro-Phe-His-Leu, SEQ ID NO: 16). The angiotensin converting enzyme (ACE) which is present in the endothelium of the lungs cleaves within seconds the two C-terminal amino acids of ATI to give rise to angiotensin II (amino acid sequence: Asp-Arg-Val-Tyr-Ile-His-Pro-Phe, SEQ ID NO: 17). Whereas angiotensin I is very short lived within the body and has no or only mild vasoconstrictor activity, angiotensin II has a profound effect on the circulatory system as well as on the endocrine system. Elevated levels of RAS-activated angiotensin II cause vasoconstriction, renal retention of salt and water, both of which contribute to increased arterial pressure (hypertension) which can lead to cardiovascular damage. Possible clinical manifestations of hypertension are stroke, infarction, congestive heart failure, kidney failure or retinal hemorrhage.

According to the U.S. Centers for Disease Control and Prevention (CDC), congestive heart failure is a major chronic disease for older adults, accounting for about 260,000 deaths a year in the US. In 1995, $3.4 billion was paid by Medicare for heart failure. Although drugs are available for the treatment of hypertension, control of hypertension is only obtained in around half of the treated hypertensive patients. This is partially due to non-compliance of the patient or ineffectiveness of the used drugs.

Current treatment of hypertension includes intervention of the RAS system using small organic molecules. Main targets are renin, ACE and the receptors for angiotensin II. ACE inhibitors include lisinopril®, captopril® and enalapril®, however, these drugs have not been entirely successful. Firstly they do not seem to entirely block ACE activity and secondly the generation by ACE of other biologically active peptides, including bradykinin, is also affected, which is undesirable. These drugs can induce side effects such as dry cough and a first dose hypotensive effect with dizziness and possible fainting. Angiotensin II receptor antagonists include losartan®, valsartan® and isbesaftan® which act specifically on the AT1 angiotensin receptor; they therefore block the dominant vasoconstrictor effects of angiotensin II, and are better tolerated but do not affect other actions of the angiotensin hormones. However, angiotensin II receptor antagonists as well as ACE inhibitors need to be taken on a regular basis, often for long periods, such as for the majority of adult life which at least partially explains poor patient compliance. Therefore, there is a clear need for therapies of hypertension which are effective, well tolerated and connected with a high compliance of the patient.

A potential approach in treating or preventing diseases or disorders associated with the activity of a hormone is to neutralize the effects of the hormone within the patient by immunotherapy, i.e., by immunizing the patient against the hormone or enzymes which are involved in the generation of the hormone such that the activity of the hormone is neutralized or its levels are reduced by specific anti-hormone or anti-enzyme antibodies. Such antibodies may be exogenously administered in passive immunization or they may be generated in situ by active immunization using an immunogen based on the hormone or the relating enzyme.

The feasibility of vaccination against components of the RAS to modulate hypertension has been shown in animal models (for a review, see Michel, *Am. Heart J.* 117:756 (1989)). Vaccination against renin was effective in reducing blood pressure, however the animals suffered from autoimmune nephritis. (Michel et al., *Circulation* 81:1899 (1990); Lo et al., *Hypertension* 16:80 (1990)). Data on active immunization against homologous ACE is very limited. One report describes the vaccination of rabbits but only 1 out of 50 animals made detectable anti-ACE antibodies (Soffer, *Fed. Proc.* 42:2735 (1983)). Passive transfer of immune serum against ACE can decrease blood pressure in rabbits but leads to an immunoallergic response with pulmonary edema, possibly because ACE is expressed in a membrane-bound form in the lung (Cadwell, *FEBS Lett.* 63:82 (1976)). No reports are available on active immunization against angiotensinogen, however several studies explored the feasibility of vaccination against angiotensin I and angiotensin II. Two studies reported a blood pressure effect (Christlieb, *J. Clin. Invest.* 48:1506 (1969); Gardiner, Br. *J. Pharmacol.* 129:1178 (2000)) in vaccinated animals and no autoimmunity was noted. However the majority of vaccination studies with angiotensin peptides were negative, possibly because the induced titers against angiotensin peptides were too low or because the specificity of the induced antibodies was not optimal. It is likely that a vaccine which only targets angiotensin II does not have the same effect on the RAS as a vaccine which induces antibodies against angiotensin II as well as angiotensin I and possibly also the precursor angiotensinogen.

WO 98/58952 describes the treatment with a conjugate containing an angiotensin I conjugated to tetanus toxoid, which leads to the induction of angiotensin-specific antibodies in rats if applied in conjunction with an adjuvant such as aluminium hydroxide. Adjuvants are often toxic or at least irritating. The only adjuvants allowed for human use to date are mineral salts (aluminum hydroxide, aluminium phosphate, calcium phosphate) and virosomes. The adjuvant most frequently used in humans is aluminum hydroxide (Alum). Although it is considered as safe, it remains in the body for an extended period of time forming a depot. Consequences of such depot-formation are still poorly understood, therefore attempts should be made to avoid Alum in future vaccines without loosing their immunogenicity.

Therefore, there remains a need in the art to provide conjugates leading to the induction of high antibody titers even in the absence of adjuvants.

SUMMARY OF THE INVENTION

We have now developed potent immunogens for the induction of antibodies specific for angiotensinogen, angiotensin I or angiotensin II (referred to herein collectively as "angiotensin peptides"), which are effective even without the use of adjuvants and which allow the development of antibodies in vivo that specifically target one or more angiotensin peptides, such as angotensinogen, angiotensin I or angiotensin II. The immunogens consist of angiotensin peptide moieties which are bound to virus-like particles (VLP). This results in a highly immunogenic repetitive antigen array which is able to stimulate antibody formation even without the use of adjuvants. Depending on the amino acid sequence of the angiotensin peptide moieties used, high antibody titers are induced, and, moreover, can be specifically induced against the N- or C-terminal ends of angiotensinogen, angiotensin I or angiotensin II. This allows the specific targeting of only one species of angiotensin peptides or a combination thereof. The immunogens of the present invention thus can be used in an immunotherapeutic approach to combat conditions associated with elevated levels of angiotensin II produced by the RAS.

Without intending to be limited to any particular theory of operation or mechanism, the conjugates and conjugates of the invention can induce antibodies which bind to more than one angiotensin peptide species, thereby blocking all relevant species of angiotensin at the same time. Alternatively, the induced antibodies could specifically to the C-terminus of angiotensinogen, angiotensin I or angiotensin II. Under these conditions, the induced antibodies will block activation of angiotensinogen or angiotensin I by renin or ACE, respectively. Nevertheless, proteases different from ACE or renin, such as endopeptidases and aminopeptidases, can degrade angiotensinogen, angiotensin I or angiotensin II from the N-terminus thus preventing the accumulation of antibody-bound intact angiotensinogen, angiotensin I or angiotensin II.

Thus, by the invention, immunogens are provided that comprise one or more angiotensin peptides or peptide moieties, or derivatives thereof, bound to one or more core particles, preferably one or more virus-like particles (VLPs), to form conjugates having the structure of ordered and repetitive arrays. Core particles containing a first attachment site, and angiotensin peptides or derivatives thereof containing a second attachment site, are associated through said first and second attachment sites to form such ordered and repetitive arrays. The interaction between the first and second sites may be direct, or may involve at least one other molecule, e.g., a linker.

In one embodiment, the first attachment site naturally occurs in the core particle. Alternatively, the first attachment site is added by chemical coupling or by recombinant techniques. Preferred first attachment sites comprise amino groups, carboxyl groups or sulfhydryl groups. Preferred amino acids comprising a first attachment site are selected from lysine, arginine, cysteine, aspartate, glutamate tyrosine and histidine. Particularly preferred are lysine residues.

Suitable second attachment sites on the angiotensin peptides or derivatives thereof are amine, amide, carboxyl and sulfhydryl groups. There is a wide range of compounds that have been developed to enable crosslinking of peptides/proteins or conjugation of protein to derivatized molecules, by forming a covalent bond with a reactive group of a protein molecule of the core particle.

Core particles with a first attachment site of the invention include any particle suitable for the formation of ordered repetitive arrays. In some embodiments such core particles include virus-like particles (VLPs), bacteriophage, bacteriophage virus like particles, pili, and the like. In certain embodiments these are HbcAg VLPs, bacteriophage VLP and type I pili. The invention also provides variant forms of the core particles that remain able to form ordered repetitive structure. Variant forms include recombinant and natural forms, and mutant forms of core particles. In certain embodiments, the mutant forms of the core particle include those where the type of first attachment site, or number of said sites, differ from the parent. Alteration of the number of lysine residues on the core particle are particularly preferred.

In certain embodiments, conjugates of the invention comprise angiotensin peptide moieties which are chemically coupled to virus-like particles (VLP). This results in a highly immunogenic repetitive antigen array which is able to stimulate antibody formation even without the use of adjuvants. Depending on the amino acid sequence of the angiotensin peptide moieties used, high antibody titers are induced, and, moreover, can be specifically induced against the N- or C-terminal ends of angiotensinogen, angiotensin I or angiotensin II. This allows to specifically target only one species of angiotensin peptides or a combination thereof. The inventive immunogens can be used in an immunotherapeutic approach to combat conditions associated with elevated levels of angiotensin II produced by the RAS.

The present invention thus provides conjugates comprising a core particle and one or more angiotensin peptides or angiotensin peptide moieties, suitable for use in inducing immune responses. The invention also provides conjugates comprising such conjugates of the invention and one or more additional components such as one or more excipients or carriers, suitably one or more pharmaceutically acceptable excipients or carriers. Conjugates and conjugates of the invention include vaccine conjugates or conjugates, with or without additional pharmaceutically acceptable excipients or adjuvants. For example, the present invention also provides vaccine conjugates comprising an immunologically effective amount of the one or more of the conjugates or conjugates of the present invention together with a pharmaceutically acceptable diluent, carrier or excipient. In a further embodiment, the vaccine further comprises at least one adjuvant, such as Alum or incomplete Freund's adjuvant. The invention also provides methods of immunizing and/or treating an animal, preferably a mammal such as a human, comprising administering to the animal an immunologically effective amount of conjugates, conjugates, or vaccines of the invention thereby inducing an immune response against the conjugates or conjugates. Animals may be suitably immunized with the conjugates or conjugates of the invention by any art-known route of administration, including but not limited to subcutaneously, intramuscularly, intranasally, intradermally, intravenously, transdermally, transmucosally, orally, or directly into a lymph node. Intranasal immunization is a particularly suitable route; this type of administration leads not only to high antibody titers encompassing IgA as indicated in the examples but also, by avoiding painful immunization procedures (e.g intramuscular) is more acceptible to the patient and leads to improved compliance.

Conjugates and conjugates of the invention induce immune responses, including the production of antibodies. Therefore, in another embodiment, the invention provides methods of producing antibodies against one or more angiotensin peptides or angiotensin peptide moieties. Such antibodies of the invention are useful in treatment or prevention of physical disorders associated with the RAS, and for the detection of angiotensin peptides or angiotensin peptide moieties, for example in the methods of diagnosing physical disorders associated with the presence of one or more components of the RAS in the tissues or circulation of an animal.

In a related embodiment, the invention is useful for the prevention or treatment of diseases, disorders or conditions associated with the RAS, including but not limited to stroke, infarction, congestive heart failure, kidney failure, retinal hemorrhage and the like. Immunization with the conjugates or conjugates of the invention results in an immune response against the one or more angiotensin peptides or angiotensin peptide moieties, such that immune molecules, particularly antibodies, bind the angiotensin peptides or angiotensin peptide moieties. Passive transfer of antibodies is also useful for the treatment and prevention of disorders associated with the RAS.

We have found that conjugates of angiotensin peptides or angiotensin peptide moieties attached to virus-like particles (VLPs) induce high angiotensin-specific IgG antibodies. The present invention therefore provides a therapeutic for physical disorders associated with the RAS, which is based, in a very preferred embodiment, on a ordered and repetitive VLP-angiotensin peptide/moiety conjugate. This therapeutic is able to induce high titers of anti-angiotensin antibodies in a vaccinated animal. High antibody titers are induced even in the absence of adjuvants and encompass not only IgG but also IgA subtypes. Furthermore, this therapeutic surprisingly is not associated with induction of potentially pathologic immune responses such as inflammation. Therapeutic conjugates of the invention comprise at least one angiotensin peptide or angiotensin peptide moiety and a VLP, preferably a VLP of a RNA-phage, or at least angiotensin peptide or angiotensin peptide moiety and an alternative core particle such as HbcAg or pili.

Other embodiments of the present invention will be apparent to one of ordinary skill in light of what is known in the art, the following drawings and description of the invention, and the claims.

BRIEF DESCRIPTION OF THE DRAWINGS/FIGURES

FIG. 1 is an ELISA analysis of IgG antibodies specific for the Angio 1 peptide and angotensin II in sera of mice immunized with Angio 1, Angio 2, Angio 3 or Angio 4 peptides coupled to Qβ capsid protein.

FIG. 2 is an ELISA analysis of IgG antibodies specific for the Angio 2 peptide and angotensin I in sera of mice immunized with Angio 1, Angio 2, Angio 3 or Angio 4 peptides coupled to Qβ capsid protein.

FIG. 3 is an ELISA analysis of IgG antibodies specific for the Angio 1 peptide and angotensin II in sera of mice immunized with Angio 5, Angio 6, Angio 7, Angio 8 or Angio 9 peptides coupled to Qβ capsid protein.

FIG. 4 is an ELISA analysis of IgG antibodies specific for the Angio 2 peptide and angotensin I in sera of mice immunized with Angio 5, Angio 6, Angio 7, Angio 8 or Angio 9 peptides coupled to Qβ capsid protein.

DETAILED DESCRIPTION OF THE INVENTION

Definitions

In the description that follows, a number of terms used in the field of molecular biology, immunology and medicine are extensively utilized. In order to provide a clearer and consistent understanding of the specification and claims, including the scope to be given such terms, the following non-limiting definitions are provided.

Active immunization: As used herein, the term "active immunization" refers to the induction of an immune response in an individual, typically an animal, elicited by the administration of an immunogen, vaccine, antigen or angiotensin peptide-carrier conjugate. By contrast, passive immunization refers to the conferral of immunity in an individual by the transfer of immune molecules or cells into said individual.

Alphavirus: As used herein, the term "alphavirus" refers to any of the RNA viruses included within the genus Alphavirus. Descriptions of the members of this genus are contained in Strauss and Strauss, *Microbiol. Rev.*, 58:491–562 (1994). Examples of alphaviruses include Aura virus, Bebaru virus, Cabassou virus, Chikungunya virus, Easter equine encephalomyelitis virus, Fort morgan virus, Getah virus, Kyzylagach virus, Mayoaro virus, Middleburg virus, Mucambo virus, Ndumu virus, Pixuna virus, Tonate virus, Triniti virus, Una virus, Western equine encephalomyelitis virus, Whataroa virus, Sindbis virus (SIN), Semliki forest virus (SFV), Venezuelan equine encephalomyelitis virus (VEE), and Ross River virus.

Amino acid linker: An "amino acid linker," or also just termed "linker" within this specification, as used herein, either associates the antigen or antigenic determinant with the second attachment site, or more preferably, already comprises or contains the second attachment site, typically—but not necessarily—as one amino acid residue, preferably as a cysteine residue. The term "amino acid linker" as used herein, however, does not intend to imply that such an amino acid linker consists exclusively of amino acid residues, even if an amino acid linker consisting of amino acid residues is a preferred embodiment of the present invention. The amino acid residues of the amino acid linker are, preferably, composed of naturally occuring amino acids or unnatural amino acids known in the art, all-L or all-D or mixtures thereof. However, an amino acid linker comprising a molecule with a sulfhydryl group or cysteine residue is also encompassed within the invention. Such a molecule comprise preferably a C1–C6 alkyl-, cycloalkyl (C5,C6), aryl or heteroaryl moiety. However, in addition to an amino acid linker, a linker comprising preferably a C1–C6 alkyl-, cycloalkyl (C5,C6), aryl- or heteroaryl-moiety and devoid of any amino acid(s) shall also be encompassed within the scope of the invention. Association between the antigen or antigenic determinant or optionally the second attachment site and the amino acid linker is preferably by way of at least one covalent bond, more preferably by way of at least one peptide bond.

Angiotensin Peptide Moiety: As used herein, the term "angiotensin peptide moiety" refers to any moiety, whether or not the moiety has the biological activity of a native angiotensin in vivo (e.g., native hormone activity at the receptors, including both angiotensins I and II), which is capable of acting as an immunomimic of native angiotensin peptides (i.e., which immunologically mimics angiotensin so as to generate antibodies which bind to native angiotensin peptides). Thus, such a moiety may conveniently comprise an angiotensin peptide, preferably angiotensinogen, angiotensin I (a decapeptide of formula Asp-Arg-Val-Tyr-Ile-His-Pro-Phe-His-Leu, SEQ ID NO: 16) or angiotensin II (an octapeptide of formula Asp-Arg-Val-Tyr-Ile-His-Pro-Phe, SEQ ID NO: 17), or a functionally equivalent variant thereof. Hence, "angiotensin peptide moiety" encompasses "angiotensin peptide" as that term is defined herein. Such functionally equivalent variants may include modifications of the angiotensin I or II sequence by single or multiple amino acid substitution, addition or deletion and also sequences where the amino acid residues are chemically modified, but which nonetheless retain angiotensin immunogenic activity. Such functionally (or immunologically) equivalent variants may occur as natural biological variations, or they may be prepared using known and standard techniques for example by chemical synthesis or modification, mutagenesis, e.g., site-directed or random mutagenesis, etc. For purposes of this definition, a key feature as regards the modification is that the angiotensin peptide retains the ability to act as immunomimic of native angiotensin. Thus for example, an amino acid may be replaced by another which preserves the physicochemical character of the angiotensin peptide or its epitope(s), e.g. in terms of charge density, hydrophilicity/hydrophobicity, size and configuration and hence preserve the immunological structure. "Addition" variants may include N- or C-terminal fusions as well as intrasequence insertion of single or multiple amino acids. Deletions may be intrasequence or may be truncations from the N- or C-termini. Preferred deletion mutants are those that allow induction of N- or preferably C-terminal antibodies. Such antibodies may prevent generation of active angiotensin II but still allow for degradation of antibody-bound angiotensinogen, angiotensin I or angiotensin II.

Angiotensin Peptide: As used herein, the term "angiotensin peptide" includes all, preferably native, angiotensin peptides and their functionally equivalent variants. Hence, "angiotensin peptide" can be considered a subset of "angiotensin peptide moiety" as defined herein. As a practical matter, whether a given variant of an angiotensin peptide (or angiotensin peptide moiety) is "functionally equivalent" to a, preferably native, angiotensin peptide may be determined by a variety of assay methods for determining the biological activity of an angiotensin peptide. Certain of these assay methods are described herein, and others will be readily familiar to one of ordinary skill in the art.

Antibody: As used herein, the term "antibody" refers to molecules which are capable of binding an epitope or antigenic determinant. The term is meant to include whole antibodies and antigen-binding fragments thereof, including single-chain antibodies. Such antibodies include human antigen binding antibody fragments and include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. The antibodies can be from any animal origin including birds and mammals. Preferably, the antibodies are mammalian e.g. human, murine, rabbit, goat, guinea pig, camel, horse and the like, or other suitable animals e.g. chicken. As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described, for example, in U.S. Pat. No. 5,939,598, the disclosure of which is incorporated herein by reference in its entirety.

Antigen: As used herein, the term "antigen" refers to a molecule capable of being bound by an antibody or a T cell receptor (TCR) if presented by MHC molecules. The term "antigen", as used herein, also encompasses T-cell epitopes. A T-cell epitope is recognized by a T-cell receptor in the context of a MHC class I, present on all cells of the body except erythrocytes, or class II, present on immune cells and in particular antigen presenting cells. This recognition event leads to activation of T-cells and subsequent effector mechanisms such as proliferation of the T-cells, cytokine secretion, perforin secretion etc. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a $T_H$ cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

Antigenic determinant: As used herein, the term "antigenic determinant" is meant to refer to that portion of an antigen that is specifically recognized by either B- or T-lymphocytes. B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors. An antigenic determinant contains one or more epitopes. Allergens also serve as antigens in vertebrate animals.

Association: As used herein, the term "association" as it applies to the first and second attachment sites, refers to the binding of the first and second attachment sites that is preferably by way of at least one non-peptide bond. The nature of the association may be covalent, ionic, hydrophobic, polar or any combination thereof, preferably the nature of the association is covalent.

Attachment Site, First: As used herein, the phrase "first attachment site" refers to an element of the core particle being of non-natural or natural origin, to which the second attachment site located on the antigen or antigenic determinant may associate. The first attachment site may be a protein, a polypeptide, an amino acid, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. The first attachment site is located, typically and preferably on the surface, of the core particle such as, preferably the virus-like particle. Multiple first attachment sites are present on the surface of the core and virus-like particle, respectively, typically in a repetitive configuration.

Attachment Site, Second: As used herein, the phrase "second attachment site" refers to an element associated with the antigen or antigenic determinant to which the first attachment site located on the surface of the core particle and virus-like particle, respectively, may associate. The second attachment site of the antigen or antigenic determinant may be a protein, a polypeptide, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. At least one second attachment site is present on the antigen or antigenic determinant. The term "antigen or antigenic determinant with at least one second attachment site" refers, therefore, to an antigen or antigenic construct comprising at least the antigen or antigenic determinant and the second attachment site. However, in particular for a second attachment site, which is of non-natural origin, i.e. not naturally occurring within the antigen or antigenic determinant, these antigen or antigenic constructs comprise an "amino acid linker".

Bound: As used herein, the term "bound" refers to binding or attachment that may be covalent, e.g., by chemically coupling, or non-covalent, e.g., ionic interactions, hydrophobic interactions, hydrogen bonds, etc. Covalent bonds can be, for example, ester, ether, phosphoester, amide, peptide, imide, carbon-sulfur bonds, carbon-phosphorus bonds, and the like. The term "bound" is broader than and includes terms such as "coupled," "fused" and "attached."

Coat protein(s): As used herein, the term "coat protein(s)" refers to the protein(s) of a bacteriophage or a RNA-phage capable of being incorporated within the capsid assembly of the bacteriophage or the RNA-phage. However, when referring to the specific gene product of the coat protein gene of RNA-phages the term "CP" is used. For example, the specific gene product of the coat protein gene of RNA-phage Qβ is referred to as "Qβ CP", whereas the "coat proteins" of bacteriophage Qβ comprise the "Qβ CP" as well as the A1 protein. The capsid of Bacteriophage Qβ is composed mainly of the Qβ CP, with a minor content of the A1 protein. Likewise, the VLP Qβ coat protein contains mainly Qβ CP, with a minor content of A1 protein.

Core particle: As used herein, the term "core particle" refers to a rigid structure with an inherent repetitive organization. A core particle as used herein may be the product of a synthetic process or the product of a biological process.

Effective Amount: As used herein, the term "effective amount" refers to an amount necessary or sufficient to realize a desired biologic effect. An effective amount of the composition would be the amount that achieves this selected result, and such an amount could be determined as a matter of routine by a person skilled in the art. For example, an effective amount for treating an immune system deficiency could be that amount necessary to cause activation of the immune system, resulting in the development of an antigen specific immune response upon exposure to antigen. The term is also synonymous with "sufficient amount."

The effective amount for any particular application can vary depending on such factors as the disease or condition being treated, the particular composition being administered, the size of the subject, and/or the severity of the disease or condition. One of ordinary skill in the art can empirically determine the effective amount of a particular composition of the present invention without necessitating undue experimentation.

Epitope: As used herein, the term "epitope" refers to basic element or smallest unit of recognition by an individual antibody or T-cell receptor, and thus the particular domain, region or molecular structure to which said antibody or T-cell receptor binds. An antigen may consist of numerous epitopes while a hapten, typically, may possess few epitopes.

Fusion: As used herein, the term "fusion" refers to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini.

Heterologous sequence: As used herein, the term "heterologous sequence" refers to a second sequence of nucleic acid or protein that is not normally found with said nucleic acid or protein and is, usually, artificially added to the sequence in order to confer particular properties. In one example, heterologous amino acids may be added to recombinant capsid proteins for the purposes of purification of the protein, or to serve as a first attachment site.

Immune response: As used herein, the term "immune response" refers to any action by the immune system of an individual that is directed against a molecule or compound, such as an antigen. In mammals, the immune response includes both the activities of cells and the production of soluble molecules such as cytokines and antibodies. The term thus includes a humoral immune response and/or cellular immune response leading to the activation or proliferation of B- and/or T-lymphocytes. In some instances, however, the immune responses may be of low intensity and become detectable only when using at least one substance in accordance with the invention. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier in the presence or absence of an adjuvant.

Immune Deviation: As used herein, the term immune deviation refers to the stimulation of an immune response that is of a different nature to a preexisting immune response. For example, an individual possessing a $T_H2$ immune response against an allergen such that IgE antibodies are produced upon exposure to the allergen may be induced, by embodiments of the present invention, to produce a $T_H1$ immune response against the allergen. Such $T_H1$ response will counteract the allergy inducing $T_H2$ response and so alleviate allergic disease.

Immunotherapeutic: As used herein, the term "immunotherapeutic" refers to a conjugate for the treatment of diseases, disorders or conditions. More specifically; the term is used to refer to a method of treatment wherein a beneficial immune response is generated by vaccination.

Immunologically effective amount: As used herein, the term "Immunologically effective amount" refers to an amount of a conjugate sufficient to induce an immune response in an individual when introduced into that individual. The amount of a conjugate necessary to be immunologically effective varies according many factors including to the conjugate, the presence of other components in the conjugate (e.g. adjuvants), the antigen, the route of immunization, the individual, the prior immune or physiologic state etc.

Individual: As used herein, the term "individual" refers to multicellular organisms and includes both plants and animals. Preferred multicellular organisms are animals, more preferred are vertebrates, even more preferred are mammals, and most preferred are humans.

Isolated: As used herein, when the term "isolated" is used in reference to a molecule, the term means that the molecule has been removed from its native environment. For example, a polynucleotide or a polypeptide naturally present in a living animal is not "isolated," but the same polynucleotide or polypeptide separated from the coexisting materials of its natural state is "isolated." Further, recombinant DNA molecules contained in a vector are considered isolated for the purposes of the present invention. Isolated RNA molecules include in vivo or in vitro RNA replication products of DNA and RNA molecules. Isolated nucleic acid molecules further include synthetically produced molecules. Additionally, vector molecules contained in recombinant host cells are also isolated. Thus, not all "isolated" molecules need be "purified."

Immunotherapeutic: As used herein, the term "immunotherapeutic" is a conjugate that comprises immune molecules and/or elicits an immune response for the treatment of diseases or disorders.

Individual: As used herein, the term "individual" refers to multicellular organisms and includes both plants and animals. Preferred multicellular organisms are animals, more preferred are vertebrates, even more preferred are mammals, and most preferred are humans.

Low or undetectable: As used herein, the phrase "low or undetectable," when used in reference to gene expression level, refers to a level of expression which is either significantly lower than that seen when the gene is maximally induced (e.g., at least five fold lower) or is not readily detectable by the methods used in the following examples section.

Lectin: As used herein, proteins obtained particularly from the seeds of leguminous plants, but also from many other plant and animal sources, that have binding sites for specific mono- or oligosaccharides. Examples include concanavalin A and wheat-germ agglutinin, which are widely used as analytical and preparative agents in the study of glycoprotein.

Mimotope: As used herein, the term "mimotope" refers to a substance which induces an immune response to an antigen or antigenic determinant. Generally, the term mimotope will be used with reference to a particular antigen. For example, a peptide which elicits the production of antibodies to a phospholipase $A_2$ ($PLA_2$) is a mimotope of the antigenic determinant to which the antibodies bind. A mimotope may or may not have substantial structural similarity to or share structural properties with an antigen or antigenic determinant to which it induces an immune response. Methods for generating and identifying mimotopes which induce immune responses to particular antigens or antigenic determinants are known in the art and are described elsewhere herein.

Mutein: As used herein, the term "mutein" refers to a protein or polypeptide differing by one or more amino acids from a given reference (e.g. natural, wild type, etc.) polypeptide Natural origin: As used herein, the term "natural origin" means that the whole or parts thereof are not synthetic and exist or are produced in nature. Preferably, as used herein, the term "natural origin" means that the whole is not synthetic and exist or is produced in nature.

Non-natural: As used herein, the term generally means not from nature, more specifically, the term means from the hand of man.

Non-natural molecular scaffold: As used herein, the phrase "non-natural molecular scaffold" refers to any product made by the hand of man that serves to provide a rigid and repetitive array of first attachment sites. Ideally but not necessarily, these first attachment sites are in a geometric order. The non-natural molecular scaffold may be organic or non-organic and may be synthesized chemically or through a biological process, in part or in whole. The non-natural molecular scaffold is comprised of: (a) a core particle, either of natural or non-natural origin; and (b) at least one first attachment site. Non-natural origin: As used herein, the term "non-natural origin" generally means synthetic or not from nature; more specifically, the term means from the hand of man.

Ordered and repetitive antigen or antigenic determinant array: As used herein, the term "ordered and repetitive antigen or antigenic determinant array" generally refers to a repeating pattern of antigen or antigenic determinant, characterized by a typically and preferably uniform spacial arrangement of the antigens or antigenic determinants with respect to the core particle and virus-like particle, respectively. In one embodiment of the invention, the repeating pattern may be a geometric pattern. Typical and preferred examples of suitable ordered and repetitive antigen or antigenic determinant arrays are those which possess strictly repetitive paracrystalline orders of antigens or antigenic determinants, preferably with spacings of 0.5 to 30 nanometers, preferably 5 to 15 nanometers.

Passive immunization: as used herein, the term "passive immunization" refers to the administration, by any route, of exogenously produced immune molecules (e.g. antibodies) or cells (e.g. T-cells) into an animal. Passive immunization differs from "active" immunization, where immunity is obtained by introduction of an immunogen, vaccine, antigen or hapten-canier conjugate into an individual to elicit an immune response.

Pili: As used herein, the term "pili" (singular being "pilus") refers to extracellular structures of bacterial cells composed of protein monomers (e.g., pilin monomers) which are organized into ordered and repetitive patterns. Further, pili are structures which are involved in processes such as the attachment of bacterial cells to host cell surface receptors, inter-cellular genetic exchanges, and cell-cell recognition. Examples of pili include Type-1 pili, P-pili, F1C pili, S-pili, and 987P-pili. Additional examples of pili are set out elsewhere herein.

Pilus-like structure: As used herein, the phrase "pilus-like structure" refers to structures having characteristics similar to that of pili and composed of protein monomers. One example of a "pilus-like structure" is a structure formed by a bacterial cell which expresses modified pilin proteins that do not form ordered and repetitive arrays that are essentially identical to those of natural pili.

Polypeptide: As used herein the term "polypeptide" refers to a polymer composed of amino acid residues, generally natural amino acid residues, linked together through peptide bonds. A polypeptide may not necessarily be limited in size, and include both proteins and peptides. A peptide is a polypeptide of a typical size of about five to about 50 amino acids, or any number amino acids within this general range. A peptide may, however, also be of longer length, for example up to 120–150 amino acids.

Protein: As used herein, the term protein refers to a polypeptide generally of a size of above about 5 or more, 10 or more 20 or more, 25 or more, 50 or more, 75 or more, 100 or more, 200 or more, 500 or more, 1000 or more, 2000 or more amino acids. Proteins generally have a defined three dimensional structure although they do not necessarily need to, and are often referred to as folded, as opposed to peptides and polypeptides which often do not possess a defined three-dimensional structure, but rather can adopt a large number of different conformations, and are referred to as unfolded. Peptides may, however also have a defined three-dimensional structure.

Purified: As used herein, when the term "purified" is used in reference to a molecule, it means that the concentration of the molecule being purified has been increased relative to molecules associated with it in its natural environment, or environment in which it was produced, found or synthesized. Naturally associated molecules include proteins, nucleic acids, lipids and sugars but generally do not include water, buffers, and reagents added to maintain the integrity or facilitate the purification of the molecule being purified. For example, even if mRNA is diluted with an aqueous solvent during oligo dT column chromatography, mRNA molecules are purified by this chromatography if naturally associated nucleic acids and other biological molecules do not bind to the column and are separated from the subject mRNA molecules. According to this definition, a substance may be 5% or more, 10% or more, 20% or more, 30% or more, 40% or more, 50% or more, 60% or more, 70% or more, 80% or more, 90% or more, 95% or more, 98% or more, 99% or more, or 100% pure when considered relative to its contaminants.

Receptor: As used herein, the term "receptor" refers to proteins or glycoproteins or fragments thereof capable of interacting with another molecule, called the ligand. The ligand may belong to any class of biochemical or chemical compounds. The receptor need not necessarily be a membrane-bound protein. Soluble protein, like e.g., maltose binding protein or retinol binding protein are receptors as well.

Residue: As used herein, the term "residue" is meant to mean a specific amino acid in a polypeptide backbone or side chain.

Recombinant host cell: As used herein, the term "recombinant host cell" refers to a host cell into which one ore more nucleic acid molecules of the invention have been introduced. Host cells include eukaryotes include e.g. mammalian, insect, plant, avian, yeast; and prokaryotic e.g. *E. coli*, *B. subtilis*, etc.

Recombinant virus: As used herein, the phrase "recombinant virus" refers to a virus that is genetically modified by the hand of man. The phrase covers any virus known in the art. More specifically, the phrase refers to a an alphavirus genetically modified by the hand of man, and most specifically, the phrase refers to a Sinbis virus genetically modified by the hand of man.

RNA-phage: As used herein, the term "RNA-phage" refers to RNA viruses infecting bacteria, more specifically to single-stranded positive-sense RNA viruses infecting bacteria.

Vector: As used herein, the term "vector" refers to an agent (e.g., a plasmid or virus) used to transmit genetic material to a host cell. A vector may be composed of either DNA or RNA.

Virus-like particle (VLP): As used herein, the term "virus-like particle" refers to a structure resembling a virus particle. Moreover, a virus-like particle in accordance with the invention is non replicative and noninfectious since it lacks all or part of the viral genome, in particular the replicative and infectious components of the viral genome. A virus-like particle in accordance with the invention may contain nucleic acid distinct from their genome. A typical and preferred embodiment of a virus-like particle in accordance with the present invention is a viral capsid such as the viral capsid of the corresponding virus, bacteriophage, or RNA-phage. The terms "viral capsid" or "capsid", as interchangeably used herein, refer to a macromolecular assembly composed of viral protein subunits. Typically and preferably, the viral protein subunits assemble into a viral capsid and capsid, respectively, having a structure with an inherent repetitive organization, wherein said structure is, typically, spherical or tubular. For example, the capsids of RNA-phages or HBcAg's have a spherical form of icosahedral symmetry. The term "capsid-like structure" as used herein, refers to a macromolecular assembly composed of viral protein subunits ressembling the capsid morphology in the above defined sense but deviating from the typical symmetrical assembly while maintaining a sufficient degree of order and repetitiveness.

Virus-like particle of a bacteriophage: As used herein, the term "virus-like particle of a bacteriophage" refers to a virus-like particle resembling the structure of a bacteriophage, being non replicative and noninfectious, and lacking at least the gene or genes encoding for the replication machinery of the bacteriophage, and typically also lacking the gene or genes encoding the protein or proteins responsible for viral attachment to or entry into the host. This definition should, however, also encompass virus-like particles of bacteriophages, in which the aforementioned gene or genes are still present but inactive, and, therefore, also leading to non-replicative and noninfectious virus-like particles of a bacteriophage.

VLP of RNA phage coat protein: The capsid structure formed from the self-assembly of 180 subunits of RNA phage coat protein and optionally containing host RNA is referred to as a "VLP of RNA phage coat protein". A specific example is the VLP of Qβ coat protein. In this particular case, the VLP of Qβ coat protein may either be assembled exclusively from Qβ CP subunits (generated by expression of a Qβ CP gene containing, for example, a TAA stop codon precluding any expression of the longer A1 protein through suppression, see Kozlovska, T. M., et al., *Intervirology* 39: 9–15 (1996)), or additionally contain A1 protein subunits in the capsid assembly.

Virus particle: The term "virus particle" as used herein refers to the morphological form of a virus. In some virus types it comprises a genome surrounded by a protein capsid; others have additional structures (e.g., envelopes, tails, etc.).

One, a, or an: When the terms "one," "a," or "an" are used in this disclosure, they mean "at least one" or "one or more," unless otherwise indicated.

As used herein when referring to any numerical value, the term "about" means a value of ±10% of the stated value (e.g., "about 50° C." encompasses a range of temperatures from 45° C. to 55° C., inclusive; similarly, "about 100 mM" encompasses a range of concentrations from 90 mM to 110 mM inclusive).

Overview

We have now developed potent immunogens for the induction of antibodies specific for angiotensin peptides which are effective even without the use of adjuvants, and which may allow specific targeting of angotensinogen, angiotensin I or angiotensin II. The immunogens consist of angiotensin peptide moieties which are bound to virus-like particles (VLP) or other core particles such as bacterial pili or pilus-like particles. This results in a highly immunogenic repetitive antigen array which is able to stimulate antibody formation even without the use of adjuvants. Depending on the amino acid sequence of the angiotensin peptide moieties used, high antibody titers are induced, and, moreover, can be specifically induced against the N- or C-terminal ends of angiotensinogen, angiotensin I or angiotensin II. This allows the specific targeting of only one species of angiotensin peptides or a combination thereof. The immunogens of the present invention thus can be used in an immunotherapeutic approach to combat conditions associated with elevated levels of angiotensin peptide moieties, particularly angiotensin II and derivatives thereof, produced by the RAS.

Formation of conjugates of the invention, i.e. binding one or more angiotensin peptide moieties to the core particle (e.g., the VLP), is achieved by attachment, linkage, fusion or other binding, including covalent and non covalent bonds. In one embodiment, the VLP contains a first attachment site, the organic molecule contains a second attachment site. Association between the organic molecule occurs by linking the first and second attachment sites directly, or via a third molecule. Attachment sites may occur naturally, or may be introduced.

Immunization of animals with conjugates of angiotensin peptide moieties and core particles, or with conjugates comprising such conjugates as provided by the invention, induce a strong immune response against the displayed angiotensin peptide moieties. Hence, the conjugates and conjugates of the invention are useful for the stimulation of an immune response against a variety of angiotensin peptide moieties or derivatives thereof, and thus for the use in animals. The present invention also relates to a vaccine comprising an immunologically effective amount of one or more of the conjugates or conjugates of the present invention together with a pharmaceutically acceptable diluent, carrier or excipient. The conjugates and conjugates of the invention can be used to vaccinate an animal against one or more angiotensin peptide moieties or derivatives thereof. The vaccination can be for prophylactic or therapeutic purposes, or both. In a related aspect immune molecules, such as antibodies, generated against such conjugates or conjugates may be used for treatment, prophylaxis or diagnosis of a disease, condition or disorder. Such antibodies, conjugates and conjugates of the invention are also useful as components kits.

Thus, in one aspect the invention provides conjugates of one or more angiotensin peptide moieties with a carrier in an ordered and repetitive angiotensin peptide moiety-carrier conjugate, and methods of making such conjugates. The invention also provides conjugates comprising at least one such conjugate of the invention and at least one other component, suitably at least one excipient or carrier and particularly at least one pharmaceutically acceptable excipient or carrier. The conjugates and conjugates of the invention are useful for inducing immune responses against angiotensin peptide moieties. Such an immune response can be can be utilized to generate antibodies, useful for therapeutic, prophylactic and diagnostic purposes.

The conjugates of the present invention comprise highly ordered and repetitive arrays of one or more angiotensin peptide moieties. Conjugate arrays according to this aspect of the invention comprise (a) a core particle, comprising a first attachment site and (b) an angiotensin peptide moiety comprising a second attachment site, wherein the elements (a) and (b) are associated through the first and second attachment sites to form said ordered and repetitive arrays of angiotensin peptide moieties.

Core particles suitably used in the conjugates and conjugates of the invention may be natural or non-natural. Natural core particles used in the conjuages and conjugates of the present invention include virus particles, virus-like particles, and pili. The proteins of these natural core particles may be natural or recombinant. The first attachment sites on the core particle may occur naturally or may be introduced via chemical or recombinant means. Angiotensin peptide moieties used in the conjugates and conjugates of the present invention are those suitable for inducing immune responses against a variety of components of the RAS (i.e., a variety of angiotensin peptide moieties or derivatives thereof), including but not limited to an angiotensin peptide, preferably those comprising, or alternatively consisting of, the sequence, or fragments thereof, of angiotensinogen, angiotensin I (a decapeptide of formula Asp-Arg-Val-Tyr-Ile-His-Pro-Phe-His-Leu, SEQ ID NO: 16) or angiotensin II (an octapeptide of formula Asp-Arg-Val-Tyr-Ile-His-Pro-Phe, SEQ ID NO: 17), or functionally equivalent variants thereof including those angiotensin peptide moieties described elsewhere herein. The second attachment site on the angiotensin peptide moiety may naturally occur or be introduced. The interaction between first and second sites may be direct, or may involve at least one other molecule, e.g. a linker. Furthermore, cross-linking molecules may be used in accordance with the present invention for association of the first and second attachment sites. Cross-linking molecules are typically used in addition to the linker.

The conjugates and conjugates of the invention are suprisingly effective in inducing immune responses, particularly antibodies, against a variety of angiotensin peptide moieties. Thus, they are useful in conjugates suitable for immunization of animals for therapeutic or prophylaxis against diseases, disorders or conditions associated with the RAS, including but not limited to hypertension, stroke, infarction, congestive heart failure, kidney failure or retinal hemorrhage. Antibodies produced by immunization with the conjugates and conjugates of the invention are also useful for therapeutic and prophylactic purposes.

In other embodiments, the invention provides methods of treatment and prevention of a disease utilizing the conjugates and conjugates of the invention. In another embodiment, the invention provides kits suitable for diagnosis and screening.

Conjugates of Ordered and Repetitive Arrays

The present invention provides conjugates, and conjugates of conjugates, comprising an ordered and repetitive array of one or more angiotensin peptide moieties. Furthermore, the invention conveniently enables the practitioner to construct ordered and repetitive arrays for various purposes, and preferably the induction of an immune response against one or more angiotensin peptide moieties or derivatives thereof.

Conjugates of the invention essentially comprise, or alternatively consist of, two elements: (1) a non-natural molecular scaffold; and (2) at least one angiotensin peptide moiety with at least one second attachment site capable of association through at least one bond to said first attachment site.

The non-natural molecular scaffold comprises, or alternatively consists of: (a) a core particle selected from the group consisting of (1) a core particle of non-natural origin and (2) a core particle of natural origin; and (b) at least one first attachment site connected to said core particle by at least one covalent bond. Core particles used in the conjugates, conjugates and methods of the invention include inorganic molecules, virus particles, virus-like particles, and bacterial pili. The angiotensin peptide moieties used in the conjugates, conjugates and methods of the invention have at least one second attachment site which is selected from the group consisting of (a) an attachment site not naturally occurring within the angiotensin peptide moiety; and (b) an attachment site naturally occurring within the angiotensin peptide moiety The invention provides for an ordered and repetitive array through an association of the second attachment site to the first attachment site by way of at least one bond. Thus, the angiotensin peptide moiety and the non-natural molecular scaffold are brought together through this association of the first and the second attachment site to form an ordered and repetitive antigen array.

The practioner may specifically design the angiotensin peptide moiety and the second attachment site such that the arrangement of all the moieties bound to the non-natural molecular scaffold, or in certain embodiments to the core particle, will be uniform. For example, one may place a single second attachment site on the angiotensin peptide moiety, thereby ensuring through design that all angiotensin peptide moieties that are attached to the non-natural molecular scaffold are positioned in a uniform way. In one such aspect of the invention, one or more additional amino acids (leading to a non-naturally occurring second attachment site) are added either at the C- or at the N-terminus of the angiotensin peptide moiety sequences in order to assure, in particular, an oriented and ordered association with the core particle in accordance with the present invention. Thus, the invention provides a convenient means of placing any angiotensin peptide moiety onto a non-natural molecular scaffold in a defined order and in a manner which forms a repetitive pattern.

As will be clear to those of ordinary skill in the art, certain embodiments of the invention involve the use of recombinant nucleic acid technologies such as cloning, polymerase chain reaction, the purification of DNA and RNA, the expression of recombinant proteins in prokaryotic and eukaryotic cells, etc. Such methodologies are well known to those skilled in the art and may be conveniently found in published laboratory methods manuals (e.g., Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997)). Fundamental laboratory techniques for working with tissue culture cell lines (Celis, J., ed., CELL BIOLOGY, Academic Press, $2^{nd}$ edition, (1998)) and antibody-based technologies (Harlow, E. and Lane, D., "Antibodies: A Laboratory Manual," Cold Spring Harbor Laboratory, Cold Spring Harbor, N.Y. (1988); Deutscher, M. P., "Guide to Protein Purification," *Meth. Enzymol.* 128, Academic Press San Diego (1990); Scopes, R. K., "Protein Purification Principles and Practice," $3^{rd}$ ed., Springer-Verlag, New York (1994)) are also adequately described in the literature, all of which are incorporated herein by reference.

Furthermore, technologies for coupling organic molecules to amino acids and means for making derivatives of angiotensin peptide moieties containing appropriate second attachment sites such as are neccessary for the practice of the invention are well known to those of skill in the art. Such methodologies may be found in chemical text books and publications, examples of which are included below and are incorportated by reference; U.S. Pat. No. 5,876,727; WO 99/61054; Isomura, S. et al. *J. Org. Chem.* 66:4115–4121 (2001); Matsushita, H. et al. *Biochem. Biophys. Res. Comm.* 57:1006–1010. (1974); Langone, J. L. and Van Vunakis, H., *Methods Enzymol.* 84:628–640 (1982); Wong, *Chemistry of Protein Conjugation and Cross-Linking*. CRC Press, Inc., Boca Raton, Fla. (1991.)

Core Particles and Non-Natural Molecular Scaffolds

In one embodiment, the present invention provides methods for the formation of an ordered and repetitive array of one or more angiotensin peptide moieties. By the invention, this occurs by the association of a core particle to which is attached one or more angiotensin peptide moieties via first and second attachment sites.

Thus, one element in certain conjugates and conjugates of the invention is a non-natural molecular scaffold comprising, or alternatively consisting of, a core particle and a first attachment site. More specifically, the non-natural molecular scaffold comprises, or alternatively consists of, (a) a core particle of natural or non-natural origin and (b) at least one first attachment site connected to the core particle by at least one covalent bond.

Core particles. In one embodiment of the present invention, a core particle is a synthetic polymer, a lipid micelle or a metal. Such core particles are known in the art, providing a basis from which to build the novel non-natural molecular scaffold of the invention. By way of example, synthetic polymer or metal core particles are disclosed in U.S. Pat. No. 5,770,380, and U.S. Pat. No. 5,334,394, which are incorporated by reference herein in their entirities. Suitable metals include, but are not limited to, chromium, rubidium, iron, zinc, selenium, nickel, gold, silver, platinum. Suitable ceramic materials include, but are not limited to, silicon dioxide, titanium dioxide, aluminum oxide, ruthenium oxide and tin oxide. The core particles of this embodiment may be made from organic materials including, but not limited to, carbon and suitable polymers, including polystyrene, nylon and nitrocellulose. For nanocrystalline particles, particles made from tin oxide, titanium dioxide or carbon (diamond) are useful. Lipid micelles for use in the present invention are prepared by any means known in the art, for example, Baiselle and Millar (*Biophys. Chem.* 4:355–361 (1975)) or Corti et al. (*Chem. Phys. Lipids* 38:197–214 (1981)) or Lopez et al. (*FEBS Lett.* 426:314–318 (1998)) or Topchieva and Karezin (*J. Colloid Interface Sci.* 213:29–35 (1999)) or Morein et al., (*Nature* 308:457–460 (1984)), which are incorporated herein by reference in their entirities.

In one embodiment of the invention the core particle is produced through a biological process, which may be natural or non-natural. For example, viruses and bacterial pili or pilus-like structures are formed from proteins which are organized into ordered and repetitive structures. Therefore, the present invention comprises conjugates, conjugates and methods comprising useful core particles which include, but are not limited to a virus, virus-like particle, a bacterial pilus, a phage, a viral capsid particle or fragments thereof. In certain such embodiments, the proteins may be recombinant.

In certain embodiments, the core particle of the non-natural molecular scaffold comprises a virus, a bacterial pilus, a structure formed from bacterial pilin, a bacteriophage, a virus-like particle, a viral capsid particle or a recombinant form thereof. Any virus known in the art having an ordered and repetitive coat and/or core protein structure may be selected for use as in the methods, conjugates and conjugates of the invention as a non-natural molecular scaffold. Examples of suitable viruses include, but are not limited to, sindbis and other alphaviruses, rhabdoviruses (e.g. vesicular stomatitis virus), picornaviruses (e.g., human rhino virus, Aichi virus), togaviruses (e.g., rubella virus), orthomyxoviruses (e.g., Thogoto virus, Batken virus, fowl plague virus), polyomaviruses (e.g., polyomavirus BK, polyomavirus JC, avian polyomavirus BFDV), parvoviruses, rotaviruses, bacteriophage Qβ, bacteriophage R17, bacteriophage M11, bacteriophage MX1, bacteriophage NL95, bacteriophage fr, bacteriophage GA, bacteriophage SP, bacteriophage MS2, bacteriophage f2, bacteriophage PP7, bacteriophage AP205, Norwalk virus, foot and mouth disease virus, a retrovirus, Hepatitis B virus, Tobacco mosaic virus, Flock House Virus, and human Papillomavirus (for example, see Table 1 in Bachman, M. F. and Zinkernagel, R. M., *Immunol. Today* 17:553–558 (1996)). In more specific exemplary embodiments of the present invention the core particle may comprise, or alternatively consist of, recombinant proteins of Rotavirus, recombinant proteins of Norwalk virus, recombinant proteins of Alphavirus, recombinant proteins which form bacterial pili or pilus-like structures, recombinant proteins of Foot and Mouth Disease virus, recombinant proteins of Retrovirus, recombinant proteins of Hepatitis B virus (e.g., a HBcAg), recombinant proteins of Tobacco mosaic virus, recombinant proteins of Flock House Virus, and recombinant proteins of human Papillomavirus.

The core particle used in conjugates, conjugates and methods of the invention may further comprise, or alternatively consist of, one or more fragments of such proteins, as well as variants of such proteins which retain the ability to associate with each other to form ordered and repetitive antigen or antigenic determinant arrays. For example, as explained in commonly owned copending U.S. patent application Ser. No. 10/050,902, (filed Jan. 18, 2002, the disclosure of which is incorporated herein by reference in its entirety) core particles may be formed from variant forms of the human HBcAg which differ markedly from the wild-type particle in amino acid sequence identity and similarity, and in sequence length. For example, amino acid sequence of the HBcAg of Hepatitis B viruses which infect snow geese and ducks differs sufficiently from that of HBcAg of viruses infected mammals that alignment of the proteins is difficult. However, both viruses retain the ability to form core structures suitable for the formation of ordered repetitive antigen arrays. Similarly, HBcAg may retain the ability to form multimeric particles, typical of a virus, after removal of N-terminal leader sequences, further deletions, substitutions, or additions to the sequence. Methods which can be used to determine whether proteins form such structures comprise gel filtration, agarose gel electrophoresis, sucrose gradient centrifugation and electron microscopy (e.g., Koschel, M. et al., *J. Virol* 73: 2153–2160 (1999)).

First Attachment Sites. Whether natural or non-natural, the core particle used in the conjugates, conjugates and methods of the present invention will generally possess a component comprising a first attachment site that is attached to the natural or non-natural core particle by at least one covalent bond. The element comprising the first attachment site is bound to a core particle in a non-random fashion that provides a nucleation site for creating an ordered and repetitive array. Ideally, but not necessarily, this element is associated with the core particle in a geometric order. The first attachment site may be a natural part of the core particle, such as a surface exposed amino acid residue suitable for coupling to the second attachment site. For example, lysine and cysteine may form non-peptide bonds via reactive groups on the amino acid. Alternatively, an element containing the first attachment site may be introduced into the core particle via chemical coupling or through the design of recombinant molecules. The first attachment site may be, or be found on, any element comprising bound to a core particle by at least one covalent bond.

The first attachment site may comprise, or alternatively may consist of, a protein, a polypeptide, a peptide, an amino acid (i.e., a residue of a protein, a polypeptide or peptide), a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. In a more specific embodiment, the first attachment site comprising an antigen, an antibody or antibody fragment, biotin, avidin, strepavidin, a receptor, a receptor ligand, a ligand, a ligand-binding protein, an interacting leucine zipper polypeptide, an amino group, a chemical group reactive to an amino group; a carboxyl group, chemical group reactive to a carboxyl group, a sulfhydryl group, a chemical group reactive to a sulfhydryl group, or a combination thereof.

In one embodiment, the invention utilizes genetic engineering of a virus to create a fusion between an ordered and repetitive viral envelope protein the element comprising the first attachment site which comprising a heterologous protein, peptide, antigenic determinant or a reactive amino acid residue of choice. Other genetic manipulations known to those in the art may be included in the construction of the non-natural molecular scaffold; for example, it may be desirable to restrict the replication ability of the recombinant virus through genetic mutation. The viral protein selected for fusion to the protein containing the first attachment site protein should have an organized and repetitive structure. Such an organized and repetitive structure include paracrystalline organizations with a spacing of 0.5–30 nm, preferably of 5–15 nm on the surface of the virus. The creation of this type of fusion protein will result in multiple, ordered and repetitive first attachment sites on the surface of the virus. Thus, the ordered and repetitive organization of the first attachment sites resulting therefrom will reflect the normal organization of the native viral protein.

As will be understood by those of ordinary skill in the art, the first attachment site may be or be a part of any suitable protein, polypeptide, sugar, polynucleotide, peptide (amino acid), natural or synthetic polymer, a secondary metabolite or combination thereof that may serve to specifically attach the antigen or antigenic determinant of choice to the non-natural molecular scaffold. In one embodiment, the attachment site is a protein or peptide that may be selected from those known in the art. For example, the first attachment site may be a ligand, a receptor, a lectin, avidin, streptavidin, biotin, an epitope such as an HA or T7 tag, Myc, Max, immunoglobulin domains and any other amino acid sequence known in the art that would be useful as a first attachment site.

It will be further understood by those of ordinary skill in the art that in another embodiment of the invention, the first attachment site may be created secondarily to the creation of an element carrying the first attachment site (e.g., protein or polypeptide) utilized in constructing the in-frame fusion to the capsid protein. For example, a protein may be utilized for fusion to the envelope protein with an amino acid sequence known to be glycosylated in a specific fashion, and the sugar moiety added as a result may then serve at the first attachment site of the viral scaffold by way of binding to a lectin serving as the secondary attachment site of an antigen. Alternatively, a sequence may be biotinylated in vivo and the biotin moiety may serve as the first attachment site of the invention, or the sequence may be subjected to chemical modification of distinct amino acid residues in vitro, the modification serving as the first attachment site.

In one specific embodiment of the invention, the first attachment site is the JUN-FOS leucine zipper protein domain that is fused in frame to the Hepatitis B capsid (core) protein (HBcAg). However, it will be clear to those of ordinary skill in the art that other viral capsid proteins may be utilized in the fusion protein construct for locating the first attachment site in the non-natural molecular scaffold of the invention. For example, in other embodiments of the invention, the first attachment site is selected to be a lysine or cysteine residue that is fused in frame to the HBcAg. It will also be clear to all individuals in the art that other viral capsid or virus-like particles may be utilized in the fusion protein construct for locating the first attachment in the non-natural molecular scaffold of the invention.

Viral particles. In one embodiment of the invention, the non-natural molecular scaffold is a recombinant alphavirus, and more specifically, a recombinant Sindbis virus. Several members of the alphavirus family, Sindbis (Xiong, C. et al., *Science* 243:1188–1191 (1989); Schlesinger, S., *Trends Biotechnol.* 11:18–22 (1993)), Semliki Forest Virus (SFV) (Liljeström, P. & Garoff, H., *Bio/Technology* 9:1356–1361 (1991)) and others (Davis, N. L. et al., *Virology* 171: 189–204 (1989)), have received considerable attention for use as virus-based expression vectors for a variety of different proteins (Lundstrom, K., *Curr. Opin. Biotechnol.* 8:578–582 (1997); Liljeström, P., *Curr. Opin. Biotechnol.* 5:495–500 (1994)) and as candidates for vaccine development. The use of alphaviruses for the expression of heterologous proteins and the development of vaccines has been disclosed (see U.S. Pat. Nos. 5,766,602; 5,792,462; 5,739,026; 5,789,245; and 5,814,482; the disclosures all of which are incorporated by reference in their entirities). The construction of an alphaviral scaffold according to this aspect of the invention may be done by means generally known in the art of recombinant DNA technology, as described by the aforementioned articles, which are incorporated herein by reference. A variety of recombinant host cells can be utilized to produce a viral-based core particle for attachment of one or more angiotensin peptide moieties.

Packaged RNA sequences can also be used to infect host cells. These packaged RNA sequences can be introduced to host cells by adding them to the culture medium. For example, the preparation of non-infective alphaviral particles is described in a number of sources, including "Sindbis Expression System", Version C (Invitrogen Corporation, Carlsbad Calif.; Catalog No. K750-1).

When mammalian cells are used as recombinant host cells for the production of viral-based core particles, these cells will generally be grown in tissue culture. Methods for growing cells in culture are well known in the art (see, e.g., Celis, J., ed., CELL BIOLOGY, Academic Press, $2^{nd}$ edition, (1998); Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997); Freshney, R., CULTURE OF ANIMAL CELLS, Alan R. Liss, Inc. (1983)).

The invention thus includes viral-based core particles which comprise, or alternatively consist of, a virus, virus-like particle, a phage, a viral capsid particle or a recombinant form thereof. Ordinarily skilled artisans have the knowledge to produce such core particles and attach first attachment sites thereto. The production of Hepatitis B virus-like particles, in particular those assembled or self-assembled from HBcAg, and measles viral capsid particles as core particles is disclosed in Examples 17 to 22 of WO 00/32227, which is explicitly incorporated herein by reference. In such embodiments, the JUN leucine zipper protein domain or FOS leucine zipper protein domain may be used as a first attachment site for the non-natural molecular scaffold of the invention. One of ordinary skill in the art will be aware of methods for constructing Hepatitis B core particles carrying an in-frame fused peptide with a reactive lysine residue and angiotensin peptide moieties carrying a genetically fused cysteine residue, as first and second attachment site, respectively.

In other embodiments, the core particles used in conjugates of the invention are composed of a Hepatitis B capsid (core) protein (HBcAg), a fragment of a HBcAg, or other protein or peptide which can form virus-like particles, which are ordered arrays, which have been modified to either eliminate or reduce the number of free cysteine residues. Zhou et al. (*J. Virol.* 66:5393–5398 (1992)) demonstrated that HBcAgs which have been modified to remove the naturally resident cysteine residues retain the ability to associate and form multimeric structures. Thus, core particles suitable for use in conjugates of the invention include those comprising modified HBcAgs, or fragments thereof, in which one or more of the naturally resident cysteine residues have been either deleted or substituted with another amino acid residue (e.g., a serine residue). In one embodiment of the invention, a modified HBcAg comprising the amino acid sequence shown in SEQ ID NO:1, or subportion thereof, is used to prepare non-natural molecular scaffolds. In particular, modified HBcAgs suitable for use in the practice of the invention include proteins in which one or more of the cysteine residues at positions corresponding to positions 48, 61, 107 and 185 of a protein having the amino acid sequence shown in SEQ ID NO:1 have been either deleted or substituted with other amino acid residues (e.g., a serine residue). As one skilled in the art would recognize, cysteine residues at similar locations in HBcAg variants having amino acids sequences which differ from that shown in SEQ ID NO:1 could also be deleted or substituted with other amino acid residues. The modified HBcAg variants can then be used to prepare vaccine conjugates of the invention.

Under certain circumstances (e.g., when a heterobifunctional cross-linking reagent is used to attach one or more angiotensin peptide moieties to the non-natural molecular scaffold), the presence of free cysteine residues in the HBcAg is believed to lead to covalent coupling of toxic components to core particles, as well as the cross-linking of monomers to form undefined species. Further, in many instances, these toxic components may not be detectable with assays performed on conjugates of the invention. This is so because covalent coupling of toxic components to the non-natural molecular scaffold would result in the formation of a population of diverse species in which toxic components are linked to different cysteine residues, or in some cases no cysteine residues, of the HBcAgs. In other words, each free cysteine residue of each HBcAg will not be covalently linked to toxic components. Further, in many instances, none of the cysteine residues of particular HBcAgs will be linked to toxic components. Thus, the presence of these toxic components may be difficult to detect because they would be present in a mixed population of molecules. The administration to an individual of HBcAg species containing toxic components, however, could lead to a potentially serious adverse reaction.

It is well known in the art that free cysteine residues can be involved in a number of chemical side reactions. These side reactions include disulfide exchanges, reaction with chemical substances or metabolites that are, for example, injected or formed in a combination therapy with other substances, or direct oxidation and reaction with nucleotides upon exposure to UV light. Toxic adducts could thus be generated, especially considering the fact that HBcAgs have a strong tendency to bind nucleic acids. Detection of such toxic products in antigen-capsid conjugates would be difficult using capsids prepared using HBcAgs containing free cysteines and heterobifunctional cross-linkers, since a distribution of products with a broad range of molecular weight would be generated. The toxic adducts would thus be distributed between a multiplicity of species, which individually may each be present at low concentration, but reach toxic levels when together.

In view of the above, one advantage to the use of HBcAgs in vaccine conjugates which have been modified to remove naturally resident cysteine residues is that sites to which toxic species can bind when antiogensin peptide moieties are attached to the non-natural molecular scaffold would be reduced in number or eliminated altogether. Further, a high concentration of cross-linker can be used to produce highly decorated particles without the drawback of generating a plurality of undefined cross-linked species of HBcAg monomers (i.e., a diverse mixture of cross-linked monomeric HbcAgs).

A number of naturally occurring HBcAg variants suitable for use in the practice of the present invention have been identified. Yuan et al., (*J. Virol.* 73:10122–10128 (1999)), for example, describe variants in which the isoleucine residue at position corresponding to position 97 in SEQ ID NO:1 is replaced with either a leucine residue or a phenylalanine residue. The amino acid sequences of a number of HBcAg variants, as well as several Hepatitis B core antigen precursor variants, are disclosed in GenBank reports AAF121240, AF121239, X85297, X02496, X85305, X85303, AF151735, X85259, X85286, X85260, X85317, X85298, AF043593, M20706, X85295, X80925, X85284, X85275, X72702, X85291, X65258, X85302, M32138, X85293, X85315, U95551, X85256, X85316, X85296, AB033559, X59795, X8529, X85307, X65257, X85311, X85301, X85314, X85287, X85272, X85319, AB010289, X85285, AB010289, AF121242, M90520, P03153, AF110999, and M95589, the disclosures of each of which are incorporated herein by reference. These HBcAg variants differ in amino acid sequence at a number of positions, including amino acid residues which corresponds to the amino acid residues located at positions 12, 13, 21, 22, 24, 29, 32, 33, 35, 38, 40, 42, 44, 45, 49, 51, 57, 58, 59, 64, 66, 67, 69, 74, 77, 80, 81, 87, 92, 93, 97, 98, 100, 103, 105, 106, 109, 113, 116, 121, 126, 130, 133, 135, 141, 147, 149, 157, 176, 178, 182 and 183 in SEQ ID NO:1.

Further HBcAg variants suitable for use in the compositions of the invention, and which may be further modified according to the disclosure of this specification are described in WO 00/198333, WO 00/177158 and WO 00/214478, herein included by reference in their entirety.

HBcAgs suitable for use in the present invention may be derived from any organism so long as they are able to associate to form an ordered and repetitive antigen array. Generally processed HBcAgs (i.e., those which lack leader sequences) will be used in the vaccine conjugates of the invention. The present invention includes vaccine conjugates, as well as methods for using these conjugates, which employ the above described variant HBcAgs for the preparation of non-natural molecular scaffolds. Further included within the scope of the invention are additional HBcAg variants which are capable of associating to form dimeric or multimeric structures. Thus, the invention further includes vaccine conjugates comprising HBcAg polypeptides comprising, or alternatively consisting of, amino acid sequences which are at least about 80%, about 85%, about 90%, about 95%, about 97%, or about 99% identical to any of the amino acid sequences shown in the above sequences, including SEQ ID No: 1, and forms of these proteins which have been processed, where appropriate, to remove the N-terminal leader sequence.

Whether the amino acid sequence of a polypeptide has an amino acid sequence that is at least about 80%, about 85%, about 90%, about 95%, about 97%, or about 99% identical to one of the amino acid sequences shown above, or a subportion thereof, can be determined conventionally using known computer programs such the Bestfit program. When using Bestfit or any other sequence alignment program to determine whether a particular sequence is, for instance, about 95% identical to a reference amino acid sequence according to the present invention, the parameters are set such that the percentage of identity is calculated over the full length of the reference amino acid sequence and that gaps in homology of up to 5% of the total number of amino acid residues in the reference sequence are allowed. In such a manner, comparisons may be made between the amino acid sequence of HBcAg of SEQ ID NO:1 and other HBcAg. When comparing proteins that are relatively similar, reference to an amino acid residue of a HBcAg variant located at a position which corresponds to a particular position in SEQ ID NO:1, refers to the amino acid residue which is present at that position in the amino acid sequence shown in SEQ ID NO:1. The homology between these HBcAg variants is for the most part high enough among Hepatitis B viruses that infect mammals so that one skilled in the art would have little difficulty reviewing both the amino acid sequence shown in SEQ ID NO:1 and that of a particular HBcAg variant and identifying "corresponding" amino acid residues. For example, in comparisons between the SEQ ID NO:1 and the amino acid sequence of the an HBcAg derived from a virus which infects woodchucks, it is readily apparent that a three amino acid residue insert is present in that sequence between amino acid residues 155 and 156 of SEQ ID NO:1.

However, where alignment is difficult, one skilled in the art would recognize the importance of particular amino acids or motifs in a sequence. For example, the amino acid sequence of HBcAg from human viruses differs from duck viruses such that alignment is difficult, yet one skilled in the art would recognize conserved cysteine residues could be either substituted with another amino acid residue or deleted prior to their inclusion in vaccine conjugates of the invention.

In one embodiment, the cysteine residues at positions 48 and 107 of a protein having the amino acid sequence shown in SEQ ID NO:1 are deleted or substituted with another amino acid residue but the cysteine at position 61 is left in place. Further, the modified polypeptide is then used to prepare vaccine conjugates of the invention.

The preparation of preferred Hepatitis B virus-like particles, which can be used for the present invention, is disclosed, for example, in WO 00/32227, and hereby in particular in Examples 17 to 19 and 21 to 24, as well as in WO 01/85208, and hereby in particular in Examples 17 to 19, 21 to 24, 31 and 41, and in pending U.S. application Ser. No. 10/050,902 filed by the present assignee on Jan. 18, 2002. For the latter application, it is in particular referred to Example 23, 24, 31 and 51. All three documents are explicitly incorporated herein by reference.

As set out in Example 31 of U.S. application Ser. No. 10/050,902 filed by the present assignee on Jan. 18, 2002, the cysteine residues at positions 48 and 107, which are accessible to solvent, may be removed, for example, by site-directed mutagenesis. In one such example, it has been found that the Cys-48-Ser, Cys-107-Ser HBcAg double mutant constructed as described in copending U.S. patent application Ser. No. 10/050,902, filed Jan. 18, 2002, (which is incorporated herein by reference in its entirety) can be expressed in *E. coli.*

As discussed above, the elimination of free cysteine residues reduces the number of sites where toxic components can bind to the HBcAg, and also eliminates sites where cross-linking of lysine and cysteine residues of the same or of neighboring HBcAg molecules can occur. The cysteine at position 61, which is involved in dimer formation and forms a disulfide bridge with the cysteine at position 61 of another HBcAg, will normally be left intact for stabilization of HBcAg dimers and multimers of the invention. Cross-linking experiments performed with (1) HBcAgs containing free cysteine residues and (2) HBcAgs whose free cysteine residues have been made unreactive with iodacetamide, indicate that free cysteine residues of the HBcAg are responsible for cross-linking between HBcAgs through reactions between heterobifunctional cross-linker derivatized lysine side chains, and free cysteine residues. It was also found that that cross-linking of HBcAg subunits leads to the formation of high molecular weight species of undefined size which can not be resolved by SDS-polyacrylamide gel electrophoresis.

When an angiotensin peptide moiety is linked to the non-natural molecular scaffold through a lysine residue, it may be advantageous to either substitute or delete one or both of the naturally resident lysine residues located at positions corresponding to positions 7 and 96 in SEQ ID NO:1, as well as other lysine residues present in HBcAg variants. The elimination of these lysine residues results in the removal of binding sites for angiotensin peptide moieties which could disrupt the ordered array and should improve the quality and uniformity of the final vaccine conjugate.

In many instances, when both of the naturally resident lysine residues at positions corresponding to positions 7 and 96 in SEQ ID NO:1 are eliminated, another lysine will be introduced into the HBcAg as an attachment site for an angiotensin peptide moiety. Methods for inserting such a lysine residue are set out, for example, in copending U.S. patent application Ser. No. 10/050,902, filed Jan. 18, 2002, and hereby in particular in Example 23 of of U.S. application Ser. No. 10/050,902 (which is incorporated herein by reference in its entirety). It will often be advantageous to introduce a lysine residue into the HBcAg when, for example, both of the naturally resident lysine residues at positions corresponding to positions 7 and 96 in SEQ ID NO:1 are altered and one seeks to attach the angiotensin peptide moiety to the non-natural molecular scaffold using a heterobifunctional cross-linking agent.

The C-terminus of the HBcAg has been shown to direct nuclear localization of this protein (Eckhardt et al., *J. Virol.* 65:575–582 (1991).) Further, this region of the protein is also believed to confer upon the HBcAg the ability to bind nucleic acids.

In some embodiments, vaccine conjugates of the invention will contain HBcAgs which have nucleic acid binding activity (e.g., which contain a naturally resident HBcAg nucleic acid binding domain). HBcAgs containing one or more nucleic acid binding domains are useful for preparing vaccine conjugates which exhibit enhanced T-cell stimulatory activity. Thus, the vaccine conjugates of the invention include conjugates which contain HBcAgs having nucleic acid binding activity. Further included are vaccine conjugates, as well as the use of such conjugates in vaccination protocols, where HBcAgs are bound to nucleic acids. These HBcAgs may bind to the nucleic acids prior to administration to an individual or may bind the nucleic acids after administration.

Further HBcAgs suitable for use in the practice of the present invention include N- and C-terminal truncation mutants, and muteins whose amino acid sequences comprises or alternatively consists of, amino acid sequences which are at least about 80%, about 85%, about 90%, about 95%, about 97%, or about 99% identical to the above described truncation mutants.

As discussed above, in certain embodiments of the invention, a lysine residue is introduced as a first attachment site into a polypeptide which forms the non-natural molecular scaffold. In preferred embodiments, vaccine conjugates of the invention are prepared using a HBcAg comprising, or alternatively consisting of, amino acids 1–144 or amino acids 1–149 or amino acids 1–185 of SEQ ID NO:1 which is modified so that the amino acids corresponding to positions 79 and 80 are replaced with a peptide having the amino acid sequence of Gly-Gly-Lys-Gly-Gly (SEQ ID NO: 31) and the cysteine residues at positions 48 and 107 are either deleted or substituted with another amino acid residue, while the cysteine at position 61 is left in place.

The invention further includes vaccine conjugates comprising fragments of a HBcAg comprising, or alternatively consisting of, an amino acid sequence other than that shown in SEQ ID NO:1 from which a cysteine residue not present at corresponding location in SEQ ID NO:1 has been deleted.

Vaccine conjugates of the invention may comprise mixtures of different HBcAgs. Thus, these vaccine conjugates may be composed of HBcAgs which differ in amino acid sequence. For example, vaccine conjugates could be prepared comprising a "wild-type" HBcAg and a modified HBcAg in which one or more amino acid residues have been altered (e.g., deleted, inserted or substituted).

The invention further includes vaccine conjugates where the non-natural molecular scaffold is prepared using a HBcAg fused to another protein. As discussed above, one example of such a fusion protein is a HBcAg/FOS fusion. Other examples of HBcAg fusion proteins suitable for use in vaccine conjugates of the invention include fusion proteins where an amino acid sequence has been added which aids in the formation and/or stabilization of HBcAg dimers and multimers. This additional amino acid sequence may be fused to the C-terminus of the HBcAg. One example, of such a fusion protein is a fusion of a HBcAg with the GCN4 helix region of *Saccharomyces cerevisiae*, which forms homodimers via non-covalent interactions which can be used to prepare and stabilize HBcAg dimers and multimers.

In one embodiment, the invention provides vaccine conjugates prepared using HBcAg fusions proteins comprising a HBcAg, or fragment thereof, with a GCN4 polypeptide (SEQ ID NO: 5, PAALKRARNEAARRSRARKLQRMK-QLEDKVEELLSKNYHLENEVARLKK) fused to the C-terminus. This GCN4 polypeptide may also be fused to the N-terminus of the HbcAg.

HBcAg/src homology 3 (SH3) domain fusion proteins could also be used to prepare vaccine conjugates of the invention. SH3 domains are relatively small domains found in a number of proteins which confer the ability to interact with specific proline-rich sequences in protein binding partners (see McPherson, *Cell Signal* 11:229–238 (1999). HBcAg/SH3 fusion proteins could be used in several ways. First, the SH3 domain could form a first attachment site which interacts with a second attachment site of the angiotensin peptide moiety. Similarly, a proline rich amino acid sequence could be added to the HBcAg and used as a first attachment site for an SH3 domain second attachment site of an angiotensin peptide moiety. Second, the SH3 domain could associate with proline rich regions introduced into HBcAgs. Thus, SH3 domains and proline rich SH3 interaction sites could be inserted into either the same or different HBcAgs and used to form and stabilized dimers and multimers of the invention.

As evidenced by the aforementioned example, one of skill in the art would know how to form a molecular scaffold comprising core particles and a first attachment site from HBcAg and HBcAg-derived muteins. By application of art-known techniques and routine experimentation, it would be understood by one of ordinary skill how other viruses could be similarly used to construct a molecular scaffold.

As presented elsewhere herein, viral capsids may be used for (1) the presentation of one or more angiotensin peptide moieties and (2) the preparation of vaccine conjugates of the invention. Particularly, useful in the practice of the invention are viral capsid proteins, also referred to herein as "coat proteins," which upon expression form capsids or capsid-like structures. Thus, these capsid proteins can form core particles and non-natural molecular scaffolds. Generally, these capsids or capsid-like structures form ordered and repetitive arrays which can be used for the presentation of antigenic determinants and the preparation of vaccine conjugates of the invention.

One or more (e.g., one, two, three, four, five, etc.) angiotensin peptide moieties may be attached by any number of means to one or more (e.g., one, two, three, four, five, etc.) proteins which form viral capsids or capsid-like structures (e.g., bacteriophage coat proteins), as well as other proteins. For example, angiotensin peptide moieties may be attached to core particles using first and second attachment sites. Further, one or more (e.g., one, two, three, four, five, etc.) heterobifunctional crosslinkers can be used to attach one or more angiotensin peptide moieties to one or more proteins which form viral capsids or capsid-like structures.

Viral capsid proteins, or fragments thereof may be used, for example, to prepare core particles and vaccine conjugates of the invention. Bacteriophage Qβ coat proteins, for example, can be expressed recombinantly in *E. coli*. Further, upon such expression these proteins spontaneously form capsids, which are virus-like particles. Additionally, these capsids form ordered and repetitive antigen arrays which can be used in presentation of angiotensin peptide moieties and the preparation of vaccine conjugates.

In a preferred embodiment, the virus-like particle comprises, consists essentially of, or alternatively consists of recombinant proteins, or fragments thereof, of a RNA-phage. Preferably, the RNA-phage is selected from the group consisting of a) bacteriophage Qβ; b) bacteriophage R17; c) bacteriophage fr; d) bacteriophage GA; e) bacteriophage SP; f) bacteriophage MS2; g) bacteriophage M11; h) bacteriophage MX1; i) bacteriophage NL95; k) bacteriophage f2; l) bacteriophage PP7, and m) bacteriophage AP205.

In another preferred embodiment of the present invention, the virus-like particle comprises, or alternatively consists essentially of, or alternatively consists of recombinant proteins, or fragments thereof, of the RNA-bacteriophage Qβ or of the RNA-bacteriophage fr or of the RNA-bacteriophage AP205.

Specific examples of bacteriophage coat proteins which can be used to prepare conjugates of the invention include the coat proteins of RNA bacteriophages such as bacteriophage Qβ (SEQ ID NO:3; PIR Database, Accession No. VCBPQβ referring to Qβ CP and SEQ ID NO: 4; Accession No. AAA16663 referring to Qβ A1 protein), bacteriophage R17 (PR Accession No. VCBPR7), bacteriophage fr (PIR Accession No. VCBPFR), bacteriophage GA (GenBank Accession No. NP-040754), bacteriophage SP (GenBank Accession No. CAA30374 referring to SP CP and Accession No. referring to SP A1 protein), bacteriophage MS2 (PIR Accession No. VCBPM2), bacteriophage M11 (GenBank Accession No. AAC06250), bacteriophage MX1 (GenBank Accession No. AAC14699), bacteriophage NL95 (GenBank Accession No. AAC14704), bacteriophage f2 (GenBank Accession No. P03611), bacteriophage PP7, bacteriophage AP205 (SEQ ID NO:12). As one skilled in the art would recognize, any protein which forms capsids or capsid-like structures can be used for the preparation of vaccine conjugates of the invention. Furthermore, the A1 protein of bacteriophage Qβ (Genbank accession No. AAA16663 (SEQ ID NO: 4)) or C-terminal truncated forms missing as much as about 100, about 150 or about 180 amino acids from its C-terminus may be incorporated in a capsid assembly of Qβ coat proteins. The A1 protein may also be fused an element containing a first attachment site, for attachment of angiotensin peptide moieties containing a second attachment site. Generally, the percentage of A1 protein relative to Qβ CP in the capsid assembly will be limited, in order to insure capsid formation.

Qβ coat protein has also been found to self-assemble into capsids when expressed in *E. coli* (Kozlovska T M. et al., *GENE* 137: 133–137 (1993)). The obtained capsids or virus-like particles showed an icosahedral phage-like capsid structure with a diameter of 25 nm and T=3 quasi symmetry. Further, the crystal structure of phage Qβ has been solved. The capsid contains 180 copies of the coat protein, which are linked in covalent pentamers and hexamers by disulfide bridges (Golmohammadi, R. et al., *Structure* 4: 543–5554 (1996)). Other RNA phage coat proteins have also been shown to self-assemble upon expression in a bacterial host (Kastelein, R A. et al., *Gene* 23: 245–254 (1983), Kozlovskaya, T M. et al., *Dokl. Akad. Nauk SSSR* 287: 452–455 (1986), Adhin, M R. et al., *Virology* 170: 238–242 (1989), Ni, CZ., et al., *Protein Sci.* 5: 2485–2493 (1996), Priano, C. et al., J. Mol. Biol. 249: 283–297 (1995)). The Qβ phage capsid contains, in addition to the coat protein, the so called read-through protein A1 and the maturation protein A2. A1 is generated by suppression at the UGA stop codon and has a length of 329 aa. The capsid of phage Qβ recombinant coat protein used in the invention is devoid of the A2 lysis protein, and contains RNA from the host. The coat protein of RNA phages is an RNA binding protein, and interacts with the stem loop of the ribosomal binding site of the replicase gene acting as a translational repressor during the life cycle of the virus. The sequence and structural elements of the interaction are known (Witherell, G W. & Uhlenbeck, O C. *Biochemistry* 28: 71–76 (1989); Lim F. et al., *J. Biol. Chem.* 271: 31839–31845 (1996)). The stem loop and RNA in general are known to be involved in the virus assembly (Golmohammadi, R. et al., *Structure* 4: 543–5554 (1996).)

Upon expression in *E. coli*, the N-terminal methionine of Qβ coat protein is usually removed, as we observed by N-terminal Edman sequencing as described in Stoll, E. et al. *J. Biol. Chem.* 252:990–993 (1977). VLP composed from Qβ coat proteins where the N-terminal methionine has not been removed, or VLPs comprising a mixture of Qβ coat proteins where the N-terminal methionine is either cleaved or present are also within the scope of the present invention. In a further preferred embodiment of the present invention, the virus-like particle comprises, or alternatively essentially consists of, or alternatively consists of recombinant proteins, or fragments thereof, of RNA-phage AP205.

The AP205 genome consists of a maturation protein, a coat protein, a replicase and two open reading frames not present in related phages; a lysis gene and an open reading frame playing a role in the translation of the maturation gene (Klovins, J., et al., J. Gen. Virol. 83: 1523–33 (2002)). AP205 coat protein can be expressed from plasmid pAP283-58 (SEQ ID NO: 11), which is a derivative of pQb10 (Kozlovska, T. M. et al., Gene 137:133–37 (1993)), and which contains an AP205 ribosomal binding site. Alternatively, AP205 coat protein may be cloned into pQb185, downstream of the ribosomal binding site present in the vector. Both approaches lead to expression of the protein and formation of capsids as described in the co-pending U.S. Provisional Appl. No. 60/396,126, filed July 17, 2002, which is incorporated by reference in its entirety, and in particular as described in Example 2 of said patent application. Vectors pQb10 and pQb185 are vectors derived from pGEM vector, and expression of the cloned genes in these vectors is controlled by the tip promoter (Kozlovska, T. M. et al., Gene 137:133–37 (1993)). Plasmid pAP283-58 (SEQ ID NO:1) comprises a putative AP205 ribosomal binding site in the following sequence, which is downstream of the XbaI site, and immediately upstream of the ATG start codon of the AP205 coat protein: tctagaATTTTCTGCGCACCCAT CCCGGGTGGCGCCCAAAGTGAGGAAAATCACatg.

The vector pQb185 comprises a Shine Delagarno sequence downstream from the XbaI site and upstream of the start codon (tctagaTTAACCCAACGCGTAGGAG TCAGGC-Catg, Shine Delagarno sequence underlined, SEQ ID NO: 18).

In a further preferred embodiment of the present invention, the virus-like particle comprises, or alternatively essentially consists of, or alternatively consists of recombinant coat proteins, or fragments thereof, of the RNA-phage AP205.

This preferred embodiment of the present invention, thus, comprises AP205 coat proteins that form capsids. Such proteins are recombinantly expressed, or prepared from natural sources. AP205 coat proteins produced in bacteria spontaneously form capsids, as evidenced by Electron Microscopy (EM) and immunodiffusion. The structural properties of the capsid formed by the AP205 coat protein (SEQ ID NO: 12) and those formed by the coat protein of the AP205 RNA phage are nearly indistinguishable when seen in EM. AP205 VLPs are highly immunogenic, and can be linked with antigens and/or antigenic determinants to generate vaccine constructs displaying the antigens and/or antigenic determinants oriented in a repetitive manner. High titers are elicited against the so displayed antigens showing that bound antigens and/or antigenic determinants are accessible for interacting with antibody molecules and are immunogenic.

In a further preferred embodiment of the present invention, the virus-like particle comprises, or alternatively essentially consists of, or alternatively consists of recombinant mutant coat proteins, or fragments thereof, of the RNA-phage AP205.

Assembly-competent mutant forms of AP205 VLPs, including AP205 coat protein with the subsitution of proline at amino acid 5 to threonine (SEQ ID NO: 13), may also be used in the practice of the invention and leads to a further preferred embodiment of the invention. These VLPs, AP205 VLPs derived from natural sources, or AP205 viral particles, may be bound to antigens to produce ordered repetitive arrays of the antigens in accordance with the present invention.

AP205 P5-T mutant coat protein can be expressed from plasmid pAP281-32 (SEQ ID No. 14), which is derived directly from pQb185, and which contains the mutant AP205 coat protein gene instead of the Qβ coat protein gene. Vectors for expression of the AP205 coat protein are transfected into E. coli for expression of the AP205 coat protein.

Methods for expression of the coat protein and the mutant coat protein, respectively, leading to self-assembly into VLPs are described in co-pending U.S. Provisional Appl. No. 60/396,126, filed Jul. 17, 2002, which is incorporated by reference in its entirety. Suitable E. coli strains include, but are not limited to, E. coli K802, JM 109, RR1. Suitable vectors and strains and combinations thereof can be identified by testing expression of the coat protein and mutant coat protein, respectively, by SDS-PAGE and capsid formation and assembly by optionally first purifying the capsids by gel filtration and subsequently testing them in an immunodiffusion assay (Ouchterlony test) or Electron Microscopy (Kozlovska, T. M. et al., Gene 137:133–37 (1993)).

AP205 coat proteins expressed from the vectors pAP283-58 and pAP281-32 may be devoid of the initial Methionine amino acid, due to processing in the cytoplasm of E. coli. Cleaved, uncleaved forms of AP205 VLP, or mixtures thereof are further preferred embodiments of the invention.

In a further preferred embodiment of the present invention, the virus-like particle comprises, or alternatively essentially consists of, or alternatively consists of a mixture of recombinant coat proteins, or fragments thereof, of the RNA-phage AP205 and of recombinant mutant coat proteins, or fragments thereof, of the RNA-phage AP205.

In a further preferred embodiment of the present invention, the virus-like particle comprises, or alternatively essentially consists of, or alternatively consists of fragments of recombinant coat proteins or recombinant mutant coat proteins of the RNA-phage AP205.

Recombinant AP205 coat protein fragments capable of assembling into a VLP and a capsid, respectively are also useful in the practice of the invention. These fragments may be generated by deletion, either internally or at the termini of the coat protein and mutant coat protein, respectively. Insertions in the coat protein and mutant coat protein sequence or fusions of antigen sequences to the coat protein and mutant coat protein sequence, and compatible with assembly into a VLP, are further embodiments of the invention and lead to chimeric AP205 coat proteins, and particles, respectively. The outcome of insertions, deletions and fusions to the coat protein sequence and whether it is compatible with assembly into a VLP can be determined by electron microscopy.

The particles formed by the AP205 coat protein, coat protein fragments and chimeric coat proteins described above, can be isolated in pure form by a combination of fractionation steps by precipitation and of purification steps by gel filtration using e.g. Sepharose CL-4B, Sepharose CL-2B, Sepharose CL-6B columns and combinations thereof as described in the co-pending U.S. Provisional Appl. No. 60/396,126, filed Jul. 17, 2002, which is incorporated by reference in its entirety. Other methods of isolating virus-like particles are known in the art, and may be used to isolate the virus-like particles (VLPs) of bacteriophage AP205. For example, the use of ultracentrifugation to isolate VLPs of the yeast retrotransposon Ty is described in U.S. Pat. No. 4,918,166, which is incorporated by reference herein in its entirety.

According to the present invention, one or more angiotensin peptide moieties may be attached to one subunit of the capsid of RNA phages coat proteins. The ability to couple several angiotensin peptide moieties per subunit of the capsid of the coat protein of RNA phages and in particular of Qβ capsid allows for the generation of a dense angiotensin peptide moiety array. Other viral capsids may be used for covalent attachment of angiotensin peptide moieties by way of chemical cross-linking, such for example a HBcAg modified with a lysine residue in its major immunodominant region (MIR; WO 00/32227). The distance between the spikes (corresponding to the MIR) of HBcAg is 50 Angstroms (Wynne, S A. et al., *Mol. Cell* 3: 771–780 (1999)), and therefore an angiotensin peptide moiety array with distances shorter than 50 A cannot be generated.

Capsids of Qβ coat protein display a defined number of lysine residues on their surface, with a defined topology with three lysine residues pointing towards the interior of the capsid and interacting with the RNA, and four other lysine residues exposed to the exterior of the capsid. These defined properties favor the attachment of angiotensin peptide moieties to the exterior of the particle, and not to the interior where the lysine residues interact with RNA. Capsids of other RNA phage coat proteins also have a defined number of lysine residues on their surface and a defined topology of these lysine residues. Another advantage of the capsids derived from RNA phages is their high expression yield in bacteria, that allows the production of large quantities of material at affordable cost.

Another feature of the capsid of Qβ coat protein is its stability. Qβ subunits are bound via disulfide bridges to each other, covalently linking the subunits. Qβ capsid protein also shows unusual resistance to organic solvents and denaturing agents. Surprisingly, we have observed that DMSO and acetonitrile concentrations as high as about 30%, and Guanidinium concentrations as high as about 1 M could be used without affecting the stability or the ability to form angiotensin peptide moiety arrays of the capsid. Thus, theses organic solvents may be used to couple hydrophobic molecules, such as certain angiotensin peptide moieties. The high stability of the capsid of Qβ coat protein is an important feature pertaining to its use for immunization and vaccination of mammals and humans in particular. The resistance of the capsid to organic solvent allows the coupling of angiotensin peptide moieties or deriviatives thereof that are not soluble in aqueous buffers.

Insertion of a cysteine residue into the N-terminal α-hairpin of the coat protein of the RNA phage MS-2 has been described in the U.S. Pat. No. 5,698,424, which is incorporated by reference herein in its entirety. We note however, that the presence of an exposed free cysteine residue in the capsid may lead to oligomerization of capsids by way of disulfide bridge formation. Other attachments contemplated in the above U.S. patent involve the formation of disulfide bridges between the angiotensin peptide moieties and the Qβ particle. Such attachments are labile to sulfhydryl-moiety containing molecules.

The reaction between an initial disulfide bridge formed with a cysteine-residue on Qβ, and the antigen containing a free sulfhydryl residue releases sulfhydryl containing species other than the angiotensin peptide moiety. These newly formed sulfhydryl containing species can react again with other disulfide bridges present on the particle, thus establishing an equilibrium. Upon reaction with the disulfide bridge formed on the particle, the angiotensin peptide moiety may either form a disulfide bridge with the cysteine-residue from the particle, or with the cysteine-residue of the leaving group molecule which was forming the initial disulfide bridge on the particle. Moreover, the other method of attachment described, using a hetero-bifunctional cross-linker reacting with a cysteine on the Qβ particle on one side, and with a lysine residue on the angiotensin peptide moiety on the other side, may lead to a random orientation of the angiotensin peptide moieties on the particle.

We further note that, in contrast to the capsid of the Qβ and Fr coat proteins, recombinant MS-2 described in U.S. Pat. No. 5,698,424 is essentially free of nucleic acids, while RNA is packaged inside the two capsids mentioned above.

We describe here new and inventive conjugates and conjugates allowing the formation of robust arrays of angiotensin peptide moieties, with variable density of angiotensin epitopes in the conjugates. We show that very high epitope density can be achieved by attaching angiotensin peptide moieties to VLPs. Further, the density and spacing of angiotensin peptide moieties can be modified by alterations in the number and type of residues with suitable first attachment sites. For example copending U.S. patent application Ser. No. 10/050,902, filed Jan. 18, 2002, discloses a Qβ mutant coat protein with additional lysine residues, suitable for obtaining higher density arrays than observed with wild type Qβ coat protein. Further, the aforesaid application also discloses conjugates suitable for simultaneous display of several antigens with appropriate spacing, and conjugates wherein the addition of accessory molecules, enhancing solubility or modifiying the capsid in a suitable and desired way. Other Qβ coat protein mutants, forming capsids, which are virus-like particles, are disclosed in copending U.S. patent application Ser. No. 10/050,902, and are suitable for generating compositions of the invention. In particular, in occurrences where solubility of the angiotensin peptide moiety, and of the Qβ-angiotensin peptide antigen array imposes a limit on the number of angiotensin peptide moieties that can be attached on the Qβ virus-like particle, mutants where lysine residues have been substituted for arginines, which do not have the same reactivity as lysine residues, can be used. When preparing these compositions, a high concentration of angiotensin peptide moiety, or angiotensin peptide moiety modified to comprise a second attachment site, can be used to achieve complete reaction at the lysine residues on the mutant Qβ virus-like particles, without generating potentially insoluble particles with a higher number of attached angiotensin peptide moieties, as would be the case when using the wt Qβ virus-like particle.

The crystal structure of several RNA bacteriophages has been determined (Golmohammadi, R. et al., *Structure* 4:543–554 (1996)). Using such information, one skilled in the art could readily identify surface exposed residues and modify bacteriophage coat proteins such that one or more reactive amino acid residues can be inserted. Thus, one skilled in the art could readily generate and identify modified forms of bacteriophage coat proteins which can be used in the practice of the invention. Thus, variants of proteins which form capsids or capsid-like structures (e.g., coat proteins of bacteriophage Qβ, bacteriophage R17, bacteriophage fr, bacteriophage GA, bacteriophage SP, and bacteriophage MS2) can also be used to prepare vaccine conjugates of the invention.

Although the sequence of the variants proteins discussed above will differ from their wild-type counterparts, these variant proteins will generally retain the ability to form capsids or capsid-like structures. Thus, the invention further includes vaccine conjugates which contain variants of proteins which form capsids or capsid-like structures, as well as methods for preparing such vaccine conjugates, individual protein subunits used to prepare such vaccine conjugates. Thus, included within the scope of the invention are variant forms of wild-type proteins which form ordered and repetitive arrays (e.g., variants of proteins which form capsids or capsid-like structures) and retain the ability to associate and form capsids or capsid-like structures. Normally, C- an N-terminal trunction variants retain the ability to form virus like particles. As a result, variant forms including deletion, addition, or subsitution, chimeric forms, and naturally occuring variants are suitable components of the invention.

Bacterial Pili and pilin proteins. In other embodiments, a bacterial pilin, a subportion of a bacterial pilin, or a fusion protein which contains either a bacterial pilin or subportion thereof is used to prepare vaccine conjugates of the invention. Examples of pilin proteins include pilins produced by *Escherichia coli, Haemophilus influenzae, Neisseria meningitidis, Neisseria gonorrhoeae, Caulobacter crescentus, Pseudomonas stutzeri*, and *Pseudomonas aeruginosa*. The amino acid sequences of pilin proteins suitable for use with the present invention include those set out in GenBank reports AJ000636, AJ132364, AF229646, AF051814, AF051815, and X00981, the entire disclosures of which are incorporated herein by reference.

Bacterial pilin proteins are generally processed to remove N-terminal leader sequences prior to export of the proteins into the bacterial periplasm. Further, as one skilled in the art would recognize, bacterial pilin proteins used to prepare vaccine conjugates of the invention will generally not have the naturally present leader sequence.

One specific example of a pilin protein suitable for use in the present invention is the P-pilin of *E. coli* (GenBank report AF237482). An example of a Type-1 *E. coli* pilin suitable for use with the invention is a pilin having the amino acid sequence set out in GenBank report P04128 (SEQ ID NO:2), which is encoded by nucleic acid having the nucleotide sequence set out in GenBank report M27603. The entire disclosures of these GenBank reports are incorporated herein by reference. Again, the mature form of the above referenced protein would generally be used to prepare vaccine conjugates of the invention.

Bacterial pilins or pilin subportions suitable for use in the practice of the present invention will generally be able to associate to form non-natural molecular scaffolds. Methods for preparing pili and pilus-like structures in vitro are known in the art. Bullitt et al., *Proc. Natl. Acad. Sci. USA* 93:12890–12895 (1996), for example, describe the in vitro reconstitution of *E. coli* P-pili subunits. Further, Eshdat et al (*J. Bacteriol*. 148:308–314 (1981)) describe methods suitable for dissociating Type-1 pili of *E. coli* and the reconstitution of pili. In brief, these methods are as follows: pili are dissociated by incubation at 37° C. in saturated guanidine hydrochloride. Pilin proteins are then purified by chromatography, after which pilin dimers are formed by dialysis against 5 mM tris(hydroxymethyl) aminomethane hydrochloride (pH 8.0). Eshdat et al. also found that pilin dimers reassemble to form pili upon dialysis against the 5 mM tris(hydroxymethyl) aminomethane (pH 8.0) containing 5 mM $MgCl_2$.

Further, using, for example, conventional genetic engineering and protein modification methods, pilin proteins may be modified to contain a first attachment site to which an angiotensin peptide moiety is linked through a second attachment site. Alternatively, angiotensin peptide moieties can be directly linked through a second attachment site to amino acid residues which are naturally resident in these proteins. These modified pilin proteins may then be used in immunizing conjugates of the invention.

Bacterial pilin proteins used to prepare conjugates of the invention may be modified in a manner similar to that described herein for HBcAg. For example, cysteine and lysine residues may be either deleted or substituted with other amino acid residues and first attachment sites may be added to these proteins. Further, pilin proteins may either be expressed in modified form or may be chemically modified after expression. Similarly, intact pili may be harvested from bacteria and then modified chemically.

In another embodiment, pili or pilus-like structures are harvested from bacteria (e.g., *E. coli*) and used to form vaccine conjugates of the invention. One example of pili suitable for preparing vaccine conjugates is the Type-1 pilus of *E. coli*, which is formed from pilin monomers having the amino acid sequence set out in SEQ ID NO:2.

A number of methods for harvesting bacterial pili are known in the art. Bullitt and Makowski (*Biophys. J.* 74:623–632 (1998)), for example, describe a pilus purification method for harvesting P-pili from *E. coli*. According to this method, pili are sheared from hyperpiliated *E. coli* containing a P-pilus plasmid and purified by cycles of solubilization and $MgCl_2$ (1.0 M) precipitation. Copending U.S. patent application Ser. No. 10/050,902, filed Jan. 18, 2002, discloses harvesting and purification of Type I pili from bacteria that naturally produce pili, or into which a vector has been introduced encoding the fim operon responsible for pilus production.

Once harvested, pili or pilus-like structures may be modified in a variety of ways. For example, a first attachment site can be added to the pili to which one or more angiotensin peptide moieties may be attached through a second attachment site. In other words, bacterial pil or pilus-like structures can be harvested and modified to form non-natural molecular scaffolds.

Pili or pilus-like structures may also be modified by the attachment of angiotensin peptide moieties in the absence of a non-natural first attachment site. For example, antigens or antigenic determinants could be linked to naturally occurring cysteine resides or lysine residues. In such instances, the high order and repetitiveness of a naturally occurring amino acid residue would guide the coupling of the angiotensin peptide moieties to the pili or pilus-like structures. For example, the pili or pilus-like structures could be linked to the second attachment sites of the angiotensin peptide moieties using a heterobifunctional cross-linking agent.

When structures which are naturally synthesized by organisms (e.g., pili) are used to prepare vaccine conjugates of the invention, it will often be advantageous to genetically engineer these organisms so that they produce structures having desirable characteristics. For example, when Type-1 pili of *E. coli* are used, the *E. coli* from which these pili are harvested may be modified so as to produce structures with specific characteristics. Examples of possible modifications of pilin proteins include the insertion of one or more lysine residues, the deletion or substitution of one or more of the naturally resident lysine residues, and the deletion or substitution of one or more naturally resident cysteine residues (e.g., the cysteine residues at positions 44 and 84 in SEQ ID NO:2).

Further, additional modifications can be made to pilin genes which result in the expression products containing a first attachment site other than a lysine residue (e.g., a FOS or JUN domain). Of course, suitable first attachment sites will generally be limited to those which do not prevent pilin proteins from forming pili or pilus-like structures suitable for use in vaccine conjugates of the invention. The ability of recombinant pilin proteins to form pili may be determined by a number of methods including electron microscopy.

Pilin genes which naturally reside in bacterial cells can be modified in vivo (e.g., by homologous recombination) or pilin genes with particular characteristics can be inserted into these cells. For examples, pilin genes could be introduced into bacterial cells as a component of either a replicable cloning vector or a vector which inserts into the bacterial chromosome. The inserted pilin genes may also be linked to expression regulatory control sequences (e.g., a lac operator).

In most instances, the pili or pilus-like structures used in vaccine conjugates of the invention will be composed of single type of a pilin subunit. However, the conjugates of the invention also include vaccines comprising pili or pilus-like structures formed from heterogenous pilin subunits. Pili or pilus-like structures composed of identical subunits will generally be used because they are expected to form structures which present highly ordered and repetitive antigen arrays.

Second attachment site. The preparation of molecular scaffolds with ordered and repetitive arrays is provided by the present including conjugates of capsids of RNA phage coat proteins with a high epitope density. The nature of the angiotensin peptide moiety, and nature and location of the second attachment site on the moiety are important factors that may influence the means available to construct conjugates of the invention, and the effectiveness of those conjugates in inducing an immune response, as is understood by those of ordinary skill in the art.

A prerequisite for designing a second attachment site is the choice of the position at which it should be fused, inserted or generally engineered or attached. A skilled artisan would know how to find guidance in selecting the position of the second attachment site, and many factors may be considered relevant to this decision. The chemical and/or crystal structure of the angiotensin peptide moiety may provide information on the availability of domains on the molecule suitable for coupling. A reactive domain's accessibility to solvent may be a limiting factor in the kinetics of chemical coupling to a first attachment site. Groups suitable for coupling must be available, such as sulfhydryl residues. In general, in the case where immunization with an angiotensin peptide moiety is aimed at inhibiting the interaction of the angiotensin peptide moiety, which may also be a self-antigen with its natural ligands, such as a substrate or a receptor, the second attachment site will be added such that it allows generation of antibodies against the site of interaction with the natural ligands. Thus, the location of the second attachment site will selected such, that steric hindrance from the second attachment site or any amino acid linker containing it, is avoided. In further embodiments, an antibody response directed at a site distinct from the interaction site of the antigen with its natural ligand is desired. In such embodiments, the second attachment site may be selected such that it prevents generation of antibodies against the interaction site of the antigen with its natural ligands. Other factors of consideration include the nature of the angiotensin peptide moiety, its biochemical properties, such as pI, charge distribution, further modification. In general, flexible linkers are favored.

Other criteria in selecting the position of the second attachment site include the oligomerization state of the angiotensin peptide moiety, the site of oligomerization, the presence of a cofactor, and the availability of experimental evidence disclosing sites in the moiety structure and sequence where modification of the moiety is compatible with the function moiety, or with the generation of antibodies recognizing the moiety and preferably, blocking function of the angiotensin peptide moiety. In certain embodiments, one or more additional amino acids (leading to a non-naturally occurring second attachment site) are added either at the C- or at the N-terminus of the angiotensin peptide moiety sequences in order to assure, in particular, an oriented and ordered association of the angiotensin peptide moiety to the virus-like particle in accordance with the present invention.

A particularly favored method of attachment of polypeptide antigens to VLPs, and in particular to capsids of RNA phage coat proteins, is the linking of a lysine residue on the surface of the capsid of RNA phage coat proteins with a sulfhydryl group residue on the antigen, such as is found in cysteine residues. Similarly, free sulfhydryl groups on angiotensin peptide moieties may also be effective attachment sites. Where an oxidized sulfhydryl groups must be in a reduced state in order to function as a second attachment site, reduction may be achieved with e.g. DTT, TCEP or β-mercaptoethanol.

According to the present invention, the epitope density on the capsid of RNA phage coat proteins can be modulated by the choice of cross-linker and other reaction conditions. For example, the cross-linkers Sulfo-GMBS and SMPH allow reaching high epitope density. Derivatization is positively influenced by high concentration of reactants, and manipulation of the reaction conditions can be used to control the number of antigens coupled to RNA phages capsid proteins, and in particular to Qβ capsid protein. In addition, the number of first attachment sites on the core particle is another factor affecting the density of the angiotensin peptide moiety array. In one embodiment of the present invention, we provide a Qβ mutant coat protein with additional lysine residues, suitable for obtaining higher density arrays.

In the most preferred embodiments, the angiotensin peptide moiety comprises a single second attachment site or a single reactive attachment site capable of association with the first attachment sites on the core particle and the VLPs or VLP subunits, respectively. This ensures a defined and uniform binding and association, respectively, of the at least one, but typically more than one, preferably more than 10, 20, 40, 80, 120 antigens to the core particle and VLP, respectively. The provision of a single second attachment site or a single reactive attachment site on the antigen, thus, ensures a single and uniform type of binding and association, respectively leading to a very highly ordered and repetitive array. For example, if the binding and association, respectively, is effected by way of a lysine—(as the first attachment site) and cysteine—(as a second attachment site) interaction, it is ensured, in accordance with this preferred embodiment of the invention, that only one cysteine residue per antigen, independent whether this cysteine residue is naturally or non-naturally present on the antigen, is capable of binding and associating, respectively, with the VLP and the first attachment site of the core particle, respectively.

In a further preferred embodiment of the invention, the covalent is a non-peptide bond.

In some embodiments, engineering of a second attachment site onto the antigen require the fusion of an amino acid linker containing an amino acid suitable as second attachment site according to the disclosures of this invention. Therefore, in a preferred embodiment of the present invention, an amino acid linker is bound to the antigen or the antigenic determinant by way of at least one covalent bond. Preferably, the amino acid linker comprises, or alternatively consists of, the second attachment site. In a further preferred embodiment, the amino acid linker comprises a sulfhydryl group or a cysteine residue. In another preferred embodiment, the amino acid linker is cysteine. Some criteria of selection of the amino acid linker as well as further preferred embodiments of the amino acid linker according to the invention have already mentioned above.

In a further preferred embodiment of the invention, the at least one antigen or antigenic determinant, i.e. the PrP protein, PrP peptide or the PrP domain is fused to the core particle and the virus-like particle, respectively. As outlined above, a VLP is typically composed of at least one subunit assembling into a VLP. Thus, in again a further preferred embodiment of the invention, the antigen or antigenic determinant, preferably the at least one angiotensin peptide moiety, is fused to at least one subunit of the virus-like particle or of a protein capable of being incorporated into a VLP generating a chimeric VLP-subunit-angiotensin peptide moiety fusion.

Fusion of the angiotensin peptide moieties can be effected by insertion into the VLP subunit sequence, or by fusion to either the N- or C-terminus of the VLP-subunit or protein capable of being incorporated into a VLP. Hereinafter, when referring to fusion proteins of a peptide to a VLP subunit, the fusion to either ends of the subunit sequence or internal insertion of the peptide within the subunit sequence are encompassed.

Fusion may also be effected by inserting the angiotensin peptide moiety sequences into a variant of a VLP subunit where part of the subunit sequence has been deleted, that are further referred to as truncation mutants. Truncation mutants may have N- or C-terminal, or internal deletions of part of the sequence of the VLP subunit. For example, the specific VLP HBcAg with, for example, deletion of amino acid residues 79 to 81 is a truncation mutant with an internal deletion. Fusion of angiotensin peptide moieties to either the N- or C-terminus of the truncation mutants VLP-subunits also lead to embodiments of the invention. Likewise, fusion of an epitope into the sequence of the VLP subunit may also be effected by substitution, where for example for the specific VLP HBcAg, amino acids 79–81 are replaced with a foreign epitope. Thus, fusion, as referred to hereinafter, may be effected by insertion of the angiotensin peptide moiety sequence in the sequence of a VLP subunit, by substitution of part of the sequence of the VLP subunit with the angiotensin peptide moiety sequence, or by a combination of deletion, substitution or insertions.

The chimeric angiotensin peptide moiety-VLP subunit will be in general capable of self-assembly into a VLP. VLP displaying epitopes fused to their subunits are also herein referred to as chimeric VLPs. As indicated, the virus-like particle comprises or alternatively is composed of at least one VLP subunit. In a further embodiment of the invention, the virus-like particle comprises or alternatively is composed of a mixture of chimeric VLP subunits and non-chimeric VLP subunits, i.e. VLP subunits not having an antigen fused thereto, leading to so called mosaic particles. This may be advantageous to ensure formation of and assembly to a VLP. In those embodiments, the proportion of chimeric VLP-subunits may be 1, 2, 5, 10, 20, 30, 40, 50, 60, 70, 80, 90, 95% or higher.

Flanking amino acid residues may be added to either end of the sequence of the peptide or epitope to be fused to either end of the sequence of the subunit of a VLP, or for internal insertion of such peptidic sequence into the sequence of the subunit of a VLP. Glycine and serine residues are particularly favored amino acids to be used in the flanking sequences added to the angiotensin peptide moiety to be fused. Glycine residues confer additional flexibility, which may diminish the potentially destabilizing effect of fusing a foreign sequence into the the sequence of a VLP subunit.

In a specific embodiment of the invention, the VLP is a Hepatitis B core antigen VLP. Fusion proteins to either the N-terminus of a HBcAg (Neyrinck, S. et al., *Nature Med.* 5:1157–1163 (1999)) or insertions in the so called major immunodominant region (MIR) have been described (Pumpens, P. and Grens, E., *Intervirology* 44:98–114 (2001)), WO 01/98333), and are preferred embodiments of the invention. Naturally occurring variants of HBcAg with deletions in the MIR have also been described (Pumpens, P. and Grens, E., *Intervirology* 44:98–114 (2001), which is expressly incorporated by reference in their entirety), and fusions to the N- or C-terminus, as well as insertions at the position of the MIR corresponding to the site of deletion as compared to a wt HBcAg are further embodiments of the invention. Fusions to the C-terminus have also been described (Pumpens, P. and Grens, E., *Intervirology* 44:98–114 (2001)). One skilled in the art will easily find guidance on how to construct fusion proteins using classical molecular biology techniques (Sambrook, J. et al., eds., *Molecular Cloning, A Laboratory Manual*, 2nd. edition, Cold Spring Habor Laboratory Press, Cold Spring Harbor, N.Y. (1989), Ho et al., *Gene* 77:51 (1989)). Vectors and plasmids encoding HBcAg and HBcAg fusion proteins and useful for the expression of a HBcAg and HBcAg fusion proteins have been described (Pumpens, P. & Grens, E. Intervirology 44: 98–114 (2001), Neyrinck, S. et al., *Nature Med.* 5:1157–1163 (1999)) and can be used in the practice of the invention. We also describe by way of example (Example 6) the insertion of an epitope into the MIR of HBcAg, resulting in a chimeric self-assembling HBcAg. An important factor for the optimization of the efficiency of self-assembly and of the display of the epitope to be inserted in the MIR of HBcAg is the choice of the insertion site, as well as the number of amino acids to be deleted from the HBcAg sequence within the MIR (Pumpens, P. and Grens, E., *Intervirology* 44:98–114 (2001); EP 0 421 635; U.S. Pat. No. 6,231,864) upon insertion, or in other words, which amino acids form HBcAg are to be substituted with the new epitope. For example, substitution of HBcAg amino acids 76–80, 79–81, 79–80, 75–85 or 80–81 with foreign epitopes has been described (Pumpens, P. and Grens, E., *Intervirology* 44:98–114 (2001); EP 0 421 635; U.S. Pat. No. 6,231, 864). HBcAg contains a long arginine tail (Pumpens, P. and Grens, E., *Intervirology* 44:98–114 (2001)) which is dispensable for capsid assembly and capable of binding nucleic acids (Pumpens, P. and Grens, E., *Intervirology* 44:98–114 (2001)). HBcAg either comprising or lacking this arginine tail are both embodiments of the invention.

In a further preferred embodiment of the invention, the VLP is a VLP of a RNA phage. The major coat proteins of RNA phages spontaneously assemble into VLPs upon expression in bacteria, and in particular in E. coli. Specific examples of bacteriophage coat proteins which can be used to prepare compositions of the invention include the coat proteins of RNA bacteriophages such as bacteriophage Qβ (SEQ ID NO:10; PIR Database, Accession No. VCBPQβ referring to Qβ CP and SEQ ID NO: 11; Accession No. AAA16663 referring to Qβ A1 protein) and bacteriophage fr (SEQ ID NO: 32; PIR Accession No. VCBPFR).

In a more preferred embodiment, the at least one angiotensin peptide moiety is fused to a Qβ coat protein. Fusion protein constructs wherein epitopes have been fused to the C-terminus of a truncated form of the A1 protein of Qβ, or inserted within the A1 protein have been described (Kozlovska, T. M., et al., *Intervirology*, 39:9–15 (1996)). The A1 protein is generated by suppression at the UGA stop codon and has a length of 329 aa, or 328 aa, if the cleavage of the N-terminal methionine is taken into account. Cleavage of the N-terminal methionine before an alanine (the second amino acid encoded by the Qβ CP gene) usually takes place in *E. coli*, and such is the case for N-termini of the Qβ coat proteins CP. The part of the A1 gene, 3' of the UGA amber codon encodes the CP extension, which has a length of 195 amino acids. Insertion of the at least one angiotensin peptide moiety between position 72 and 73 of the CP extension leads to further embodiments of the invention (Kozlovska, T. M., et al., *Intervirology* 39:9–15 (1996)). Fusion of a angiotensin peptide moiety at the C-terminus of a C-terminally truncated Qβ A1 protein leads to further preferred embodiments of the invention. For example, Kozlovska et al., (*Intervirology*, 39: 9–15 (1996)) describe Qβ A1 protein fusions where the epitope is fused at the C-terminus of the Qβ CP extension truncated at position 19.

As described by Kozlovska et al. (*Intervirology*, 39: 9–15 (1996)), assembly of the particles displaying the fused epitopes typically requires the presence of both the A1 protein-angiotensin peptide moiety fusion and the wt CP to form a mosaic particle. However, embodiments comprising virus-like particles, and hereby in particular the VLPs of the RNA phage Qβ coat protein, which are exclusively composed of VLP subunits having at least one angiotensin peptide moiety fused thereto, are also within the scope of the present invention.

The production of mosaic particles may be effected in a number of ways. Kozlovska et al., *Intervirolog*, 39:9–15 (1996), describe two methods, which both can be used in the practice of the invention. In the first approach, efficient display of the fused epitope on the VLPs is mediated by the expression of the plasmid encoding the Qβ A1 protein fusion having a UGA stop codong between CP and CP extension in a *E. coli* strain harboring a plasmid encoding a cloned UGA suppressor tRNA which leads to translation of the UGA codon into Trp (pISM3001 plasmid (Smiley B. K., et al., *Gene* 134:33–40 (1993))). In another approach, the CP gene stop codon is modified into UAA, and a second plasmid expressing the A1 protein-angiotensin peptide moiety fusion is cotransformed. The second plasmid encodes a different antibiotic resistance and the origin of replication is compatible with the first plasmid (Kozlovska, T. M., et al., *Intervirology* 39:9–15 (1996)). In a third approach, CP and the A1 protein-angiotensin peptide moiety fusion are encoded in a bicistronic manner, operatively linked to a promoter such as the Trp promoter, as described in FIG. 1 of Kozlovska et al., *Intervirology*, 39:9–15 (1996).

In a further embodiment, the angiotensin peptide moiety is inserted between amino acid 2 and 3 (numbering of the cleaved CP, that is wherein the N-terminal methionine is cleaved) of the fr CP, thus leading to a angiotensin peptide moiety -fr CP fusion protein. Vectors and expression systems for construction and expression of fr CP fusion proteins self-assembling to VLP and useful in the practice of the invention have been described (Pushko P. et al., *Prot. Eng.* 6:883–891 (1993)). In a specific embodiment, the angiotensin peptide moiety sequence is inserted into a deletion variant of the fr CP after amino acid 2, wherein residues 3 and 4 of the fr CP have been deleted (Pushko P. et al., *Prot. Eng.* 6:883–891 (1993)).

Fusion of epitopes in the N-terminal protuberant β-hairpin of the coat protein of RNA phage MS-2 and subsequent presentation of the fused epitope on the self-assembled VLP of RNA phage MS-2 has also been described (WO 92/13081), and fusion of angiotensin peptide moiety by insertion or substitution into the coat protein of MS-2 RNA phage is also falling under the scope of the invention.

In another embodiment of the invention, the angiotensin peptide moieties are fused to a capsid protein of papillomavirus. In a more specific embodiment, the angiotensin peptide moieties are fused to the major capsid protein L1 of bovine papillomavirus type I (BPV-1). Vectors and expression systems for construction and expression of BPV-1 fusion proteins in a baculovirus/insect cells systems have been described (Chackerian, B. et al., *Proc. Natl. Acad. Sci. USA* 96:2373–2378 (1999), WO 00/23955). Substitution of amino acids 130–136 of BPV-1 L1 with a angiotensin peptide moiety leads to a BPV-1 L1-angiotensin peptide moiety fusion protein, which is a preferred embodiment of the invention. Cloning in a baculovirus vector and expression in baculovirus infected Sf9 cells has been described, and can be used in the practice of the invention (Chackerian, B. et al., *Proc. Natl. Acad. Sci. USA* 96:2373–2378 (1999), WO 00/23955). Purification of the assembled particles displaying the fused angiotensin peptide moieties can be performed in a number of ways, such as for example gel filtration or sucrose gradient ultracentrifugation (Chackerian, B. et al., *Proc. Natl. Acad. Sci. USA* 96:2373–2378 (1999), WO 00/23955).

In a further embodiment of the invention, the angiotensin peptide moieties are fused to a Ty protein capable of being incorporated into a Ty VLP. In a more specific embodiment, the angiotensin peptide moieties are fused to the p1 or capsid protein encoded by the TYA gene (Roth, J. F., *Yeast* 16:785–795 (2000)). The yeast retrotransposons Ty1, 2, 3 and 4 have been isolated from *Saccharomyces Serevisiae*, while the retrotransposon Tf1 has been isolated from *Schizosaccharomyces* Pombae (Boeke, J. D. and Sandmeyer, S. B., "Yeast Transposable Elements," in *The Molecular and Cellular Biology of the Yeast Saccharomyces: Genome Dynamics, Protein Synthesis, and Energetics.*, p. 193, Cold Spring Harbor Laboratory Press (1991)). The retrotransposons Ty1 and 2 are related to the copia class of plant and animal elements, while Ty3 belongs to the gypsy family of retrotransposons, which is related to plants and animal retroviruses. In the Ty1 retrotransposon, the p1 protein, also referred to as Gag or capsid protein, has a length of 440 amino acids. P1 is cleaved during maturation of the VLP at position 408, leading to the p2 protein, the essential component of the VLP.

Fusion proteins to p1 and vectors for the expression of said fusion proteins in Yeast have been described (Adams, S. E., et al., *Nature* 329:68–70 (1987)). So, for example, a angiotensin peptide moiety may be fused to p1 by inserting a sequence coding for the angiotensin peptide moiety into the BamH1 site of the pMA5620 plasmid (Adams, S. E., et al., *Nature* 329:68–70 (1987)). The cloning of sequences coding for foreign epitopes into the pMA5620 vector leads to expression of fusion proteins comprising amino acids 1–381 of p1 of Ty1–15, fused C-terminally to the N-terminus of the foreign epitope. Likewise, N-terminal fusion of angiotensin peptide moieties, or internal insertion into the p1 sequence, or substitution of part of the p1 sequence is also meant to fall within the scope of the invention. In particular, insertion of angiotensin peptide moieties into the Ty sequence between amino acids 30–31, 67–68, 113–114 and 132–133 of the Ty protein p1 (EP0677111) leads to preferred embodiments of the invention.

Further VLPs suitable for fusion of angiotensin peptide moieties are, for example, Retrovirus-like-particles (WO9630523), HIV2 Gag (Kang, Y. C., et al, *Biol. Chem.* 380:353–364 (1999)), Cowpea Mosaic Virus (Taylor, K. M. et al., *Biol. Chem.* 380:387–392 (1999)), parvovirus VP2 VLP (Rueda, P. et al., *Virology* 263:89–99 (1999)), HBsAg (U.S. Pat. No. 4,722,840; EP 0 020 416 B1).

Examples of chimeric VLPs suitable for the practice of the invention are also those described in *Intervirology* 39:1

(1996). Further examples of VLPs contemplated for use in the invention are: HPV-1, HPV-6, HPV-11, HPV-16, HPV-18, HPV-33, HPV-45, CRPV, COPV, HIV GAG, Tobacco Mosaic Virus. Virus-like particles of SV-40, Polyomavirus, Adenovirus, Herpes Simplex Virus, Rotavirus and Norwalk virus have also been made, and chimeric VLPs of those VLPs are also within the scope of the present invention.

Cross linking. Methods for linking the angiotensin peptide moiety to the core particle are well within the working knowledge of the practitioner of ordinary skill in the art, and numerous references exist to aid such a practitioner (e.g., Sambrook, J. et al., eds., MOLECULAR CLONING, A LABORATORY MANUAL, $2^{nd}$. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997); Celis, J., ed., CELL BIOLGY, Academic Press, $2^{nd}$ edition, (1998); Harlow, E. and Lane, D., "Antibodies: A Laboratory Manual," Cold Spring Harbor Laboratory, Cold Spring Harbor, N.Y. (1988), all of which are incorporated herein by reference in their entirities.

Differing methods of achieving an association between the core particle and angiotensin peptide moieity are described herein and are further described in copending U.S. patent application Ser. No. 10/050,902, filed Jan. 18, 2002, which is incorporated by reference herein in its entirety. Methods include the JUN and FOS leucine zipper protein domains are utilized for the first and second attachment sites of the invention, respectively.

Preferred embodiments of the invention comprise the coupling of the non-natural molecular scaffold to the angiotensin peptide moiety by chemical cross-linking. There is a wide range of compounds which have been developed to facilitate cross-linking of proteins/peptides or conjugation of proteins to derivatized molecules, e.g., angiotensin peptide moieties. These include, but are not limited, to carboxylic acid derived active esters (activated compounds), mixed anhydrides, acyl halides, acyl azides, alkyl halides, N-maleimides, imino esters, isocyanates and isothiocyanates, which are known to those skilled in the art. These are capable of forming a covalent bond with a reactive group of a protein molecule. Depending upon the activating group, the reactive group is the amino group of a lysine residue on a protein molecule or a thiol group in a carrier protein or a modified carrier protein molecule which, when reacted, result in amide, amine, thioether, amidine urea or thiourea bond formation. One skilled in the art may identify further suitable activating groups, for example, in general reference texts such as Chemistry of Protein Conjugation and Cross-Linking (Wong (1991) CRC Press, Inc., Boca Raton, Fla.). Most reagents react preferentially with lysine side chain groups.

In some embodiments, the angiotensin peptide moiety is attached to the core particle by way of chemical cross-linking, using a heterobifunctional cross-linker. Several hetero-bifunctional cross-linkers are known in the art. In one embodiment, the hetero-bifunctional cross-linker contains a functional group which can react with the side-chain amino group of lysine residues of the core particle, and a functional group which can react with a cysteine residue or sulfhydryl group present, made available for reaction by reduction, or engineered on the angiotensin peptide moiety and optionally also made available for reaction by reduction. The first step of the procedure, called the derivatization, is the reaction of the core particle with the cross-linker. The product of this reaction is an activated core particle, also called activated carrier. In the second step, unreacted cross-linker is removed using usual methods such as gel filtration or dialysis. In the third step, the antigen (e.g., the angiotensin peptide moiety) is reacted with the activated core particle, and this step is called the coupling step. Unreacted antigen may be optionally removed in a fourth step.

In an alternative embodiment, the angiotensin peptide moiety is derivatized with an active moiety suitable for cross linking to the first attachment site, generating an activated angiotensin peptide moiety. Such derivatization may occur on an isolated angiotensin peptide moiety or via a chemical synthesis. The activated angiotensin peptide moiety is then reacted with the core particle such that coupling occurs.

Several hetero-bifunctional cross-linkers are known in the art. These include the cross-linkers SMPH (Pierce), Sulfo-MBS, Sulfo-EMCS, Sulfo-GMBS, Sulfo-SIAB, Sulfo-SMPB, Sulfo-SMCC, SVSB, SIA and other cross-linkers available, for example from the Pierce Chemical Company (Rockford, Ill., USA), and having one functional group reactive towards amino groups and one functional group reactive towards SH residues. The above mentioned cross-linkers all lead to formation of a thioether linkage. Another class of cross-linkers suitable in the practice of the invention is characterized by the introduction of a disulfide linkage between the angiotensin peptide moiety and the core particle upon coupling. Cross-linkers belonging to this class include for example SPDP and Sulfo-LC-SPDP (Pierce). The extent of derivatization of the core particle with cross-linker can be influenced by varying experimental conditions such as the concentration of each of the reaction partners, the excess of one reagent over the other, the pH, the temperature and the ionic strength, as is well known from reaction theory in the field of organic chemistry. The degree of coupling, i.e. the amount of angiotensin peptide moiety per carrier can be adjusted by varying the experimental conditions described above to match the requirements of the vaccine. Solubility of the angiotensin peptide moiety may impose a limitation on the amount of antigen that can be coupled on each subunit, and in those cases where the obtained vaccine is insoluble, reducing the amount of antigens per subunit is beneficial.

In one specific embodiment the chemical agent is the heterobifunctional cross-linking agent εε-maleimidocaproic acid N-hydroxysuccinimide ester (Tanimori et al., J. Pharm. Dyn. 4:812 (1981); Fujiwara et al., J. Immunol. Meth. 45:195 (1981)), which contains (1) a succinimide group reactive with amino groups and (2) a maleimide group reactive with SH groups. A heterologous protein or polypeptide of the first attachment site may be engineered to contain one or more lysine residues that will serve as a reactive moiety for the succinimide portion of the heterobifunctional cross-linking agent. Once chemically coupled to the lysine residues of the heterologous protein, the maleimide group of the heterobifunctional cross-linking agent will be available to react with the SH group of a cysteine residue on the antigen or antigenic determinant. Antigen or antigenic determinant preparation in this instance may require the engineering of a sulfhydryl residue as the second attachment site so that it may be reacted to the free maleimide function on the cross-linking agent bound to the non-natural molecular scaffold first attachment sites. Thus, in such an instance, the heterobifunctional cross-linking agent binds to a first attachment site of the non-natural molecular scaffold and connects the scaffold to a second binding site of the angiotensin peptide moiety.

Other methods of coupling the angiotensin peptide moiety to the core particle include methods wherein the angiotensin peptide moiety is cross-linked to the core particle using carbodiimide bonds. These include the carbodiimide EDC (1-(3-dimethylaminopropyl)-3-ethylcarbodiimide hydrochloride), and NHS. In one method, EDC is mixed with an angiotensin peptide moiety containing a free carboxylic acid, amino or amido moiety, then added to the protein carrier. In other methods, the moiety is attached to the core particle using a homo-bifunctional cross-linker such as glutaraldehyde, DSG, BM[PEO]$_4$, BS$^3$, (Pierce Chemical Company, Rockford, Ill., USA) or other known homo-bifunctional cross-linkers with functional groups reactive towards amine groups or carboxyl groups of the core particle.

Additional cross-linking methods and cross-linkers, suitable for attaching a hapten to a core particle and a virus-like particle, respectively, as well as guidance on performing the coupling reactions and on the use of chemical cross-linkers and chemical cross-linking procedures can be found in Hermanson, G. T. in *Bioconjugate Techniques*, Academic Press Inc., San Diego, Calif., USA.

Further methods of binding the core particle to an angiotensin peptide moiety include methods where the core particle is biotinylated, and the moiety fused to streptavidin, or methods wherein both the moiety and the core particle are biotinylated. In this case, the angiotensin peptide moiety may be first bound to streptavidin or avidin by adjusting the ratio of moiety to streptavidin such that free binding sites are still available for binding of the core particle, which is added in the next step. Alternatively, all components may be mixed in a "one pot" reaction. Other ligand-receptor pairs, where a soluble form of the receptor and of the ligand is available, and are capable of being cross-linked to the core particle or the angiotensin peptide moiety, may be used as binding agents for binding the angiotensin peptide moiety to the core particle.

Angiotensin Peptide Moieties

Thus, in one aspect, the invention provides ordered, repetitive arrays of angiotensin peptide moieties suitable for immunization against such moieties. Preferred angiotensin peptide moieties are those comprising, or alternatively consisting of, the sequence, or fragments thereof, of angiotensinogen, angiotensin I or angiotensin II. As noted above, one or more additional amino acids may be suitably added to either the C- or the N-terminus of the angiotensin peptide moiety sequences in order to assure, in particular, an oriented and ordered association of the angiotensin peptide moiety to the core particle.

Preferred angiotensin peptide moieties for use in the conjugates and conjugates of the invention are those comprising, or alternatively consisting of the full-length sequence of angiotensinogen, angiotensin I or angiotensin II. Preferably, the angiotensin peptide moieties comprise, or alternatively consist of, the full-length sequence of angiotensin II such as CGGDRVYIHPF (SEQ ID NO: 19, referred to herein as "Angio 1"; amino acids in addition to the angiotensin peptide sequence are indicated by italics), or the full-length sequence of angiotensin I, such as CGGDRVYIHPFHIL (SEQ ID NO: 20, "Angio 2"), DRVYIHPFHLGGC (SEQ ID NO: 21, "Angio 3"), and CDRVYIHPFHL (SEQ ID NO: 22, "Angio 4"). Further preferred embodiments are those angiotensin peptide moieties which comprise, or alternatively consist of, only a fragment of the sequences of angiotensinogen, angiotensin I or angiotensin II. Certain such embodiments include angiotensin peptide moieties which comprise, or alternatively consist of, at least three amino acids of the C-terminus of the angiotensin peptides and, in an alternative embodiment, from which at least four amino acids of the N-terminus have been deleted. Other related embodiments are those derived from angiotensin I such as CHPFHL (SEQ ID NO: 23, "Angio 5") and CGPFHL (SEQ ID NO: 24, "Angio 6"), or those derived from angiotensin II such as CYIHPF (SEQ ID NO: 25, "Angio 7"), CGIHPF (SEQ ID NO: 26, "Angio 8") and CGGHPF (SEQ ID NO: 27, "Angio 9").

Additional embodiments of the present invention use angiotensin peptide moieties which comprise, or alternatively consist of, at least three amino acids of the N-terminus of the angiotensin peptides and, for which, in a further preferred embodiment, at least four, preferably five, amino acids of the C-terminus have been deleted. Other related embodiments are DRVYIGGC (SEQ ID NO: 28, "Angio 13"), DRVYGGC (SEQ ID NO: 29, "Angio 14") and DRVGGC (SEQ ID NO: 30, "Angio 15").It will be understood by those of ordinary skill in the art, however, that the foregoing examples of angiotensin peptide moieties are non-limiting examples, and that the number and the nature of the amino acids added for coupling, either at C or N terminus, can vary.

In the present invention, it is not necessary that the immunizing angiotensin peptide moiety comprise an entire intact molecule of any particular angiotensin peptide moiety. Suitable immune responses against the angiotensin peptide moieties of interest may be generated by the use of fragments of the angiotensin peptide moiety, or derivatives, mutants or muteins thereof.

The invention embodies different sites of linkage and means of linkage of the angiotensin peptide moiety to the core particle, non-limiting examples of which are described elsewhere herein. Preferred sites and means of linkage may also be determined by the ordinarily skilled artisan on the basis of prior experience, theory and by routine experimentation.

Conjugates, Vaccines and Methods of Use

The invention thus provides conjugates which may be used for preventing and/or attenuating diseases or conditions associated with one or more components of the RAS, particularly one or more angiotensin peptide moieties. The invention further provides vaccination methods for preventing and/or attenuating diseases or conditions in individuals, particularly in animals such as mammals, and particularly humans. In a preferred embodiment, the conjugates and conjugates of the invention stimulate an immune response leading to the production of immune molecules, including antibodies, that bind to one or more angiotensin peptide moieties. The invention further provides vaccination methods for preventing and/or attenuating diseases or conditions associated with the RAS in individuals.

The nature or type of immune response is not a limiting factor of this disclosure. The desired outcome of a therapeutic or prophylactic immune response may vary according to the disease, according to principles well known in the art. Without the intention to limit the present invention by the following mechanistic explanation, the inventive conjugates might induce antibodies which bind to more than one angiotensin peptide species thereby blocking all relevant species of angiotensin at the same time. Alternatively the induced antibodies might bind specifically to the C-terminus of angiotensinogen, angiotensin I or angiotensin II. Under these conditions, the induced antibodies will block activation of angiotensinogen or angiotensin I by renin or ACE, respectively. Nevertheless, proteases different from ACE or renin such as endopeptidases and aminopeptidases can degrade angiotensinogen, angiotensin I or angiotensin II from the N-terminus thus preventing the accumulation of antibody-bound intact angiotensinogen, angiotensin I or angiotensin II.

Furthermore, it may be desired to stimulate different types of immune response depending on the disease, and according to principles known in the art. It is well known, for example, that some immune responses are more appropriate for a particular antigen than other immune responses. Some immune responses are, indeed, inappropriate and can cause pathology, such as pathologic inflammation.

The nature of the immune response can be affected by the nature of the antigen, route of introduction into the body, dose, dosage regimen, repetitive nature of the antigen, host background, and signaling factors of the immune system. Such knowledge is well known in the art. As such, an immune response may be tailored by the application of both art known theory and routine experimentation.

Furthermore, the invention embodies the use of differing core particles during the course of vaccination against angiotensin peptide moieties. Individuals who develop strong immune responses against core particles such as e.g. pili, may be immunized with conjugates comprising the same angiotensin peptide moiety but differing in core particle.

While not wishing to be bound by theory, the current conjugates of the present invention provide particular novel and surprising advantages as components of pharmaceutical conjugates to generate an immune response, and particularly as vaccines, against one or more angiotensin peptide moieties. Other carriers known in the art including BSA, keyhole limpet hemocyanin, tetanus toxoid, bacterial outer-membrane proteins, cholera toxin, and *Pseudomonas aeruginose* Exotoxin A may be inappropriate for use in an individual, and in particular a human. The aforementioned carriers may induce allergic reactions, or stimulate pathologic immune responses (for example, cholera toxin, KLH, BSA). The aforementioned carriers may require the presence of adjuvants such as complete Freund's adjuvant, now considered inappropriate for use in humans. A number of the carriers may be components of current vaccines (for example, tetanus toxoid, cholera toxin, Exotoxin A). As such, an individual may possess a high level of pre-existing immunity to these carriers, such that immunization with an antigen-carrier conjugate will induce a relatively greater immune response to the carrier than to the novel antigen. For these reasons, individually or as a whole, the conjugates and conjugates of the present invention represent a useful improvement over the above-described carrier proteins.

In the use of the embodiments of the invention, one or more angiotensin peptide moieties conjugated to core particles can be taken up by antigen presenting cells and thereby stimulate T-cell help to induce immune responses. T helper cell responses can be divided into type 1 ($T_H1$) and type 2 ($T_H2$) T helper cell responses (Romagnani, *Immunol. Today* 18:263–266 (1997)). $T_H1$ cells secrete interferon-gamma and other cytokines which trigger B cells to produce IgG1-3 antibodies. In contrast, a critical cytokine produced by $T_H2$ cells is IL-4, which drived B cells to produce IgG4 and IgE. In many experimental systems, the development of $T_H1$ and $T_H2$ responses is mutually exclusive since $T_H1$ cells suppress the induction of $T_H2$ cells and vice versa. Thus, antigens that trigger a strong $T_H1$ response simultaneously suppress the development of $T_H2$ responses and hence the production of IgE antibodies. Interestingly, virtually all viruses induce a $T_H1$ response in the host and fail to trigger the production of IgE antibodies (Coutelier et al., *J. Exp. Med.* 165:64-69 (1987)). Antibodies of the IgE isotype are important components in allergic reactions. Mast cells bind IgE antibodies on their surface and release histamines and other mediators of allergic response upon binding of specific antigen to the IgE molecules bound on the mast cell surface. The isotype pattern typical of $T_H1$ responses is not restricted to live viruses but has also been observed for inactivated or recombinant viral particles (Lo-Man et al., *Eur. J. Immunol.* 28:1401–1407 (1998)). Thus, by using the processes of the invention (e.g., AlphaVaccine Technology), viral particles can be decorated with various angiotensin peptide moieties and used for immunization. Due to the resulting "viral structure" of the array, a $T_H1$ response will be elicited, "protective" IgG1-3 antibodies will be produced, and the production of IgE antibodies which cause allergic reactions will be prevented. Thus, the invention embodies conjugates capable of inducing preferred immune responses, notably $T_H1$ type responses. Futher, the invention embodies the use of conjugates of the invention to counter allergic reactions induced by alternative vaccines against antigens of interest.

A further advantageous feature of the invention is that angiotensin peptide moieties may be presented on the particles in regular, repetitive arrays that are able to induce efficient immune responses both with and without T-cell help. This feature of the invention is particularly advantageous.

Unlike isolated proteins, viruses induce prompt and efficient immune responses in the absence of any adjuvants both with and without T-cell help (Bachmann & Zinkernagel, Ann. Rev. Immunol: 15:235–270 (1997)). Although viruses often consist of few proteins, they are able to trigger much stronger immune responses than their isolated components. For B-cell responses, it is known that one crucial factor for the immunogenicity of viruses is the repetitiveness and order of surface epitopes. Many viruses exhibit a quasi-crystalline surface that displays a regular array of epitopes which efficiently crosslinks epitope-specific immunoglobulins on B cells (Bachmann & Zinkernagel, Immunol. Today 17:553–558 (1996)). This crosslinking of surface immunoglobulins on B cells is a strong activation signal that directly induces cell-cycle progression and the production of IgM antibodies. Further, such triggered B cells are able to activate T helper cells, which in turn induce a switch from IgM to IgG antibody production in B cells and the generation of long-lived B cell memory—the goal of any vaccination (Bachmann & Zinkernagel, Ann. Rev. Immunol. 15:235–270 (1997)). The present invention provides one way to improve the efficiency of vaccination by increasing the degree of repetitiveness of the antiogensin peptide moiety to be used for immunization, through binding of the angiotensin peptide moiety to the core particles. As previously noted, the invention provides for conjugates comprising core particle modified to alter the number and or arrangement of the organizer.

As would be understood by one of ordinary skill in the art, when conjugates of the invention are administered to an individual, they may be in a conjugate which contains salts, buffers, adjuvants, or other substances which are desirable for improving the efficacy of the conjugate. Examples of materials suitable for use in preparing pharmaceutical conjugates are provided in numerous sources including, REMINGTON'S PHARMACEUTICAL SCIENCES (Osol, A, ed., Mack Publishing Co., (1990)).

Conjugates of the invention are said to be "pharmacologically accept-able" if their administration can be tolerated by a recipient individual. Further, the conjugates of the invention will be administered in a "therapeutically effective amount" (i.e., an amount that produces a desired physiological effect).

To induce an immune response, the conjugates of the present invention may be administered to an animal, suitably a mammal such as a human, by various methods known in the art, but will normally be administered by injection, infusion, inhalation, oral administration, or other suitable physical methods. The conjugates may alternatively be administered intramuscularly, intravenously, transmucosally, transdermally or subcutaneously. Components of conjugates for administration include sterile aqueous (e.g., physiological saline) or non-aqueous solutions and suspensions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption.

Further embodiments of the invention include immune molecules produced by immunization with conjugates of the invention. Immune molecules include antibodies and T-cell receptors. Such immune molecules may be useful in a vaccinated individual for binding to target one or more angiotensin peptide moieties. Immune molecules may also be useful when transferred to another individual not immunized against conjugates or conjugates of the invention, thereby to "passively" transfer immunity. In one embodiment, the immune molecule is an antibody. A monoclonal antibody suitable for binding one or more angiotensin peptide moieties may be transferred into an individual to achieve therapy or prophylaxis.

The invention also encompasses the use of antibodies produced by immunization with the conjugates or conjugates of the invention in kits for the detection of one or more angiotensin peptide moieties in immunoassays (eg ELISA). In a related embodiment, repetitive ordered arrays of angiotensin peptide moieties can be useful for the detection of antibodies against such moieties in binding assays. Other embodiments of the invention include processes for the production of the conjugates of the invention and methods of medical treatment using such conjugates, particularly to treat one or more physical disorders associated with the RAS such as hypertension, stroke, infarction, congestive heart failure, kidney failure or retinal hemorrhage.

It will be understood by one of ordinary skill in the relevant arts that other suitable modifications and adaptations to the methods and applications described herein are readily apparent and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Coupling of Peptides Derived from Angiotensin I and Angiotensin II to Qβ and the Immunization of Mice with the Resulting Conjugates A. Production of Conjugates The following angiotensin peptides moieties were chemically synthesized:

CGGDRVYIHPF (SEQ ID NO: 19, "Angio 1"), CGGDRVYIHPFHL (SEQ LID NO: 20, "Angio 2"), DRVYIHPFTILGGC (SEQ ID NO: 21, "Angio 3"), CDRVYIHPFHL (SEQ ID NO: 22, "Angio 4"), CHPFHL (SEQ ID NO: 23, "Angio 5"), CGPFHL (SEQ ID NO: 24, "Angio 6"), CYIHPF (SEQ ID NO: 25, "Angio 7"), CGIHPF (SEQ ID NO: 26, "Angio 8"), CGGHLPF (SEQ ID NO: 27, "Angio 9"), DRVYIGGC (SEQ ID NO: 28, "Angio 13"), DRVYGGC (SEQ ID NO: 29, "Angio 14") and DRVGGC (SEQ ID NO: 30, "Angio 15"). They were used for chemical coupling to Qβ as described in the following.

For peptides Angio 1 to Angio 4: A solution of 5 ml of 2 mg/ml Qβ capsid protein in 20 mM Hepes. 150 mM NaCl pH 7.4 was reacted for 30 minutes with 507 µl of a solution of 13 mg/ml Sulfo-MBS (Pierce) in H$_2$O at 25° C. on a rocking shaker. The reaction solution was subsequently dialyzed twice for 2 hours against 2 L of 20 mM Hepes, 150 mM NaCl, pH 7.4 at 4° C. 665 µl of the dialyzed reaction mixture was then reacted with 2.8 µl of each of the corresponding 100 mM peptide stock solution (in DMSO) for two hours at 25° C. on a rocking shaker. The reaction mixture was subsequently dialyzed 2×2 hours against 2 liters of 20 mM Hepes, 150 mM NaCl, pH 7.4 at 4° C.

For peptides Angio 5–9 and Angio 13–15: A solution of 3 ml of 2 mg/ml Qβ capsid protein in 20 mM Hepes. 150 mM NaCl pH 7.2 was reacted for 50 minutes with 86 µl of a solution of 100 mM SMPH (succinimidyl-6-(β-maleimidopropionoamido hexanoate, Pierce) in DMSO at 25° C. on a rocking shaker. The reaction solution was subsequently dialyzed twice for 2 hours against 2 L of 20 mM Hepes, 150 mM NaCl, pH 7.2 at 4° C. 514 µl of the dialyzed reaction mixture was then reacted with 3.6 µl of each of the corresponding 100 mM peptide stock solution (in DMSO) for 4 hours at 25° C. on a rocking shaker. The reaction mixture was subsequently dialyzed 2×2 hours against 2 liters of 20 mM Hepes, 150 mM NaCl, pH 7.2 at 4° C.

B. Immunization

Female Balb/c mice were vaccinated with one of the nine angiotensin peptide derivatives coupled to Qβ capsid protein without the addition of adjuvants. 50 g (Qβ-Angio 1–4 vaccine) or 20 µg (Qβ-Angio 5–9 vaccine) of total protein of each sample was diluted in PBS to 200 µl and injected subcutaneously (100 µl on two ventral sides) on day 0 and day 14. Mice were bled retroorbitally on day 21 and their serum was analyzed using an antgiotensin-specific ELISA It should be noted that the human and the murine sequences of the angiotensin peptides identically correspond to each other. Therefore, immunization of a human or a mouse with vaccines or conjugates, respectively, comprising angiotensin peptide moieties as antigenic determinant in accordance with the invention, is a vaccination against a self-antigen.

Example 2

ELISA Analysis of Sera from Mice Vaccinated with Peptides Derived from Angiotensin I and Angiotensin II Coupled to Qβ

Angio 1 to Angio 9 and Angio13–15 peptide derivatives prepared as described in Example 1 were individually coupled to bovine RNAse A (Sigma) using the chemical cross-linker sulfo-SPDP. ELISA plates were coated overnight at 4° C. with coupled RNAse preparations at a concentration of 10 µg/ml in coating buffer (0.1M NaH$_2$CO$_3$, pH 9.6). Alternatively, angiotensin I or angiotensin II (SIGMA) were diluted in the same coating buffer to a concentration of 200 µg/ml. The plates were blocked with blocking buffer (2% bovine serum albumin (BSA) in PBS (pH 7.4)/0.05% Tween 20) for 2 hours at 37° C., washed with PBS (pH 7.4)/0.05% Tween 20 and then incubated for 2 hours at room temperature with serially diluted mouse sera in blocking buffer. The plates were washed with PBS (pH 7.4)/0.05% Tween 20. and then incubated with horse radish peroxidase-labeled goat anti-mouse IgG antibody at 1 µg/ml (Jackson ImmunoResearch) for 1 hour at room temperature. The plates were washed with PBS (pH 7.4)/0.05% Tween 20 and the substrate solution was added (0.066M $Na_2HPO_4$, 0.035 M citric acid (pH 5.0)+0.4 mg OPD (1,2-Phenylenediamine dihydrochloride)+0.01% $H_2O_2$). After 10 min the color reaction was stopped with 5% $H_2SO_4$ and absorbance was read at 450 nm.

As a control, preimmune sera of the same mice were also tested. Control ELISA experiments using sera from mice immunized with unrelated peptides crosslinked to Qβ or other carriers showed that the antibodies detected were specific for the respective peptide. ELISA titers were calculated as the reciprocal serum dilution which gives a half-maximal signal in the ELISA (50% of maximal optical density).

Results:

FIG. 1 shows ELISA analyses of IgG antibodies specific for the Angio 2 peptide and angiotensin I in sera of mice immunized with Angio 1–4 peptides coupled to Qβ capsid protein. Qβ-Angio 1, Qβ-Angio 1, Qβ-Angio 3 and Qβ-Angio 4, as used in the figures, stand for the vaccine injected in the mice, from which the sera are derived in accordance with above definition of the angiotensin peptides. Female Balb/c mice were vaccinated subcutaneously with 50 µg of vaccine in PBS on day 0 and day 14. IgG antibodies in sera of mice vaccinated with Qβ-Angio 1, Qβ-Angio 2, Qβ-Angio 3 and Qβ-Angio 4 were measured on day 21 against Angio 2 peptide coupled to RNAse A and against angiotensin I. As a control, a pre-immune sera were also analyzed. Results for indicated serum dilutions are shown as optical density at 450 nm. The average of three mice each (including standard deviations) is shown for Angio 2. The average of two mice each are shown for angiotensin I. All vaccinated mice made specific IgG antibodies against the Angio 2 peptide as well as angiotensin I although the mice immunized with the Angio 2, Angio 3 or Angio 4 peptide exhibited higher titers than those vaccinated with the Angio 1 peptide correlating with the close similarity of the Angio 2, Angio 3 and Angio 4 peptides and angiotensin I.

FIG. 2 shows ELISA analyses of IgG antibodies specific for the Angio I peptide and angiotensin II in sera of mice immunized with Angio 1–4 peptides coupled to Qβ capsid protein. Qβ-Angio 1, Qβ-Angio 1, Qβ-Angio 3 and Qβ-Angio 4, as used in the figures, stand for the vaccine injected in the mice, from which the sera are derived in accordance with above definition of the angiotensin peptides. Female Balb/c mice were vaccinated subcutaneously with 50 µg of vaccine in PBS on day 0 and day 14. IgG antibodies in sera of mice vaccinated with Qβ-Angio 1, Qβ-Angio 2, Qβ-Angio 3 and Qβ-Angio 4 were measured on day 21 against Angio 1 peptide coupled to RNAse A and against angiotensin II. As a control, a pre-immune sera were also analyzed. Results for indicated serum dilutions are shown as optical density at 450 nm. The average of three mice each (including standard deviations) is shown for Angio 1. The average of two mice each are shown for angiotensin II. All vaccinated mice made specific IgG antibodies against the Angio 1 peptide as well as angiotensin II although the mice immunized with the Angio 1 peptide exhibited the highest titers correlating with the close similarity of the Angio 1 peptide and angiotensin II.

FIG. 3 shows ELISA analyses of IgG antibodies specific for the Angio 2 peptide and angiotensin I in sera of mice immunized with Angio 5–9 peptides coupled to Qβ capsid protein. Qβ-Angio 5, Qβ-Angio 6, Qβ-Angio 7, Qβ-Angio 8 and Qβ-Angio 9, as used in the figures, stand for the vaccine injected in the mice, from which the sera are derived in accordance with above definition of the angiotensin peptides. Female Balb/c mice were vaccinated subcutaneously with 20 µg of vaccine in PBS on day 0 and day 14. IgG antibodies in sera of mice vaccinated with Qβ-Angio 4, Qβ-Angio 5, Qβ-Angio 6, Qβ-Angio 7, Qβ-Angio 8 and Qβ-Angio 9 were measured on day 21 against Angio 2 peptide coupled to RNAse A and against angiotensin I. Results for indicated serum dilutions are shown as optical density at 450 nm. The average of two mice each are shown. The two mice vaccinated with Qβ-Angio 8 and Qβ-Angio 9 exhibited very low or no specific titers against the Angio 2 peptide as well as angiotensin I, indicating that these two types of vaccine induced antibodies which were mostly specific for the C-terminus of angiotensin II but not for angiotensin I (see also FIG. 4).

FIG. 4 shows ELISA analyses of IgG antibodies specific for the Angio 1 peptide and angiotensin II in sera of mice immunized with Angio 5–9 peptides coupled to Qβ capsid protein. Qβ-Angio 5, Qβ-Angio 6, Qβ-Angio 7, Qβ-Angio 8 and Qβ-Angio 9, as used in the figures, stand for the vaccine injected in the mice, from which the sera are derived in accordance with above definition of the angiotensin peptides. Female Balb/c mice were vaccinated subcutaneously with 20 µg of vaccine in PBS on day 0 and day 14. IgG antibodies in sera of mice vaccinated with Qβ-Angio 4, Qβ-Angio 5, Qβ-Angio 6, Qβ-Angio 7, Qβ-Angio 8 and Qβ-Angio 9 were measured on day 21 against Angio 1 peptide coupled to RNAse A and against angiotensin II. Results for indicated serum dilutions are shown as optical density at 450 nm. The average of two mice each are shown. The two mice vaccinated with Qβ-Angio 5 and Qβ-Angio 6 exhibited very low or no specific titers against the Angio I peptide as well as angiotensin II, indicating that these two types of vaccine induced antibodies which were mostly specific for the C-terminus of angiotensin I but not for angiotensin II (see also FIG. 3).

The following table summarizes the ELISA analysis of sera from mice vaccinated with the Angio peptides 1 to 9 coupled to Qβ. Average ELISA titers from day 21 were calculated as described in Example 2.

TABLE 1

Angiotensin-derived peptides used for vaccination of mice and resulting antibody responses against the used peptides as well as angiotensin I and angiotensin II.

| SEQ ID NO: Name of peptide | Amino acid sequence | Avg. ELISA titer against Angiotensin I | Avg. ELISA titer against Angio 2 peptide | Avg. ELISA titer against Angiotensin II | Avg. ELISA titer against Angio 1 peptide |
|---|---|---|---|---|---|
| SEQ ID NO: 19 Angio 1 | CGGDRVYIHPF | <50 | 5321 | | 711 |

TABLE 1-continued

Angiotensin-derived peptides used for vaccination of mice and resulting antibody responses against the used peptides as well as angiotensin I and angiotensin II.

| SEQ ID NO: Name of peptide | Amino acid sequence | Avg. ELISA titer against Angiotensin I | Avg. ELISA titer against Angio 2 peptide | Avg. ELISA titer against Angiotensin II | Avg. ELISA titer against Angio 1 peptide |
|---|---|---|---|---|---|
| SEQ ID NO: 20 Angio 2 | CGGDRVYIHPFHL | 1250 | 16416 | 68 | 1064 |
| SEQ ID NO: 21 Angio 3 | DRVYIHPFHLGGC | 1250 | 20898 | 74 | 476 |
| SEQ ID NO: 22 Angio 4 | CDRVYIHPFHL | 559 | 11898 | 142 | 906 |
| SEQ ID NO: 23 Angio 5 | CHPFHL | 3856 | 1877 | 50 | <50 |
| SEQ ID NO: 24 Angio 6 | CGPFHL | 1250 | 870 | <50 | <50 |
| SEQ ID NO: 25 Angio 7 | CYIHPF | 112 | 626 | 6250 | 971 |
| SEQ ID NO: 26 Angio 8 | CGIHPF | <50 | 87 | 476 | 1350 |
| SEQ ID NO: 27 Angio 9 | CGGHPF | <50 | 50 | 476 | 2338 |
| SEQ ID NO: 28 Angio 13 | DRVYIGGC | n.t.* | n.t. | n.t. | n.t. |
| SEQ ID NO: 29 Angio 14 | DRVYGGC | n.t. | n.t. | n.t. | n.t. |
| SEQ ID NO: 29 Angio 15 | DRVGGC | n.t. | n.t. | n.t. | n.t. |

*n.t. = not tested

The results with Angio 5 and Angio 6 show that peptides can be induced that selectively recognize Angiotensin I. Furthermore, the results with Angio 7–9 show that antibodies can be induced that selectively recognize Angiotensin II but not Angiotensin I. Since Angiotensin I and II differ by 2 amino acids only at the C-terminus while the remaining 8 amino acids are identical, these results demonstrate that all antibodies induced by Angio 5 or Angio 6 selectively recognize the C-terminus of Angiotensin I and that antibodies induced by Angio 7–9, and in particular Angio 8–9, selectively recognize the C-terminus of Angiotensin II. Thus, the shared 8 amino acids are not recognized and in particular the shared N-terminus is not recognized. This indicates that the N-terminus is not buried inside antibodies when bound and, therefore, is accessible for proteases.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. An angiotensin peptide moiety-carrier conjugate comprising:
   (a) a carrier with at least one first attachment site, and
   (b) at least one angiotensin peptide moiety with at least one second attachment site;
   wherein said carrier comprises a core particle that is a virus-like particle of an RNA bacteriophage and;
   wherein said second attachment site associates with said first attachment site through at least one non-peptide bond so as to form an ordered and repetitive angiotensin peptide moiety-carrier conjugate.

2. The conjugate of claim 1, wherein said virus-like particle of an RNA bacteriophage comprises proteins, or fragments thereof, of an RNA bacteriophage.

3. The conjugate of claim 2, wherein said RNA bacteriophage is selected from the group consisting of:
   (a) bacteriophage Qβ;
   (b) bacteriophage R17;
   (c) bacteriophage fr;
   (d) bacteriophage GA;
   (e) bacteriophage SP;
   (f) bacteriophage MS2;
   (g) bacteriophage M11;
   (h) bacteriophage MX1;
   (i) bacteriophage NL95;
   (j) bacteriophage f2;
   (k) bacteriophage AP205; and
   (l) bacteriophage PP7.

4. The conjugate of claim 1, wherein said virus-like particle of an RNA bacteriophage comprises recombinant proteins, or fragments thereof, of bacteriophage Qβ.

5. The conjugate of claim 1, wherein said virus-like particle of an RNA bacteriophage comprises recombinant proteins or fragments thereof, of bacteriophage AP205.

6. The conjugate of claim 2, wherein said virus-like particle of an RNA bacteriophage comprises one or more coat proteins of said RNA bacteriophage which have been modified by deletion or substitution to remove at least one naturally occurring lysine residue, or that have been modified by insertion or substitution to add at least one lysine residue.

7. The conjugate of claim 4, wherein said recombinant proteins comprise one or more coat proteins having an amino acid sequence of SEQ ID NO:3.

8. The conjugate of claim 4, wherein said recombinant proteins comprise a mixture of coat proteins having amino acid sequences of SEQ ID NO: 4 or mutants thereof, and SEQ ID NO:3.

9. The conjugate of claim 6 wherein said RNA bacteriophage is Qβ.

10. The conjugate of claim 9, wherein said virus-like particle comprises one or more proteins having an amino acid sequence selected from the group consisting of:
(a) the amino acid sequence of SEQ ID NO:6;
(b) the amino acid sequence of SEQ ID NO:7;
(c) the amino acid sequence of SEQ ID NO:8;
(d) the amino acid sequence of SEQ ID NO:9; and
(e) the amino acid sequence of SEQ ID NO:10.

11. The conjugate of claim 1, wherein said first attachment site comprises:
(a) an amino group;
(b) a carboxyl group;
(c) a sulfhydryl group;
(d) a hydroxy group;
(e) a guanidinyl group; or
(f) a histidinyl group.

12. The conjugate of claim 1, wherein said at least one first attachment site is selected from the group consisting of a lysine residue, an arginine residue, a cysteine residue, an asparatate residue, a glutamate residue, a serine residue, a threonine residue, a histidine residue and a tyrosine residue.

13. The conjugate of claim 1, wherein said at least one first attachment site is a lysine residue.

14. The conjugate of claim 1, wherein said angiotensin peptide moiety is an angiotensin peptide selected from the group consisting of angiotensinogen, angiotensin I, angiotensin II, and fragments or derivatives thereof.

15. The conjugate of claim 1, wherein said angiotensin peptide moiety with said second attachment site has an amino acid sequence selected from the group consisting of:

| | | |
|---|---|---|
| (a) | CGGDRVYIHPF; | (SEQ ID NO: 19) |
| (b) | CGGDRVYHPFHL; | (SEQ ID NO: 20) |
| (c) | DRVYIHPFHLGGC; | (SEQ ID NO: 21) |
| (d) | CDRVYIHPFHL; | (SEQ ID NO: 22) |
| (e) | CHPFHL; | (SEQ ID NO: 23) |
| (f) | CGPFHL; | (SEQ ID NO: 24) |
| (g) | CYIHPF; | (SEQ ID NO: 25) |
| (h) | CGIHPF; | (SEQ ID NO: 26) |
| (i) | CGGHPF; | (SEQ ID NO: 27) |
| (j) | DRVYIGGC; | (SEQ ID NO: 28) |
| (k) | DRVYGGC; | (SEQ ID NO: 29) |
| (l) | DRVGGC; | (SEQ ID NO: 30) |
| (m) | DRVY; | (SEQ ID NO: 34) |
| (n) | DRVYIHPF; and | (SEQ ID NO: 17) |
| (o) | DRVYIHPFHL. | (SEQ ID NO: 16) |

16. A pharmaceutical composition comprising one or more of the conjugates of claim 1 and a pharmaceutically acceptable carrier or excipient.

17. A vaccine composition comprising the conjugate of claim 1 and an immunologically acceptable carrier or excipient.

18. The vaccine composition of claim 17, wherein said vaccine composition further comprises at least one adjuvant.

19. A method of immunizing an animal against an angiotensin peptide moiety, comprising administering the conjugate of claim 1 to an animal under conditions such that said animal develops an immune response to said angiotensin peptide moiety.

20. The method of claim 19, wherein said conjugate is administered to said animal via a route of administration selected from the group consisting of intranasal administration, oral administration, subcutaneous administration, transdermal administration, intramuscular administration and intravenous administration.

21. The method of claim 20, wherein said conjugate is administered to said animal intranasally.

22. A method of immunizing an animal against an angiotensin peptide moiety, comprising administering the vaccine composition of claim 17 or claim 18 to an animal under conditions such that said animal develops an immune response to said angiotensin peptide moiety.

23. The method of claim 22, wherein said composition is administered to said animal via a route of administration selected from the group consisting of intranasal administration, oral administration, subcutaneous administration, transdermal administration, intramuscular administration and intravenous administration.

24. The method of claim 22, wherein said composition is administered to said animal intranasally.

25. A method of treating or preventing a physical disorder associated with the renin-activated angiotensin system comprising administering to an animal a therapeutically or prophylactically effective amount of one or more of the conjugates of claim 1.

26. The method of claim 25, wherein said physical disorder associated with the renin-activated angiotensin system is selected from the group consisting of hypertension, stroke, infarction, congestive heart failure, kidney failure and retinal hemorrhage.

27. A method of treating or preventing a physical disorder associated with the renin-activated angiotensin system comprising administering to an animal a therapeutically or prophylactically effective amount of the pharmaceutical composition of claim 16.

28. A method of treating or preventing a physical disorder associated with the renin-activated angiotensin system comprising administering to an animal an immunologically effective amount of the vaccine composition of claim 17 or claim 18.

29. The method of claim 27 wherein said physical disorder associated with the renin-activated angiotensin system is selected from the group consisting of hypertension, stroke, infarction, congestive heart failure, kidney failure and retinal hemorrhage.

30. The conjugate of claim 1, wherein said second attachment site associates with said first attachment site through at least one non-peptide covalent bond so as to form an ordered and repetitive angiotensin peptide moiety-carrier array.

31. The conjugate of claim 1, wherein said first attachment comprises an amino group.

32. The conjugate of claim 1, wherein said second attachment site comprises a sulfhydryl group.

33. The conjugate of claim 1, wherein said first attachment site comprises an amino group and wherein said second attachment comprises a sulfhydryl group.

34. The conjugate of claim 1, wherein said first attachment site is not a sulfhydryl group.

35. The conjugate of claim 1, wherein said virus-like particle of an RNA bacteriophage comprises recombinant proteins, or fragments thereof, of bacteriophage fr.

36. The conjugate of claim 1, wherein only one of said second attachment sites associates with said first attachment site through at least one non-peptide covalent bond leading to a single and uniform type of binding of said angiotensin peptide moiety to said core particle, wherein said only one second attachment site that associates with said first attachment site is a sulfhydryl group, and wherein said angiotensin peptide moiety and said core particle interact through said association to form an ordered and repetitive antigen array.

37. The conjugate of claim 1, wherein said angiotensin peptide moiety is angiotensin II.

38. The conjugate of claim 1, wherein said angiotensin peptide moiety with said second attachment site consists of the amino acid sequence of CGGDRVYIHPF (SEQ ID NO: 19).

39. The vaccine composition of claim 18, wherein said adjuvant is aluminium hydroxide.

40. The method of claim 28 wherein said physical disorder associated with the renin-activated angiotensin system is selected from the group consisting of hypertension, stroke, infarction, congestive heart failure, kidney failure and retinal hemorrhage.

* * * * *

UNITED STATES PATENT AND TRADEMARK OFFICE
CERTIFICATE OF CORRECTION

PATENT NO.       : 7,115,266 B2
APPLICATION NO.  : 10/264267
DATED            : October 3, 2006
INVENTOR(S)      : Martin Bachmann It is certified that error appears in the above-identified patent and that said Letters Patent is hereby corrected as shown below:

On the title page item (63), in the Related U.S. Application Data, please delete: "Continuation-in-part of application No. PCT/IB02/00166, filed on Jan. 21, 2002, and a continuation-in-part of application No. 10/050,902, filed on Jan. 18, 2001." and insert therein -- Continuation-in-part of application No. PCT/IB02/00166, filed on Jan. 21, 2002, and a continuation-in-part of application No. 10/050,902, filed on Jan. 18, 2002. --.

In column 26, line 15, please delete "SEQ ID NO:31" and insert therein --SEQ ID NO:32 --.

In column 29, line 18, please delete "the tip promoter" and insert therein -- the trp promoter --.

In column 37, lines 2-3, please delete "the PrP protein, PrP peptide or the PrP domain" and insert therein -- the angiotensin peptide moiety --.

In column 38, line 53-54, please delete "SEQ ID NO:10 and SEQ ID NO:11" and insert therein -- SEQ ID NO:3 and SEQ ID NO:4 --.

In column 38, line 56, please delete "SEQ ID NO:32" and insert therein -- SEQ ID NO:33 --.

In column 49, line 19, please delete "FIG. 1" and insert therein -- FIG. 2 --.

In column 49, line 41, please delete "FIG. 2" and insert therein -- FIG. 1 --.

In column 50, line 9 please delete "FIG. 3" and insert therein -- FIG. 4 --.

In column 50, line 29, please delete "FIG. 4" and insert therein -- FIG. 3 --.

In column 50, line 30, please delete "FIG. 4" and insert therein -- FIG. 3 --.

In column 50, line 45, please delete "Angio I" and insert therein -- Angio 1 --.

UNITED STATES PATENT AND TRADEMARK OFFICE
CERTIFICATE OF CORRECTION

PATENT NO. : 7,115,266 B2
APPLICATION NO. : 10/264267
DATED : October 3, 2006
INVENTOR(S) : Martin Bachmann It is certified that error appears in the above-identified patent and that said Letters Patent is hereby corrected as shown below:

In column 50, line 49, please delete "FIG. 3" and insert therein -- FIG. 4 --.

Signed and Sealed this

Thirteenth Day of November, 2007

JON W. DUDAS
*Director of the United States Patent and Trademark Office*

SEQUENCE LISTING

<160> NUMBER OF SEQ ID NOS: 34

<210> SEQ ID NO 1
<211> LENGTH: 185
<212> TYPE: PRT
<213> ORGANISM: Artificial Sequence

```
<220> FEATURE:
<223> OTHER INFORMATION: HBcAg polypeptide

<400> SEQUENCE: 1

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Ser Gln Ser Pro Arg Arg Arg
                165                 170                 175

Arg Ser Gln Ser Arg Glu Ser Gln Cys
            180                 185

<210> SEQ ID NO 2
<211> LENGTH: 182
<212> TYPE: PRT
<213> ORGANISM: Escherichia coli

<400> SEQUENCE: 2

Met Lys Ile Lys Thr Leu Ala Ile Val Val Leu Ser Ala Leu Ser Leu
1               5                   10                  15

Ser Ser Thr Thr Ala Leu Ala Ala Thr Thr Val Asn Gly Gly Thr
            20                  25                  30

Val His Phe Lys Gly Glu Val Val Asn Ala Ala Cys Ala Val Asp Ala
        35                  40                  45

Gly Ser Val Asp Gln Thr Val Gln Leu Gly Gln Val Arg Thr Ala Ser
    50                  55                  60

Leu Ala Gln Glu Gly Ala Thr Ser Ser Ala Val Gly Phe Asn Ile Gln
65                  70                  75                  80

Leu Asn Asp Cys Asp Thr Asn Val Ala Ser Lys Ala Ala Val Ala Phe
                85                  90                  95

Leu Gly Thr Ala Ile Asp Ala Gly His Thr Asn Val Leu Ala Leu Gln
            100                 105                 110

Ser Ser Ala Ala Gly Ser Ala Thr Asn Val Gly Val Gln Ile Leu Asp
        115                 120                 125

Arg Thr Gly Ala Ala Leu Thr Leu Asp Gly Ala Thr Phe Ser Ser Glu
    130                 135                 140

Thr Thr Leu Asn Asn Gly Thr Asn Thr Ile Pro Phe Gln Ala Arg Tyr
145                 150                 155                 160
```

```
Phe Ala Thr Gly Ala Ala Thr Pro Gly Ala Ala Asn Ala Asp Ala Thr
                165                 170                 175
Phe Lys Val Gln Tyr Gln
            180

<210> SEQ ID NO 3
<211> LENGTH: 132
<212> TYPE: PRT
<213> ORGANISM: Bacteriophage Q beta CP

<400> SEQUENCE: 3

Ala Lys Leu Glu Thr Val Thr Leu Gly Asn Ile Gly Lys Asp Gly Lys
1               5                   10                  15
Gln Thr Leu Val Leu Asn Pro Arg Gly Val Asn Pro Thr Asn Gly Val
            20                  25                  30
Ala Ser Leu Ser Gln Ala Gly Ala Val Pro Ala Leu Glu Lys Arg Val
        35                  40                  45
Thr Val Ser Val Ser Gln Pro Ser Arg Asn Arg Lys Asn Tyr Lys Val
    50                  55                  60
Gln Val Lys Ile Gln Asn Pro Thr Ala Cys Thr Ala Asn Gly Ser Cys
65                  70                  75                  80
Asp Pro Ser Val Thr Arg Gln Ala Tyr Ala Asp Val Thr Phe Ser Phe
                85                  90                  95
Thr Gln Tyr Ser Thr Asp Glu Glu Arg Ala Phe Val Arg Thr Glu Leu
            100                 105                 110
Ala Ala Leu Leu Ala Ser Pro Leu Leu Ile Asp Ala Ile Asp Gln Leu
        115                 120                 125
Asn Pro Ala Tyr
    130

<210> SEQ ID NO 4
<211> LENGTH: 329
<212> TYPE: PRT
<213> ORGANISM: Bacteriophage Q beta A1 protein

<400> SEQUENCE: 4

Met Ala Lys Leu Glu Thr Val Thr Leu Gly Asn Ile Gly Lys Asp Gly
1               5                   10                  15
Lys Gln Thr Leu Val Leu Asn Pro Arg Gly Val Asn Pro Thr Asn Gly
            20                  25                  30
Val Ala Ser Leu Ser Gln Ala Gly Ala Val Pro Ala Leu Glu Lys Arg
        35                  40                  45
Val Thr Val Ser Val Ser Gln Pro Ser Arg Asn Arg Lys Asn Tyr Lys
    50                  55                  60
Val Gln Val Lys Ile Gln Asn Pro Thr Ala Cys Thr Ala Asn Gly Ser
65                  70                  75                  80
Cys Asp Pro Ser Val Thr Arg Gln Ala Tyr Ala Asp Val Thr Phe Ser
                85                  90                  95
Phe Thr Gln Tyr Ser Thr Asp Glu Glu Arg Ala Phe Val Arg Thr Glu
            100                 105                 110
Leu Ala Ala Leu Leu Ala Ser Pro Leu Leu Ile Asp Ala Ile Asp Gln
        115                 120                 125
Leu Asn Pro Ala Tyr Trp Thr Leu Leu Ile Ala Gly Gly Gly Ser Gly
    130                 135                 140
Ser Lys Pro Asp Pro Val Ile Pro Asp Pro Pro Ile Asp Pro Pro Pro
145                 150                 155                 160
```

```
Gly Thr Gly Lys Tyr Thr Cys Pro Phe Ala Ile Trp Ser Leu Glu Glu
                165                 170                 175

Val Tyr Glu Pro Pro Thr Lys Asn Arg Pro Trp Pro Ile Tyr Asn Ala
            180                 185                 190

Val Glu Leu Gln Pro Arg Glu Phe Asp Val Ala Leu Lys Asp Leu Leu
        195                 200                 205

Gly Asn Thr Lys Trp Arg Asp Trp Asp Ser Arg Leu Ser Tyr Thr Thr
    210                 215                 220

Phe Arg Gly Cys Arg Gly Asn Gly Tyr Ile Asp Leu Asp Ala Thr Tyr
225                 230                 235                 240

Leu Ala Thr Asp Gln Ala Met Arg Asp Gln Lys Tyr Asp Ile Arg Glu
                245                 250                 255

Gly Lys Lys Pro Gly Ala Phe Gly Asn Ile Glu Arg Phe Ile Tyr Leu
            260                 265                 270

Lys Ser Ile Asn Ala Tyr Cys Ser Leu Ser Asp Ile Ala Ala Tyr His
        275                 280                 285

Ala Asp Gly Val Ile Val Gly Phe Trp Arg Asp Pro Ser Ser Gly Gly
    290                 295                 300

Ala Ile Pro Phe Asp Phe Thr Lys Phe Asp Lys Thr Lys Cys Pro Ile
305                 310                 315                 320

Gln Ala Val Ile Val Val Pro Arg Ala
                325

<210> SEQ ID NO 5
<211> LENGTH: 49
<212> TYPE: PRT
<213> ORGANISM: Artificial Sequence
<220> FEATURE:
<223> OTHER INFORMATION: GCN4 polypeptide

<400> SEQUENCE: 5

Pro Ala Ala Leu Lys Arg Ala Arg Asn Glu Ala Ala Arg Arg Ser Arg
1               5                   10                  15

Ala Arg Lys Leu Gln Arg Met Lys Gln Leu Glu Asp Lys Val Glu Glu
            20                  25                  30

Leu Leu Ser Lys Asn Tyr His Leu Glu Asn Glu Val Ala Arg Leu Lys
        35                  40                  45

Lys

<210> SEQ ID NO 6
<211> LENGTH: 132
<212> TYPE: PRT
<213> ORGANISM: Bacteriophage Q beta 240

<400> SEQUENCE: 6

Ala Lys Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95
```

-continued

```
Thr Gln Tyr Ser Thr Asp Glu Glu Arg Ala Phe Val Arg Thr Glu Leu
            100                 105                 110

Ala Ala Leu Leu Ala Ser Pro Leu Ile Asp Ala Ile Asp Gln Leu
        115                 120                 125

Asn Pro Ala Tyr
        130

<210> SEQ ID NO 7
<211> LENGTH: 130
<212> TYPE: PRT
<213> ORGANISM: Bacteriophage Q beta 243

<400> SEQUENCE: 7

Ala Lys Leu Glu Thr Val Thr Leu Gly Lys Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Asp Leu Leu Ile Asp Ala Ile Asp Gln Leu Asn Pro
        115                 120                 125

Ala Tyr
    130

<210> SEQ ID NO 8
<211> LENGTH: 130
<212> TYPE: PRT
<213> ORGANISM: Bacteriophage Q beta 250

<400> SEQUENCE: 8

Ala Arg Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Asp Leu Leu Ile Asp Ala Ile Asp Gln Leu Asn Pro
        115                 120                 125

Ala Tyr
    130
```

-continued

```
<210> SEQ ID NO 9
<211> LENGTH: 130
<212> TYPE: PRT
<213> ORGANISM: Bacteriophage Q beta 259

<400> SEQUENCE: 9

Ala Arg Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Asp Leu Leu Ile Asp Ala Ile Asp Gln Leu Asn Pro
        115                 120                 125

Ala Tyr
    130

<210> SEQ ID NO 10
<211> LENGTH: 130
<212> TYPE: PRT
<213> ORGANISM: Artificial Sequence
<220> FEATURE:
<223> OTHER INFORMATION: Q beta 251

<400> SEQUENCE: 10

Ala Lys Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Asp Leu Leu Ile Asp Ala Ile Asp Gln Leu Asn Pro
        115                 120                 125

Ala Tyr
    130

<210> SEQ ID NO 11
<211> LENGTH: 3635
<212> TYPE: DNA
<213> ORGANISM: Plasmid pAP283 58
```

<400> SEQUENCE: 11

```
cgagctcgcc cctggcttat cgaaattaat acgactcact atagggagac cggaattcga    60
gctcgcccgg ggatcctcta gaattttctg cgcacccatc ccgggtggcg cccaaagtga   120
ggaaaatcac atggcaaata agccaatgca accgatcaca tctacagcaa ataaaattgt   180
gtggtcggat ccaactcgtt tatcaactac attttcagca agtctgttac gccaacgtgt   240
taaagttggt atagccgaac tgaataatgt ttcaggtcaa tatgtatctg tttataagcg   300
tcctgcacct aaaccggaag gttgtgcaga tgcctgtgtc attatgccga atgaaaacca   360
atccattcgc acagtgattt cagggtcagc cgaaaacttg gctaccttaa aagcagaatg   420
ggaaactcac aaacgtaacg ttgacacact cttcgcgagc ggcaacgccg gtttgggttt   480
ccttgaccct actgcggcta tcgtatcgtc tgatactact gcttaagctt gtattctata   540
gtgtcaccta aatcgtatgt gtatgataca taaggttatg tattaattgt agccgcgttc   600
taacgacaat atgtacaagc ctaattgtgt agcatctggc ttactgaagc agaccctatc   660
atctctctcg taaactgccg tcagagtcgg tttggttgga cgaaccttct gagtttctgg   720
taacgccgtt ccgcaccccg gaaatggtca ccgaaccaat cagcagggtc atcgctagcc   780
agatcctcta cgccggacgc atcgtggccg gcatcaccgg cgccacaggt gcggttgctg   840
gcgcctatat cgccgacatc accgatgggg aagatcgggc tcgccacttc gggctcatga   900
gcgcttgttt cggcgtgggt atggtggcag gccccgtggc cgggggactg ttgggcgcca   960
tctccttgca tgcaccattc cttgcggcgg cggtgctcaa cggcctcaac ctactactgg  1020
gctgcttcct aatgcaggag tcgcataagg gagagcgtcg atatggtgca ctctcagtac  1080
aatctgctct gatgccgcat agttaagcca actccgctat cgctacgtga ctgggtcatg  1140
gctgcgcccc gacacccgcc aacacccgct gacgcgccct gacgggcttg tctgctcccg  1200
gcatccgctt acagacaagc tgtgaccgtc tccgggagct gcatgtgtca gaggttttca  1260
ccgtcatcac cgaaacgcgc gaggcagctt gaagacgaaa gggcctcgtg atacgcctat  1320
ttttataggt taatgtcatg ataataatgg tttcttagac gtcaggtggc acttttcggg  1380
gaaatgtgcg cggaaccct atttgtttat ttttctaaat acattcaaat atgtatccgc   1440
tcatgagaca ataaccctga taatgcttc aataatattg aaaaggaag agtatgagta   1500
ttcaacattt ccgtgtcgcc cttattccct tttttgcggc attttgcctt cctgtttttg   1560
ctcacccaga aacgctggtg aaagtaaaag atgctgaaga tcagttgggt gcacgagtgg   1620
gttacatcga actggatctc aacagcggta agatccttga gagttttcgc cccgaagaac   1680
gttttccaat gatgagcact tttaaagttc tgctatgtgg cgcggtatta tcccgtattg   1740
acgccgggca agagcaactc ggtcgccgca tacactattc tcagaatgac ttggttgagt   1800
actcaccagt cacagaaaag catcttacgg atggcatgac agtaagagaa ttatgcagtg   1860
ctgccataac catgagtgat aacactgcgg ccaacttact tctgacaacg atcggaggac   1920
cgaaggagct aaccgctttt ttgcacaaca tgggggatca tgtaactcgc cttgatcgtt   1980
gggaaccgga gctgaatgaa gccataccaa acgacgagcg tgacaccacg atgcctgtag   2040
caatggcaac aacgttgcgc aaactattaa ctggcgaact acttactcta gcttcccggc   2100
aacaattaat agactggatg gaggcggata agttgcagg accacttctg cgctcggccc   2160
ttccggctgg ctggtttatt gctgataaat ctggagccgg tgagcgtggg tctcgcggta   2220
tcattgcagc actggggcca gatggtaagc cctcccgtat cgtagttatc tacacgacgg   2280
ggagtcaggc aactatggat gaacgaaata gacagatcgc tgagataggt gcctcactga   2340
```

-continued

```
ttaagcattg gtaactgtca gaccaagttt actcatatat actttagatt gatttaaaac    2400
ttcattttta atttaaaagg atctaggtga agatcctttt tgataatctc atgaccaaaa    2460
tcccttaacg tgagttttcg ttccactgag cgtcagaccc cgtagaaaag atcaaaggat    2520
cttcttgaga tcctttttt ctgcgcgtaa tctgctgctt gcaaacaaaa aaaccaccgc    2580
taccagcggt ggtttgtttg ccggatcaag agctaccaac tctttttccg aaggtaactg    2640
gcttcagcag agcgcagata ccaaatactg tccttctagt gtagccgtag ttaggccacc    2700
acttcaagaa ctctgtagca ccgcctacat acctcgctct gctaatcctg ttaccagtgg    2760
ctgctgccag tggcgataag tcgtgtctta ccgggttgga ctcaagacga tagttaccgg    2820
ataaggcgca gcggtcgggc tgaacggggg gttcgtgcac acagcccagc ttggagcgaa    2880
cgacctacac cgaactgaga tacctacagc gcgagcattg agaaagcgcc acgcttcccg    2940
aagggagaaa ggcggacagg tatccggtaa gcggcagggt cggaacagga gagcgcacga    3000
gggagcttcc agggggaaac gcctggtatc tttatagtcc tgtcgggttt cgccacctct    3060
gacttgagcg tcgatttttg tgatgctcgt caggggggcg gagcctatgg aaaaacgcca    3120
gcaacgcggc cttttacgg ttcctggcct tttgctggcc ttttgctcac atgttctttc    3180
ctgcgttatc ccctgattct gtggataacc gtattaccgc ctttgagtga gctgataccg    3240
ctcgccgcag ccgaacgacc gagcgcagcg agtcagtgag cgaggaagcg gaagagcgcc    3300
caatacgcaa accgcctctc cccgcgcgtt ggccgattca ttaatgcagc tgtggtgtca    3360
tggtcggtga tcgccagggt gccgacgcgc atctcgactg catggtgcac caatgcttct    3420
ggcgtcaggc agccatcgga agctgtggta tggccgtgca ggtcgtaaat cactgcataa    3480
ttcgtgtcgc tcaaggcgca ctcccgttct ggataatgtt ttttgcgccg acatcataac    3540
ggttctggca aatattctga aatgagctgt tgacaattaa tcatcgaact agttaactag    3600
tacgcaagtt cacgtaaaaa gggtatcgcg gaatt                               3635
```

<210> SEQ ID NO 12
<211> LENGTH: 131
<212> TYPE: PRT
<213> ORGANISM: RNA phage AP205 coat protein

<400> SEQUENCE: 12

```
Met Ala Asn Lys Pro Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130
```

<210> SEQ ID NO 13
<211> LENGTH: 131
<212> TYPE: PRT
<213> ORGANISM: RNA phage AP205 coat protein

<400> SEQUENCE: 13

Met Ala Asn Lys Thr Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130

<210> SEQ ID NO 14
<211> LENGTH: 3613
<212> TYPE: DNA
<213> ORGANISM: plasmid pAP281 32

<400> SEQUENCE: 14
cgagctcgcc cctggcttat cgaaattaat acgactcact ataggagac cggaattcga      60
gctcgcccgg ggatcctcta gattaaccca acgcgtagga gtcaggccat ggcaaataag    120
acaatgcaac cgatcacatc tacagcaaat aaaattgtgt ggtcggatcc aactcgttta    180
tcaactacat tttcagcaag tctgttacgc caacgtgtta agttggtat agccgaactg     240
aataatgttt caggtcaata tgtatctgtt tataagcgtc ctgcacctaa accggaaggt    300
tgtgcagatg cctgtgtcat tatgccgaat gaaaaccaat ccattcgcac agtgatttca    360
gggtcagccg aaaacttggc taccttaaaa gcagaatggg aaactcacaa acgtaacgtt    420
gacacactct tcgcgagcgg caacgccggt ttgggtttcc ttgaccctac tgcggctatc    480
gtatcgtctg atactactgc ttaagcttgt attctatagt gtcacctaaa tcgtatgtgt    540
atgatacata aggttatgta ttaattgtag ccgcgttcta acgacaatat gtacaagcct    600
aattgtgtag catctggctt actgaagcag accctatcat ctctctcgta aactgccgtc    660
agagtcggtt tggttggacg aaccttctga gtttctggta acgccgttcc gcaccccgga    720
aatggtcacc gaaccaatca gcagggtcat cgctagccag atcctctacg ccggacgcat    780
cgtggccggc atcaccggcg ccacaggtgc ggttgctggc gcctatatcg ccgacatcac    840
cgatggggaa gatcgggctc gccacttcgg gctcatgagc gcttgtttcg cgtgggtat    900
ggtggcaggc cccgtggccg ggggactgtt gggcgccatc tccttgcatg caccattcct    960
tgcggcggcg gtgctcaacg gcctcaacct actactgggc tgcttcctaa tgcaggagtc   1020
gcataaggga gagcgtcgat atggtgcact ctcagtacaa tctgctctga tgccgcatag   1080
ttaagccaac tccgctatcg ctacgtgact gggtcatggc tgcgccccga cacccgccaa   1140

```
cacccgctga cgcgccctga cgggcttgtc tgctcccggc atccgcttac agacaagctg    1200
tgaccgtctc cgggagctgc atgtgtcaga ggttttcacc gtcatcaccg aaacgcgcga    1260
ggcagcttga agacgaaagg gcctcgtgat acgcctattt ttataggtta atgtcatgat    1320
aataatggtt tcttagacgt caggtggcac ttttcgggga atgtgcgcg gaacccctat     1380 ttgtttattt ttctaaatac attcaaatat gtatccgctc atgagacaat aaccctgata    1440
aatgcttcaa taatattgaa aaggaagag tatgagtatt caacatttcc gtgtcgccct     1500
tattcccttt tttgcggcat tttgccttcc tgttttgct cacccagaaa cgctggtgaa      1560
agtaaaagat gctgaagatc agttgggtgc acgagtgggt tacatcgaac tggatctcaa    1620
cagcggtaag atccttgaga gttttcgccc cgaagaacgt tttccaatga tgagcacttt    1680
taaagttctg ctatgtggcg cggtattatc ccgtattgac gccgggcaag agcaactcgg    1740
tcgccgcata cactattctc agaatgactt ggttgagtac tcaccagtca cagaaaagca    1800
tcttacggat ggcatgacag taagagaatt atgcagtgct gccataacca tgagtgataa    1860
cactgcggcc aacttacttc tgacaacgat cggaggaccg aaggagctaa ccgcttttt      1920 gcacaacatg ggggatcatg taactcgcct tgatcgttgg gaaccggagc tgaatgaagc    1980
cataccaaac gacgagcgtg acaccacgat gcctgtagca atggcaacaa cgttgcgcaa    2040
actattaact ggcgaactac ttactctagc ttcccggcaa caattaatag actggatgga    2100
ggcggataaa gttgcaggac cacttctgcg ctcggccctt ccggctggct ggtttattgc    2160
tgataaatct ggagccggtg agcgtgggtc tcgcggtatc attgcagcac tggggccaga    2220
tggtaagccc tcccgtatcg tagttatcta cacgacgggg agtcaggcaa ctatggatga    2280
acgaaataga cagatcgctg agataggtgc ctcactgatt aagcattggt aactgtcaga    2340
ccaagtttac tcatatatac tttagattga tttaaaactt cattttaat ttaaaaggat    2400 ctaggtgaag atcctttttg ataatctcat gaccaaaatc ccttaacgtg agttttcgtt    2460
ccactgagcg tcagaccccg tagaaaagat caaaggatct tcttgagatc ctttttttct    2520
gcgcgtaatc tgctgcttgc aaacaaaaaa accaccgcta ccagcggtgg tttgtttgcc    2580
ggatcaagag ctaccaactc tttttccgaa ggtaactggc ttcagcagag cgcagatacc    2640
aaatactgtc cttctagtgt agccgtagtt aggccaccac ttcaagaact ctgtagcacc    2700
gcctacatac ctcgctctgc taatcctgtt accagtggct gctgccagtg gcgataagtc    2760
gtgtcttacc gggttggact caagacgata gttaccggat aaggcgcagc ggtcgggctg    2820
aacggggggt tcgtgcacac agcccagctt ggagcgaacg acctacaccg aactgagata    2880
cctacagcgc gagcattgag aaagcgccac gcttcccgaa gggagaaagg cggacaggta    2940
tccggtaagc ggcagggtcg gaacaggaga gcgcacgagg gagcttccag ggggaaacgc    3000
ctggtatctt tatagtcctg tcgggtttcg ccacctctga cttgagcgtc gatttttgtg    3060
atgctcgtca gggggggcgga gcctatggaa aaacgccagc aacgcggcct ttttacggtt    3120
cctggccttt tgctggcctt ttgctcacat gttctttcct gcgttatccc ctgattctgt    3180
ggataaccgt attaccgcct ttgagtgagc tgataccgct cgccgcagcc gaacgaccga    3240
gcgcagcgag tcagtgagcg aggaagcgga agagcgccca atacgcaaac cgcctctccc    3300
cgcgcgttgg ccgattcatt aatgcagctg tggtgtcatg gtcggtgatc gccagggtgc    3360
cgacgcgcat ctcgactgca tggtgcacca atgcttctgg cgtcaggcag ccatcggaag    3420
ctgtggtatg gccgtgcagg tcgtaaatca ctgcataatt cgtgtcgctc aaggcgcact    3480
cccgttctgg ataatgtttt ttgcgccgac atcataacgg ttctggcaaa tattctgaaa    3540
```

-continued

```
tgagctgttg acaattaatc atcgaactag ttaactagta cgcaagttca cgtaaaaagg    3600
gtatcgcgga att                                                       3613
```

<210> SEQ ID NO 15
<211> LENGTH: 14
<212> TYPE: PRT
<213> ORGANISM: Homo sapiens

<400> SEQUENCE: 15

```
Asp Arg Val Tyr Ile His Pro Phe His Leu Val Ile His Asn
1               5                   10
```

<210> SEQ ID NO 16
<211> LENGTH: 10
<212> TYPE: PRT
<213> ORGANISM: Artificial Sequence
<220> FEATURE:
<223> OTHER INFORMATION: angiotensin I peptide moiety

<400> SEQUENCE: 16

```
Asp Arg Val Tyr Ile His Pro Phe His Leu
1               5                   10
```

<210> SEQ ID NO 17
<211> LENGTH: 8
<212> TYPE: PRT
<213> ORGANISM: Artificial Sequence
<220> FEATURE:
<223> OTHER INFORMATION: angiotensin II peptide moiety

<400> SEQUENCE: 17

```
Asp Arg Val Tyr Ile His Pro Phe
1               5
```

<210> SEQ ID NO 18
<211> LENGTH: 35
<212> TYPE: DNA
<213> ORGANISM: Artificial Sequence
<220> FEATURE:
<223> OTHER INFORMATION: vector pQb185

<400> SEQUENCE: 18

```
tctagattaa cccaacgcgt aggagtcagg ccatg                               35
```

<210> SEQ ID NO 19
<211> LENGTH: 11
<212> TYPE: PRT
<213> ORGANISM: Artificial Sequence
<220> FEATURE:
<223> OTHER INFORMATION: "Angio 1" angiotensin derived peptide

<400> SEQUENCE: 19

```
Cys Gly Gly Asp Arg Val Tyr Ile His Pro Phe
1               5                   10
```

<210> SEQ ID NO 20
<211> LENGTH: 13
<212> TYPE: PRT
<213> ORGANISM: Artificial Sequence
<220> FEATURE:
<223> OTHER INFORMATION: "Angio 2" angiotensin derived peptide

<400> SEQUENCE: 20

```
Cys Gly Gly Asp Arg Val Tyr Ile His Pro Phe His Leu
1               5                   10
```

```
<210> SEQ ID NO 21
<211> LENGTH: 13
<212> TYPE: PRT
<213> ORGANISM: Artificial Sequence
<220> FEATURE:
<223> OTHER INFORMATION: "Angio 3" angiotensin derived peptide

<400> SEQUENCE: 21

Asp Arg Val Tyr Ile His Pro Phe His Leu Gly Gly Cys
1               5                   10

<210> SEQ ID NO 22
<211> LENGTH: 11
<212> TYPE: PRT
<213> ORGANISM: Artificial Sequence
<220> FEATURE:
<223> OTHER INFORMATION: "Angio 4" angiotensin derived peptide

<400> SEQUENCE: 22

Cys Asp Arg Val Tyr Ile His Pro Phe His Leu
1               5                   10

<210> SEQ ID NO 23
<211> LENGTH: 6
<212> TYPE: PRT
<213> ORGANISM: Artificial Sequence
<220> FEATURE:
<223> OTHER INFORMATION: "Angio 5" angiotensin derived peptide

<400> SEQUENCE: 23

Cys His Pro Phe His Leu
1               5

<210> SEQ ID NO 24
<211> LENGTH: 6
<212> TYPE: PRT
<213> ORGANISM: Artificial Sequence
<220> FEATURE:
<223> OTHER INFORMATION: "Angio 6" angiotensin derived peptide

<400> SEQUENCE: 24

Cys Gly Pro Phe His Leu
1               5

<210> SEQ ID NO 25
<211> LENGTH: 6
<212> TYPE: PRT
<213> ORGANISM: Artificial Sequence
<220> FEATURE:
<223> OTHER INFORMATION: "Angio 7" angiotensin derived peptide

<400> SEQUENCE: 25

Cys Tyr Ile His Pro Phe
1               5

<210> SEQ ID NO 26
<211> LENGTH: 6
<212> TYPE: PRT
<213> ORGANISM: Artificial Sequence
<220> FEATURE:
<223> OTHER INFORMATION: "Angio 8" angiotensin derived peptide

<400> SEQUENCE: 26

Cys Gly Ile His Pro Phe
1               5
```

```
<210> SEQ ID NO 27
<211> LENGTH: 6
<212> TYPE: PRT
<213> ORGANISM: Artificial Sequence
<220> FEATURE:
<223> OTHER INFORMATION: "Angio 9" angiotensin derived peptide

<400> SEQUENCE: 27

Cys Gly Gly His Pro Phe
1               5

<210> SEQ ID NO 28
<211> LENGTH: 8
<212> TYPE: PRT
<213> ORGANISM: Artificial Sequence
<220> FEATURE:
<223> OTHER INFORMATION: "Angio 13" angiotensin derived peptide

<400> SEQUENCE: 28

Asp Arg Val Tyr Ile Gly Gly Cys
1               5

<210> SEQ ID NO 29
<211> LENGTH: 7
<212> TYPE: PRT
<213> ORGANISM: Artificial Sequence
<220> FEATURE:
<223> OTHER INFORMATION: "Angio 14" angiotensin derived peptide

<400> SEQUENCE: 29

Asp Arg Val Tyr Gly Gly Cys
1               5

<210> SEQ ID NO 30
<211> LENGTH: 6
<212> TYPE: PRT
<213> ORGANISM: Artificial Sequence
<220> FEATURE:
<223> OTHER INFORMATION: "Angio 15" angiotensin derived peptide

<400> SEQUENCE: 30

Asp Arg Val Gly Gly Cys
1               5

<210> SEQ ID NO 31
<211> LENGTH: 8
<212> TYPE: PRT
<213> ORGANISM: Artificial Sequence
<220> FEATURE:
<223> OTHER INFORMATION: angiotensin derived peptide

<400> SEQUENCE: 31

Asp Arg Val Tyr Ile Gly Gly Cys
1               5

<210> SEQ ID NO 32
<211> LENGTH: 5
<212> TYPE: PRT
<213> ORGANISM: Artificial Sequence
<220> FEATURE:
<223> OTHER INFORMATION: HbcAG peptide

<400> SEQUENCE: 32

Gly Gly Lys Gly Gly
1               5
```

```
<210> SEQ ID NO 33
<211> LENGTH: 130
<212> TYPE: PRT
<213> ORGANISM: Bacteriophage fr

<400> SEQUENCE: 33

Met Ala Ser Asn Phe Glu Glu Phe Val Leu Val Asp Asn Gly Gly Thr
1               5                   10                  15
Gly Asp Val Lys Val Ala Pro Ser Asn Phe Ala Asn Gly Val Ala Glu
            20                  25                  30
Trp Ile Ser Ser Asn Ser Arg Ser Gln Ala Tyr Lys Val Thr Cys Ser
        35                  40                  45
Val Arg Gln Ser Ser Ala Asn Asn Arg Lys Tyr Thr Val Lys Val Glu
    50                  55                  60
Val Pro Lys Val Ala Thr Gln Val Gln Gly Gly Val Glu Leu Pro Val
65                  70                  75                  80
Ala Ala Trp Arg Ser Tyr Met Asn Met Glu Leu Thr Ile Pro Val Phe
                85                  90                  95
Ala Thr Asn Asp Asp Cys Ala Leu Ile Val Lys Ala Leu Gln Gly Thr
            100                 105                 110
Phe Lys Thr Gly Asn Pro Ile Ala Thr Ala Ile Ala Ala Asn Ser Gly
        115                 120                 125
Ile Tyr
    130

<210> SEQ ID NO 34
<211> LENGTH: 4
<212> TYPE: PRT
<213> ORGANISM: Artificial Sequence
<220> FEATURE:
<223> OTHER INFORMATION: angiotensin derived peptide

<400> SEQUENCE: 34

Asp Arg Val Tyr
1           4
```